(12) United States Patent
Larson et al.

(10) Patent No.: US 11,357,491 B2
(45) Date of Patent: Jun. 14, 2022

(54) SPINE STABILIZATION UTILIZING THE UNCINATE JOINTS

(71) Applicant: UNCINATE JOINT, LLC, Coeur d'Alene, ID (US)

(72) Inventors: Jeffrey John Larson, Coeur d'Alene, ID (US); Theodore P. Bertele, Longmont, CO (US)

(73) Assignee: Uncinate Joint, LLC, Coeur d'Alene, ID (US)

( * ) Notice: Subject to any disclaimer, the term of this patent is extended or adjusted under 35 U.S.C. 154(b) by 0 days.

(21) Appl. No.: 16/666,822

(22) Filed: Oct. 29, 2019

(65) Prior Publication Data
US 2020/0060667 A1 Feb. 27, 2020

Related U.S. Application Data

(63) Continuation of application No. 15/695,375, filed on Sep. 5, 2017, now abandoned, which is a continuation
(Continued)

(51) Int. Cl.
*A61B 17/02* (2006.01)
*A61F 2/44* (2006.01)
(Continued)

(52) U.S. Cl.
CPC ........ *A61B 17/025* (2013.01); *A61B 17/0206* (2013.01); *A61B 17/7053* (2013.01);
(Continued)

(58) Field of Classification Search
CPC .......... A61B 17/025; A61B 2017/0256; A61B 2017/0262; A61B 17/7062; A61F 2/4405
See application file for complete search history.

(56) References Cited

U.S. PATENT DOCUMENTS

| 5,609,635 A | 3/1997 | Michelson |
| 5,968,098 A | 10/1999 | Winslow |

(Continued)

FOREIGN PATENT DOCUMENTS

| AU | 2016225063 | 9/2017 |
| AU | 2019251997 | 11/2020 |

(Continued)

OTHER PUBLICATIONS

European Patent Application No. 16756491.3 extended Search and Opinion dated Sep. 28, 2018, 11 pages.
(Continued)

*Primary Examiner* — Julianna N Harvey
(74) *Attorney, Agent, or Firm* — Middleton Reutlinger

(57) ABSTRACT

A system for stabilizing a cervical spine segment utilizing uncinate joint stabilization, includes a stabilizing bridge for bridging across intervertebral disc space of the cervical spine segment to mechanically couple between a pair of uncinate joint stabilizers positioned in a respective pair of uncinate joints of the cervical spine segment. A method for stabilizing a cervical spine segment utilizing uncinate joint stabilization includes (a) positioning a pair of uncinate joint stabilizers in respective uncinate joints of the cervical spine segment to stabilize the uncinate joints and thereby stabilize the cervical spine segment (b) and implanting, in intervertebral disc space of the cervical spine segment, a stabilizing bridge that mechanically couples between the uncinate joint stabilizers across intervertebral disc space of the cervical spine segment.

17 Claims, 44 Drawing Sheets

Related U.S. Application Data of application No. 15/694,579, filed on Sep. 1, 2017, now Pat. No. 10,433,829, which is a continuation-in-part of application No. 15/553,556, filed as application No. PCT/US2016/019896 on Feb. 26, 2016, now Pat. No. 10,117,752.

(60) Provisional application No. 62/121,260, filed on Feb. 26, 2015.

(51) Int. Cl.
| | |
|---|---|
| *A61B 17/70* | (2006.01) |
| *A61F 2/46* | (2006.01) |
| *A61F 2/30* | (2006.01) |
| *A61B 90/00* | (2016.01) |
| *A61B 17/00* | (2006.01) |
| *A61B 17/68* | (2006.01) |
| *A61B 17/56* | (2006.01) |

(52) U.S. Cl.
CPC ...... *A61B 17/7059* (2013.01); *A61B 17/7062* (2013.01); *A61F 2/4405* (2013.01); *A61F 2/4455* (2013.01); *A61F 2/4684* (2013.01); *A61B 17/00234* (2013.01); *A61B 17/0218* (2013.01); *A61B 2017/00261* (2013.01); *A61B 2017/00477* (2013.01); *A61B 2017/0256* (2013.01); *A61B 2017/564* (2013.01); *A61B 2017/681* (2013.01); *A61B 2090/061* (2016.02); *A61B 2090/0807* (2016.02); *A61F 2002/3055* (2013.01); *A61F 2002/30538* (2013.01); *A61F 2002/30579* (2013.01); *A61F 2002/30593* (2013.01)

(56) References Cited

U.S. PATENT DOCUMENTS

| | | | |
|---|---|---|---|
| 6,039,761 | A | 3/2000 | Li et al. |
| 6,090,143 | A | 7/2000 | Meriwether |
| 6,210,412 | B1 | 4/2001 | Michelson |
| 6,325,827 | B1 | 12/2001 | Lin |
| 6,723,126 | B1 | 4/2004 | Berry |
| 7,494,463 | B2 | 2/2009 | Nehls |
| 8,070,782 | B2 | 12/2011 | McKay |
| 8,617,244 | B2 | 12/2013 | Reichen et al. |
| 8,663,293 | B2 | 3/2014 | Assell et al. |
| 9,956,084 | B2 | 5/2018 | Larson et al. |
| 10,117,752 | B2 | 11/2018 | Larson |
| 10,149,769 | B2 | 12/2018 | Larson |
| 10,350,080 | B2 | 7/2019 | Larson |
| 10,383,614 | B2 | 8/2019 | Larson |
| 10,433,829 | B2 | 10/2019 | Larson |
| 2002/0099444 | A1 | 7/2002 | Boyd et al. |
| 2002/0111679 | A1 | 8/2002 | Zucherman et al. |
| 2002/0128717 | A1 | 9/2002 | Alfaro et al. |
| 2002/0156478 | A1 | 10/2002 | Bonutti |
| 2003/0055430 | A1 | 3/2003 | Kim |
| 2004/0176764 | A1 | 9/2004 | Dant |
| 2005/0187626 | A1 | 8/2005 | McKay et al. |
| 2005/0192669 | A1 | 9/2005 | Zdeblick et al. |
| 2006/0089646 | A1 | 4/2006 | Bonutti |
| 2006/0241764 | A1 | 10/2006 | Michelson |
| 2007/0083266 | A1 | 4/2007 | Lang |
| 2007/0100212 | A1 | 5/2007 | Pimenta et al. |
| 2007/0265627 | A1 | 11/2007 | Dorchak et al. |
| 2007/0282448 | A1 | 12/2007 | Abdou |
| 2009/0043394 | A1 | 2/2009 | Zdeblick et al. |
| 2009/0276045 | A1 | 11/2009 | Lang |
| 2010/0152793 | A1 | 6/2010 | Lowry et al. |
| 2012/0185048 | A1 | 7/2012 | Phelps |
| 2012/0290092 | A1 | 11/2012 | Michelson |
| 2013/0053894 | A1 | 2/2013 | Gamache et al. |
| 2013/0103152 | A1 | 4/2013 | Kwon |
| 2013/0238039 | A1 | 9/2013 | Bonutti |
| 2013/0268076 | A1 | 10/2013 | Carlson et al. |
| 2014/0277495 | A1 | 9/2014 | Muhana et al. |
| 2014/0288565 | A1 | 9/2014 | McCormack et al. |
| 2015/0282941 | A1* | 10/2015 | Chokshi ............... A61F 2/4465 623/17.16 |
| 2017/0100117 | A1 | 4/2017 | Sahai et al. |
| 2017/0189201 | A1 | 7/2017 | Yang |
| 2017/0354515 | A1 | 12/2017 | Larson et al. |
| 2017/0354516 | A1 | 12/2017 | Larson et al. |
| 2018/0008428 | A1 | 1/2018 | Larson et al. |
| 2018/0021031 | A1 | 1/2018 | Larson |
| 2018/0021069 | A1 | 1/2018 | Larson et al. |
| 2018/0036139 | A1 | 2/2018 | Larson et al. |
| 2020/0060667 | A1 | 2/2020 | Larson |
| 2021/0030408 | A1 | 2/2021 | Larson |

FOREIGN PATENT DOCUMENTS

| | | |
|---|---|---|
| AU | 2020289724 | 1/2021 |
| CN | 107530094 A | 1/2018 |
| EP | 1043 002 A2 | 11/2010 |
| EP | 3261560 | 10/2018 |
| EP | 3773260 | 2/2021 |
| JP | 2018506393 | 3/2018 |
| JP | 2020089798 | 6/2020 |
| JP | 2021520877 | 8/2021 |
| WO | WO 97/31517 A2 | 8/1997 |
| WO | WO 02/41811 A1 | 5/2002 |
| WO | WO 2016138451 A1 | 2/2016 |
| WO | 2019199934 | 10/2019 |

OTHER PUBLICATIONS

PCT/US2016/019896 International Preliminary Reporton Patentability dated Jan. 27, 2017, 58 pages.
PCT/US2016/019896 International Search Report and Written Opinion dated Jul. 5, 2016, 19 pages.
PCT/US2016/019896 Response to Written Opinion dated Dec. 19, 2016, 52 pages.
U.S. Appl. No. 15/553,556 Notice of Allowance dated Sep. 26, 2018, 6 pages.
U.S. Appl. No. 15/687,945 Final Rejection dated Jan. 23, 2019, 13 pages.
U.S. Appl. No. 15/687,945 Non-Final Rejection dated Jul. 6, 2018, 14 pages.
U.S. Appl. No. 15/687,970 Non-Final Rejection dated Feb. 1, 2018, 11 pages.
U.S. Appl. No. 15/687,970 Notice of Allowance dated Oct. 10, 2018, 5 pages.
U.S. Appl. No. 15/687,970 Office Action dated Jul. 9, 2018, 10 pages.
U.S. Appl. No. 15/688,419 Non-Final Rejection dated Nov. 17, 2017, 7 pages.
U.S. Appl. No. 15/688,419 Notice of Allowance dated Feb. 2, 2018, 5 pages.
U.S. Appl. No. 15/694,579 Office Action dated Mar. 7, 2019, 15 pages.
U.S. Appl. No. 15/694,579 Response to Office Action filed Jan. 11, 2019, 8 pages.
U.S. Appl. No. 15/553,556 Non-Final Rejection dated Apr. 11, 2018, 11 pages.
Japanese Patent Application No. 2017-545662, English translation of Office Action dated Dec. 27, 2019, 9 pages.
Japan Patent Office Office Action for app. No. 2017-545662 dated Aug. 25, 2021, 12 pages.
Japan Patent Office, Notice of Reasons for Refusal for app. No. 2020-044433, dated Jan. 5, 2021.
Japan Patent Office, Notice of Reasons for Rejection for app. No. 2017-545662 dated Jan. 26, 2022.
Japanese Patent App. No. 2017-545662, English translation of Office Action, 5 pages, dated Jan. 26, 2022.
European Patent App. No. 19786225.3 extended Search and Opinion, 5 pages, dated Jan. 4, 2022.

(56) References Cited

OTHER PUBLICATIONS

PCT/US2019/026740 International Search Report and Written Opinion, 9 pages, dated Jun. 27, 2019.

* cited by examiner

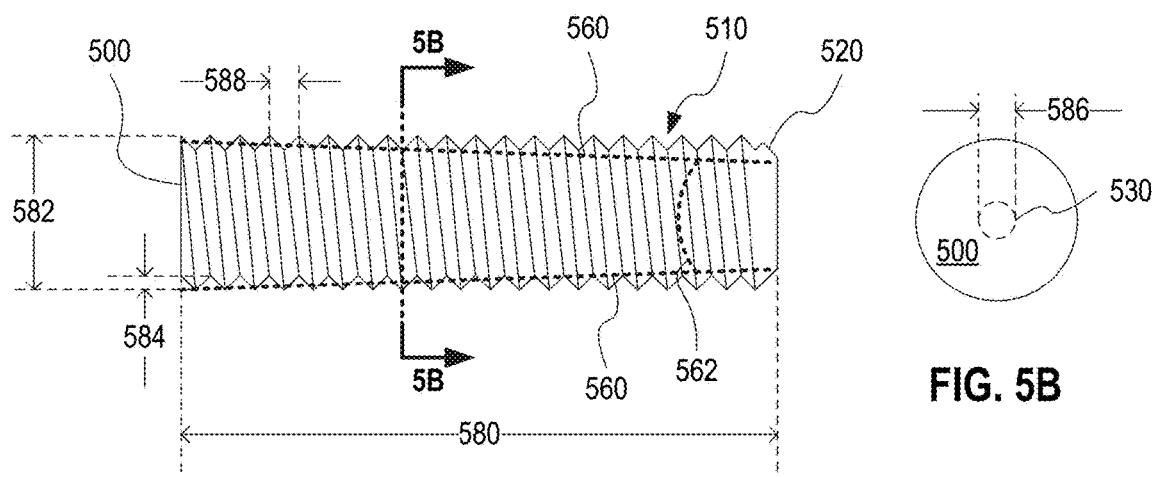
FIG. 5A
FIG. 5B
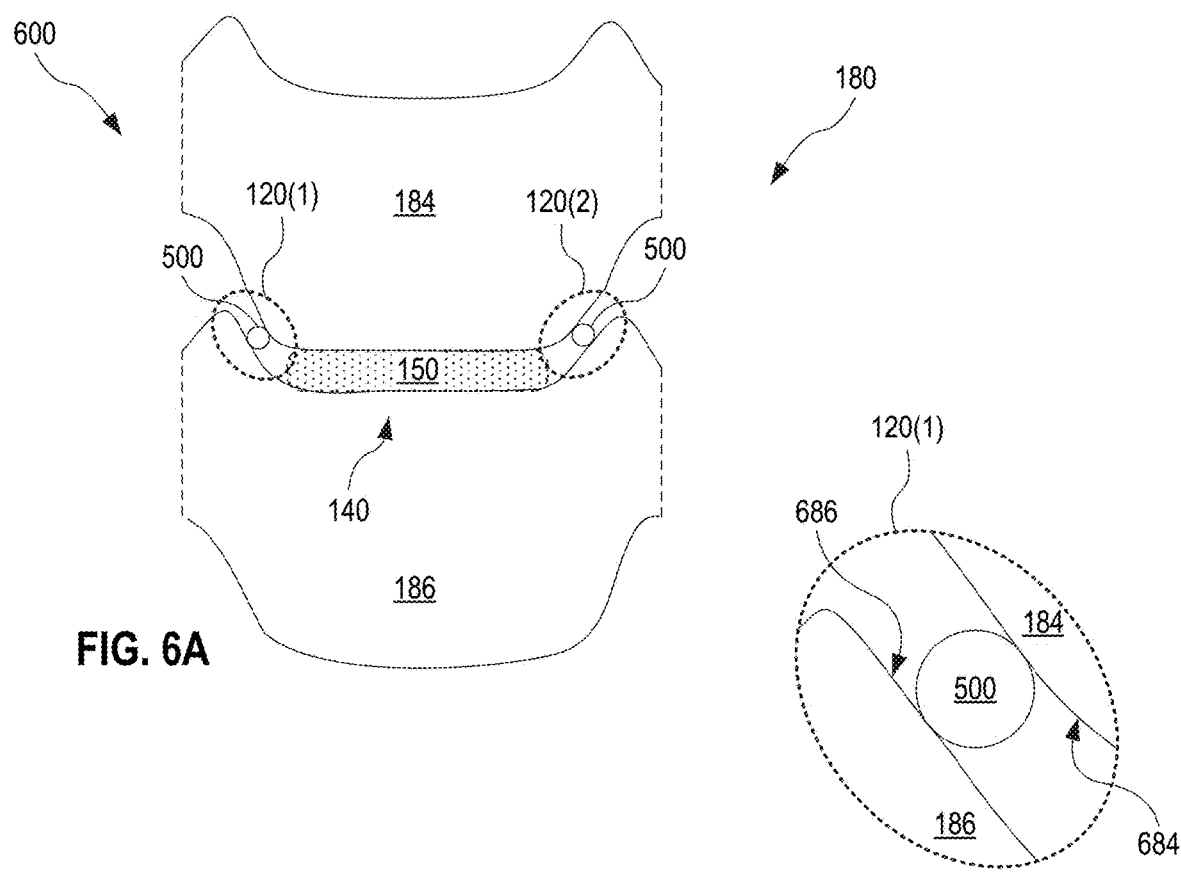
FIG. 6A
FIG. 6B

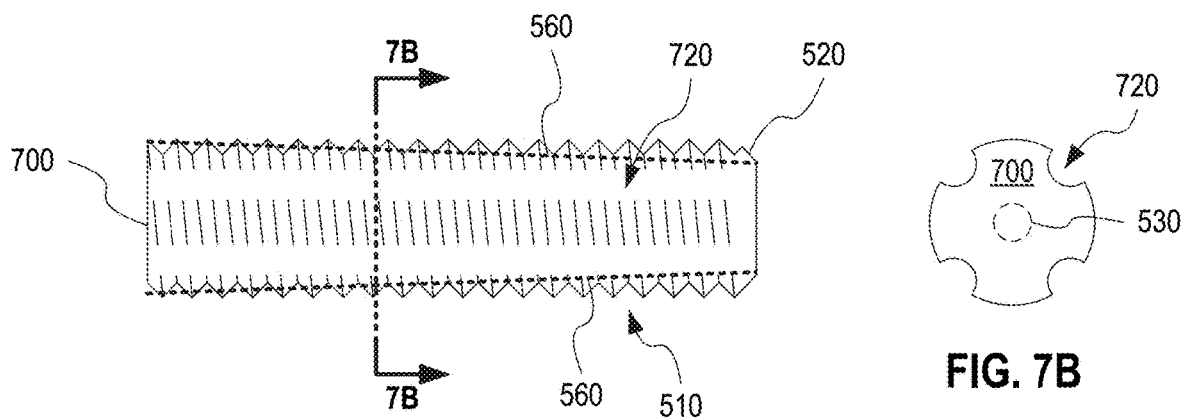
FIG. 7A
FIG. 7B
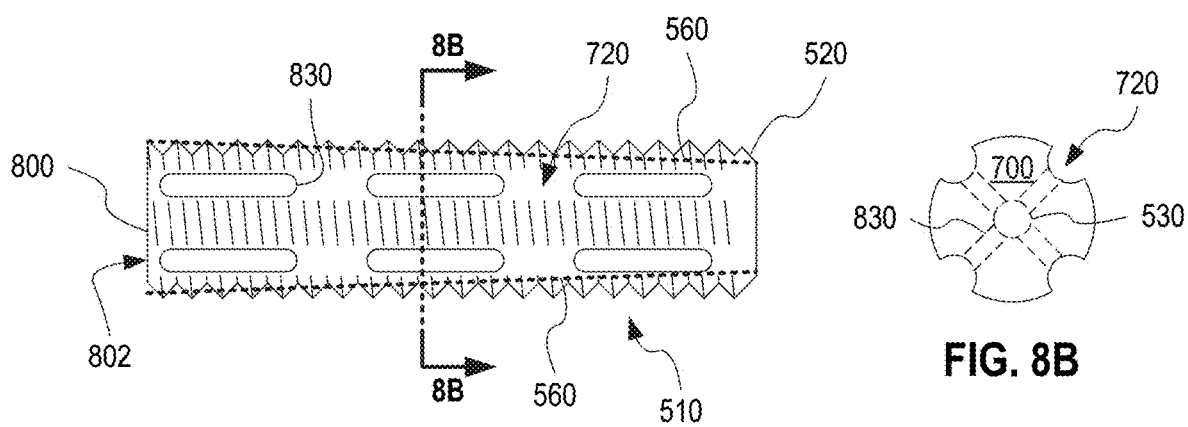
FIG. 8A
FIG. 8B
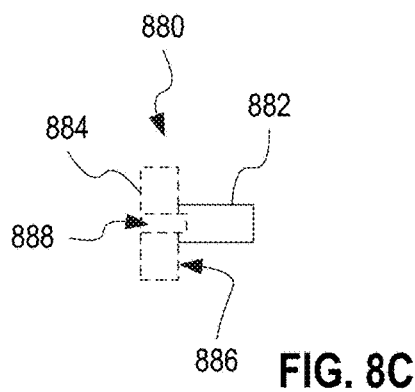
FIG. 8C
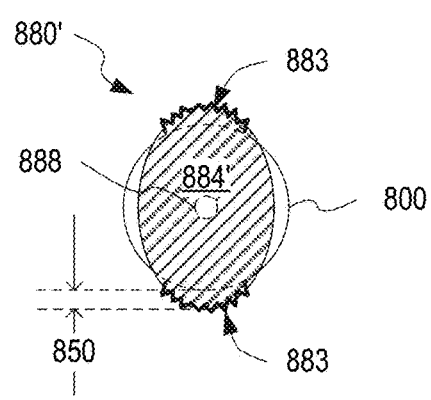
FIG. 8D

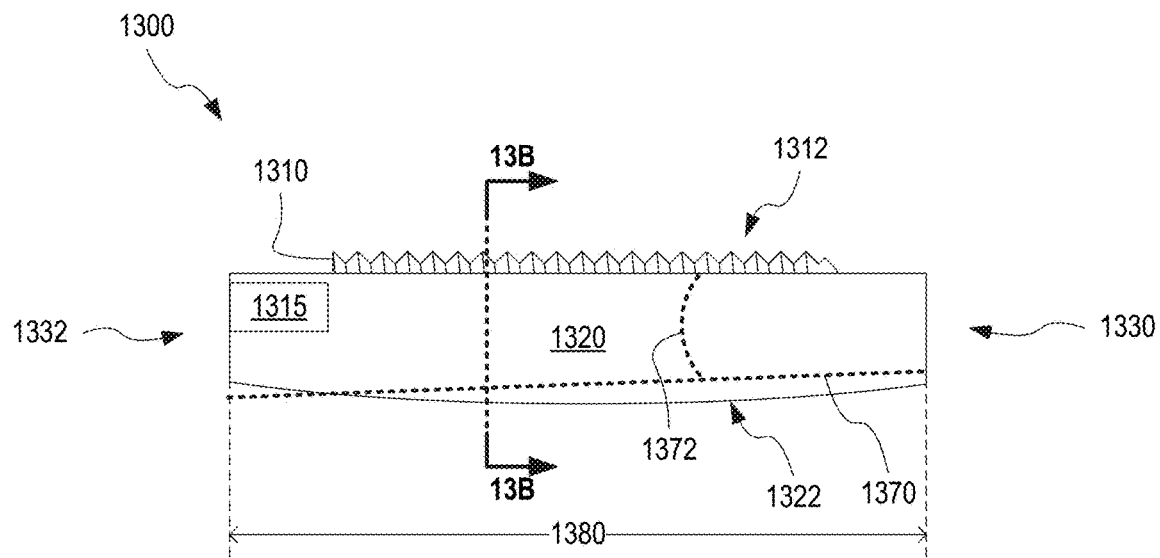
FIG. 13A
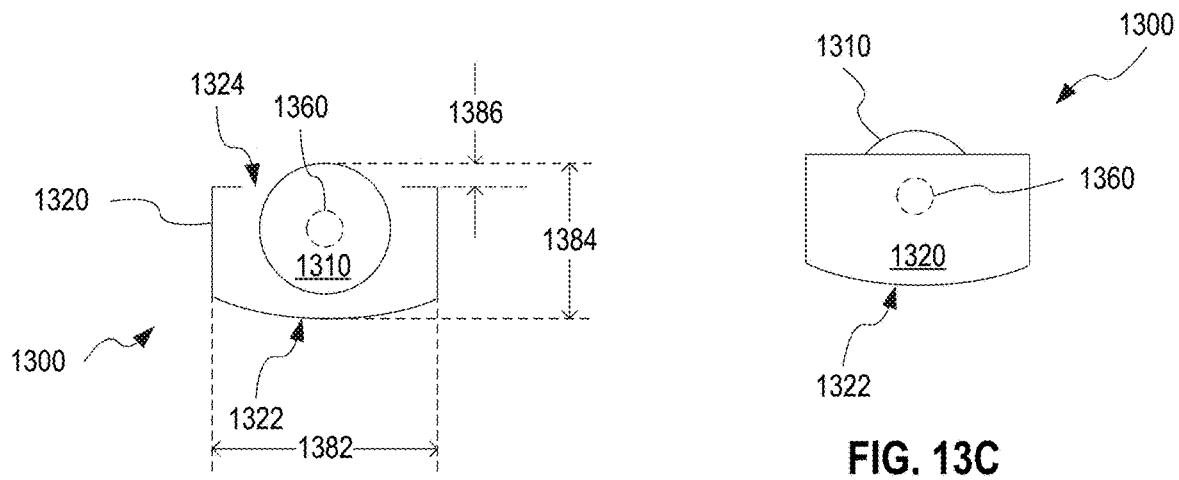
FIG. 13B
FIG. 13C
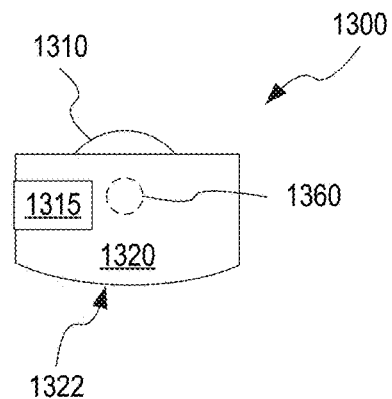
FIG. 13D

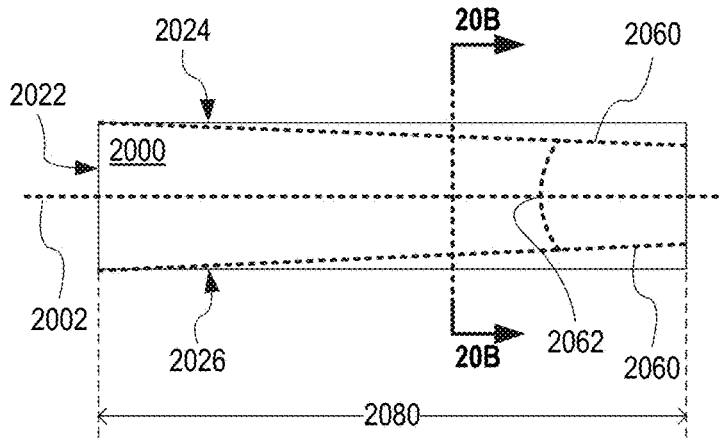
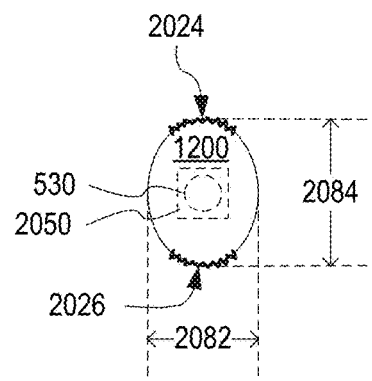
FIG. 20A                    FIG. 20B
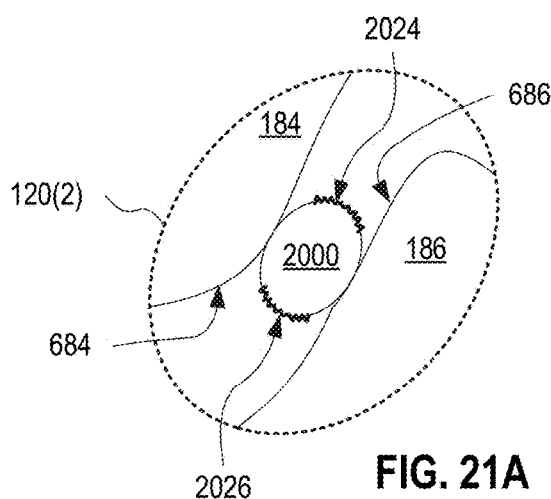
FIG. 21A
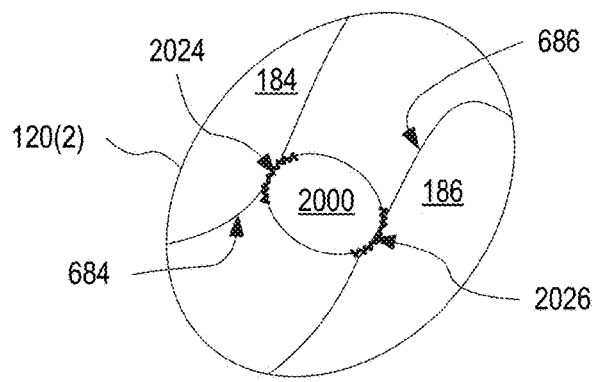
FIG. 21B

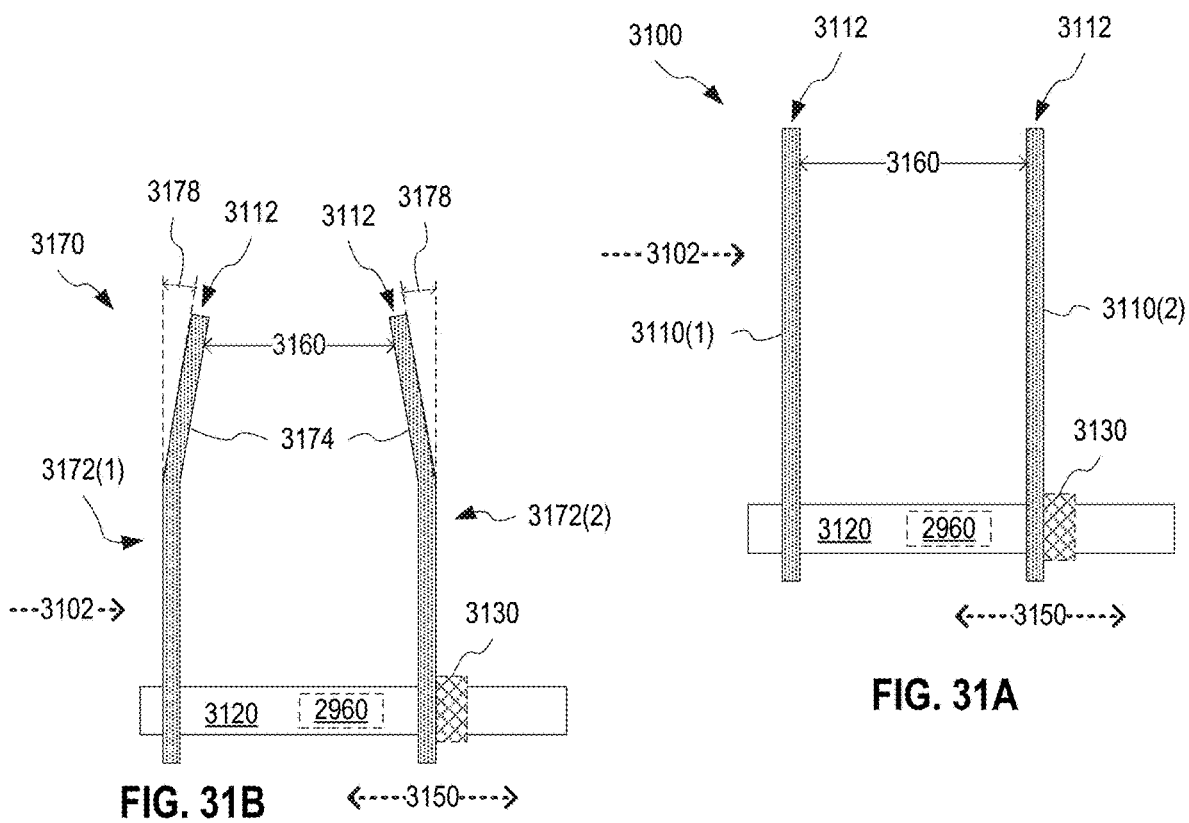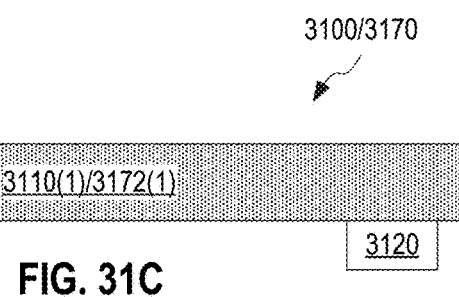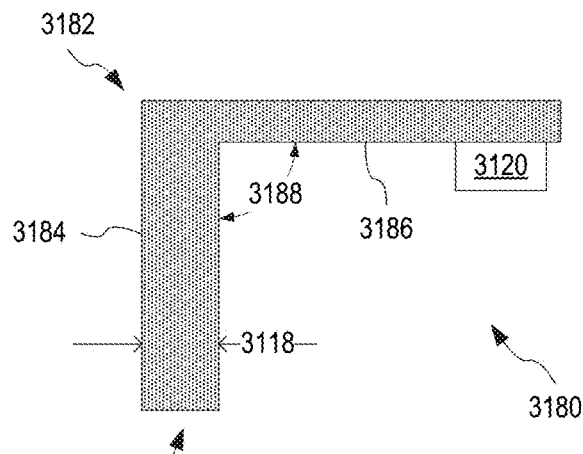

```
                                    5000
                                      ↓

┌─────────────────────────────────────────────────────────────────────────────┐
│  PERFORM METHOD 3700 TO AT LEAST PARTLY DISTRACT UNCINATE JOINTS, USING     │
│  UNCINATE JOINT STABILIZERS                                                 │
│                              5010                                           │
└─────────────────────────────────────────────────────────────────────────────┘
                                      ↓
┌─────────────────────────────────────────────────────────────────────────────┐
│ IMPLANT UNCINATE JOINT STABILIZERS IN UNCINATE JOINTS TO STABILIZE UNCINATE │
│ JOINTS, THEREBY STABILIZING CERVICAL SPINE SEGMENT                          │
│                              5020                                           │
│  ┌───────────────────────────────────────────────────────────────────────┐  │
│  │ LEAVE, IN UNCINATE JOINTS, UNCINATE JOINT STABILIZERS USED FOR        │  │
│  │ DISTRACTION IN STEP 5010                                              │  │
│  │                        5022                                           │  │
│  └───────────────────────────────────────────────────────────────────────┘  │
│  ┌───────────────────────────────────────────────────────────────────────┐  │
│  │ PROMOTE FUSION IN UNCINATE JOINTS BY LOADING BONE GRAFT MATERIAL INTO │  │
│  │ THE UNCINATE JOINTS VIA THE UNCINATE JOINT STABILIZERS                │  │
│  │                        4912                                           │  │
│  └───────────────────────────────────────────────────────────────────────┘  │
└─────────────────────────────────────────────────────────────────────────────┘
                                      ↓
┌─────────────────────────────────────────────────────────────────────────────┐
│  DISTRACT OPEN IVDS TO PREPARE IVDS FOR IVDS IMPLANT                        │
│                              5030                                           │
└─────────────────────────────────────────────────────────────────────────────┘
                                      ↓
┌─────────────────────────────────────────────────────────────────────────────┐
│  IMPLANT, IN IVDS, STABILIZING BRIDGE THAT MECHANICALLY COUPLES BETWEEN     │
│  UNCINATE JOINT STABILIZERS ACROSS IVDS                                     │
│                              5040                                           │
│  ┌───────────────────────────────────────────────────────────────────────┐  │
│  │             PERFORM STEP 4920 OF METHOD 4900                          │  │
│  │                        5042                                           │  │
│  └───────────────────────────────────────────────────────────────────────┘  │
└─────────────────────────────────────────────────────────────────────────────┘
                                      ↓
┌─────────────────────────────────────────────────────────────────────────────┐
│                        REMOVE DISTRACTOR TOOL                               │
│                              5050                                           │
└─────────────────────────────────────────────────────────────────────────────┘
```

┌─────────────────────────────────────────────────────────────────────────────┐
│ PERFORM METHOD 3700 TO AT LEAST PARTLY DISTRACT UNCINATE JOINTS, USING TRIAL│
│ IMPLANTS, AND OBTAIN MEASUREMENT OF OPTIMAL UNCINATE JOINT STABILIZER SIZE  │
│                                  5110                                       │
└─────────────────────────────────────────────────────────────────────────────┘
                                       ▼
┌─────────────────────────────────────────────────────────────────────────────┐
│                          REMOVE TRIAL IMPLANTS                              │
│                                  5120                                       │
└─────────────────────────────────────────────────────────────────────────────┘
                                       ▼
┌─────────────────────────────────────────────────────────────────────────────┐
│ PERFORM STEPS 3720 AND 3730 OF METHOD 3700 WITH UNCINATE JOINT STABILIZERS TO│
│ IMPLANT UNCINATE JOINT STABILIZERS IN UNCINATE JOINTS, SO AS TO STABILIZE   │
│ UNCINATE JOINTS AND THEREBY STABILIZE CERVICAL SPINE SEGMENT, WHEREIN SIZE  │
│ OF UNCINATE JOINT STABILIZERS IS CHOSEN BASED ON TRIAL IMPLANT MEASUREMENT  │
│                                  5130                                       │
│  ┌───────────────────────────────────────────────────────────────────────┐  │
│  │ PROMOTE FUSION IN UNCINATE JOINTS BY LOADING BONE GRAFT MATERIAL INTO │  │
│  │         THE UNCINATE JOINTS VIA THE UNCINATE JOINT IMPLANTS           │  │
│  │                                5024                                   │  │
│  └───────────────────────────────────────────────────────────────────────┘  │
└─────────────────────────────────────────────────────────────────────────────┘
                                       ▼
┌─────────────────────────────────────────────────────────────────────────────┐
│             DISTRACT OPEN IVDS TO PREPARE IVDS FOR IVDS IMPLANT             │
│                                  5030                                       │
└─────────────────────────────────────────────────────────────────────────────┘
                                       ▼
┌─────────────────────────────────────────────────────────────────────────────┐
│   IMPLANT, IN IVDS, STABILIZING BRIDGE THAT MECHANICALLY COUPLES BETWEEN    │
│                   UNCINATE JOINT STABILIZERS ACROSS IVDS                    │
│                                  5040                                       │
│         ┌─────────────────────────────────────────────────────┐             │
│         │            PERFORM STEP 4920 OF METHOD 4900         │             │
│         │                        5042                         │             │
│         └─────────────────────────────────────────────────────┘             │
└─────────────────────────────────────────────────────────────────────────────┘
                                       ▼
                    ┌─────────────────────────────────────┐
                    │        REMOVE DISTRACTOR TOOL       │
                    │                5050                 │
                    └─────────────────────────────────────┘

FIG. 51
```

SPINE STABILIZATION UTILIZING THE UNCINATE JOINTS

CROSS-REFERENCE TO RELATED APPLICATIONS

The present application is a continuation of U.S. patent application Ser. No. 15/695,375, filed on Sep. 5, 2017, which is a continuation of U.S. patent application Ser. No. 15/694,579, filed on Sep. 1, 2017 (now U.S. Pat. No. 10,433,829), which is a continuation-in-part of U.S. patent application Ser. No. 15/553,556, filed on Aug. 24, 2017 (now U.S. Pat. No. 10,117,752), which is a 35 U.S.C. § 371 filing of International Application No. PCT/US2016/019896, filed Feb. 26, 2016, which claims the benefit of priority from U.S. Provisional Patent Application Ser. No. 62/121,260 filed on Feb. 26, 2015. All of the aforementioned applications are incorporated herein by reference in their entireties.

BACKGROUND

The cervical spine is the neck portion of the spine. The cervical spine has a series of seven vertebrae connecting the skull to the thoracic spine (upper back). These seven vertebrae are referred to as C1-C7, with C1 being closest to the skull and C7 being furthest from the skull. Each pair of neighboring vertebrae forms a cervical spine segment that allows movement of the spine, such as rotation and flexion. Each cervical spine segment includes an intervertebral disc that separates the two vertebrae to allow for smooth joint movement and provide cushioning.

The cervical spine houses the spinal cord responsible for neural communication between the brain and the body. Therefore, damage to the cervical spine can lead to neck pain, apparent pain in other parts of the body, and/or impaired functioning. For example, damage to the cervical spine may result in apparent arm pain or partial/complete loss of hand function. Although cervical spine damage may be caused by trauma, cervical spine damage usually is a gradual process occurring with aging. Common cervical spine damage includes degeneration of the intervertebral disc and degeneration of the uncinate joints located adjacent the intervertebral disc space. Intervertebral disc degeneration may cause spinal cord or nerve impingement from the formation of bone spurs and/or intervertebral disc protrusion. Uncinate joint degeneration may cause spinal cord or nerve impingement from the formation of bone spurs. Surgery may be required to resolve either of these issues.

Surgical methods used to resolve cervical spine damage traditionally include cervical discectomy (removal of intervertebral disc). The purpose of such surgery is to restore proper spacing between the cervical vertebrae of the damage cervical spine segment. The intervertebral disc may be replaced by a cage that includes bone graft material for subsequent fusion of the cervical spine segment. A fused cervical spine segment is stiff and does not allow for joint movement. Alternatively, the intervertebral disc is replaced by an artificial disc device that allows for active joint movement of the cervical spine segment.

Conventionally, cervical discectomy is performed from the front (the anterior side). To access the cervical spine segment, the surgeon (a) makes a skin incision in the front of the neck, (b) makes a tunnel to the spine by moving aside muscles and retracting the trachea, esophagus, and arteries, and (c) lifts and holds aside the longus colli muscles that support the front of the spine. Next, the surgeon screws pins into both the superior (upper) cervical vertebra and the inferior (lower) cervical vertebra of the cervical spine segment and uses these pins to increase the intervertebral spacing. The surgeon then performs the cervical discectomy and inserts a cage into the intervertebral disc space.

When the cage includes bone graft material, bone growth within the intervertebral disc space takes place over the next several months, ultimately fusing the cervical spine segment. Each vertebral body (the portion of the vertebra located above or below the intervertebral disc space) has a denser shell of cortical bone surrounding an inner, cylindrical core of spongy cancellous bone. At the intervertebral disc space, the cortical bone shell forms a ring around the cancellous bone. Fusion of the cervical spine segment requires bone growth between the two cortical bone shells of the cervical spine segment.

SUMMARY

In an embodiment, a method for stabilizing a cervical spine segment, includes implanting a respective uncinate joint stabilizer into each uncinate joint of the cervical spine segment to stabilize the uncinate joints and thereby stabilize the cervical spine segment.

In an embodiment, a system for stabilizing a cervical spine segment, includes a pair of uncinate joint stabilizers for stabilizing a respective pair of uncinate joints of the cervical spine segment. Each uncinate joint stabilizer is elongated along a lengthwise dimension and configured for placement in the respective uncinate joint with the lengthwise dimension substantially oriented along an anterior-to-posterior direction of the cervical spine segment. Each uncinate joint stabilizer has height in a heightwise dimension orthogonal to the lengthwise dimension. The height is configured to define spacing of the respective uncinate joint.

In an embodiment, a system for distracting uncinate joints of a cervical spine segment includes two tapered elements and an actuator. The actuator is configured to couple with the tapered elements and change distance between the tapered elements, to insert the tapered elements into the uncinate joints, respectively, from intervertebral disc space of the cervical spine segment.

In an embodiment, a tool for distracting uncinate joints of a cervical spine segment includes two connector arms configured to access the cervical spine segment through soft tissue anterior to the cervical spine segment. The connector arms form respective receptacles for holding extensions coupled to respective distractor tips so as to position the distractor tips at distal ends of the connector arms and in the cervical spine segment. The tool further includes a control coupled to proximate ends of the connector arms and configured to adjust distance between the connector arms, at least at the distal ends, to distract the uncinate joints with the distractor tips.

In an embodiment, a system for distracting uncinate joints of a cervical spine segment includes a pair of distractor tips for insertion into the uncinate joints, respectively, along a medial-to-lateral direction from intervertebral disc space of the cervical spine segment, to distract the uncinate joints. Each of the distractor tips has a lateral side and a medial side respectively facing and facing away from a respective one of the uncinate joints during the insertion. Height of each distractor tip increases gradually from the lateral side at least partway toward the medial side to ease the insertion.

BRIEF DESCRIPTION OF THE DRAWINGS

FIGS. 5A and 5B illustrate a threaded implant for stabilizing an uncinate joint, according to an embodiment.

FIGS. 6A and 6B depict a diagram showing, in an anterior view, a pair of the threaded implant of FIGS. 5A and 5B installed in the uncinate joints of a cervical spine segment according to the method of FIG. 4, according to an embodiment.

FIGS. 7A and 7B illustrate a fenestrated, threaded implant for stabilizing an uncinate joint, according to an embodiment.

FIGS. 8A and 8B illustrate another fenestrated, threaded implant for stabilizing an uncinate joint, according to an embodiment.

FIG. 8C illustrates a cap for sealing a through-hole of the fenestrated, threaded implant of FIGS. 8A and 8B, according to an embodiment.

FIG. 8D illustrates a cap which is an implementation of the cap of FIG. 8C, which further implements a locking lever, according to an embodiment.

FIGS. 13A, 13B, 13C, and 13D illustrate a motion-preserving implant for stabilizing an uncinate joint, according to an embodiment.

FIGS. 20A and 20B illustrate an implant configured to be tapped or slid into the uncinate joint and, after positioning in the uncinate joint, rotated to distract the uncinate joint and to be locked in place in the uncinate joint, according to an embodiment.

FIGS. 21A and 21B illustrate insertion of the implant of FIGS. 20A and 20B into the uncinate joint, according to an embodiment.

FIGS. 31A-D illustrate other actuators, according to embodiments.

FIG. 50 illustrates a method for stabilizing a cervical spine segment utilizing integrated uncinate joint distraction and stabilization, with additional stabilization across the intervertebral disc space, according to an embodiment.

FIG. 51 illustrates a method for stabilizing a cervical spine segment utilizing uncinate joint distraction and stabilization, with additional stabilization across the intervertebral disc space, which further utilizes trial implants to determine an optimal size for the uncinate joint stabilizers, according to an embodiment.

DETAILED DESCRIPTION OF THE EMBODIMENTS

Figure 1:
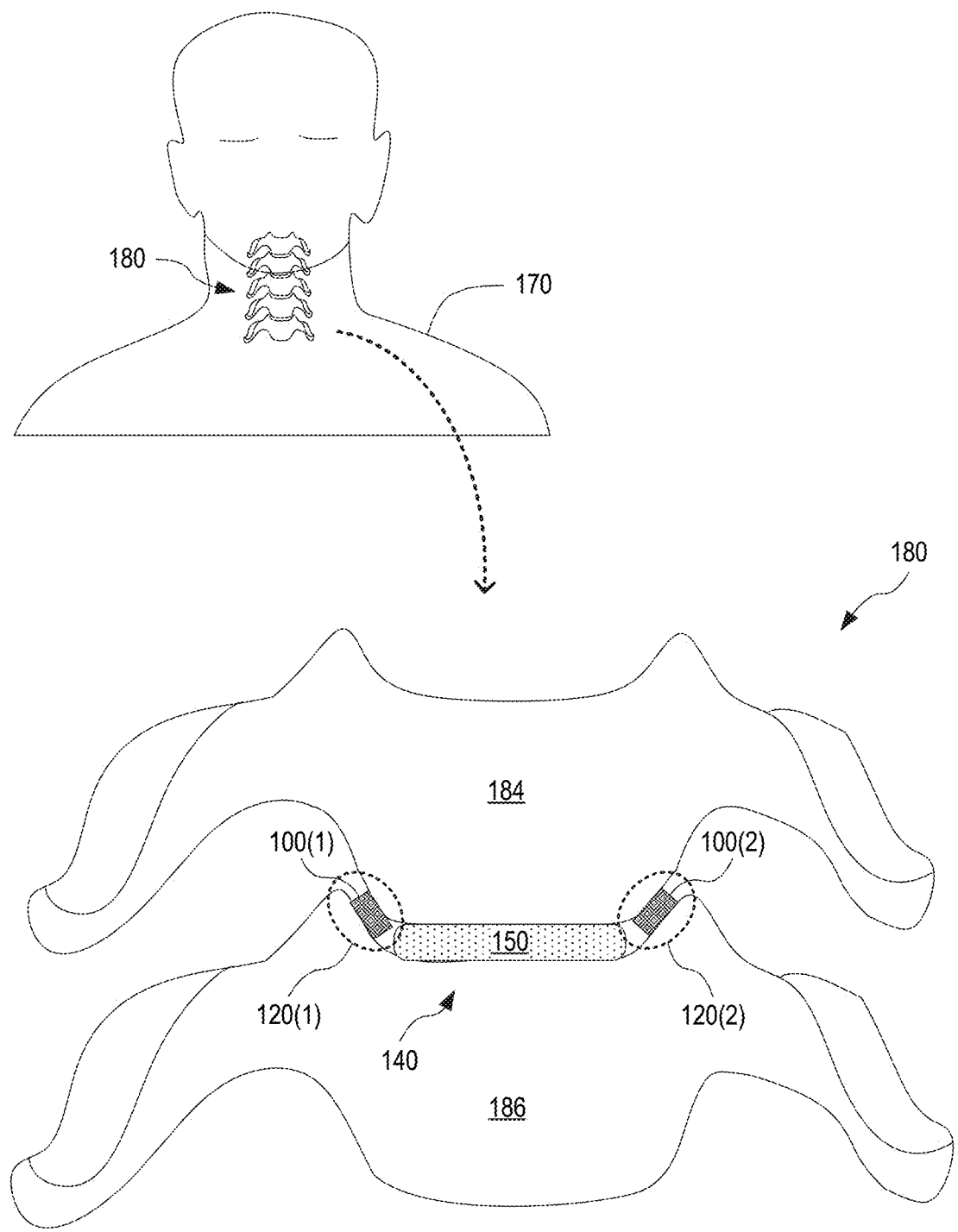
FIG. 1 illustrates implants that stabilize the uncinate joints of a cervical spine segment, according to an embodiment.

FIG. 1 illustrates two exemplary implants 100 that stabilize the uncinate joints 120 a cervical spine segment 180 of a patient 170, according to an embodiment. Implant 100 may also be referred to as an uncinate joint stabilizer. Cervical spine segment 180 includes superior vertebra 184 and inferior vertebra 186, wherein superior vertebra 184 is one of C3, C4, C5, and C6. Uncinate joints 120, also known as the uncovertebral joints or the joints of Luschka, are located adjacent the intervertebral disc space 140 of cervical spine segment 180. Uncinate joints 120 are associated with cortical bone of cervical vertebrae 184 and 186.

In one embodiment, implant 100 is a permanent implant that stays in place over the life of the patient, unless surgically removed. In another embodiment, implant 100 is biodegradable and eventually degrades. In one embodiment, implants 100 lock the mobility of cervical spine segment 180 and, optionally, include bone graft material that promotes fusion of uncinate joints 120. In one fusion-promoting example, implant 100 is porous or has cavities configured to accommodate bone graft material. In another fusion-promoting example, at least a portion of implant 100 is a porous portion composed of bone graft material that promotes bone growth in the pores thereof. Herein, "bone graft material" refers to a material that promotes bone growth. Exemplary bone graft materials include biological materials, stem cell based materials, synthetic bone growth promoting materials, other bone growth promoting materials known in the art, and a combination thereof. In another embodiment, implants 100 are motion-preserving implants that preserve at least some degree of mobility of cervical spine segment 180.

Implant 100 is notably smaller than conventional implants placed in intervertebral disc space 140. Hence, implant 100 may be less expensive, require less hardware, and be installed in uncinate joints 120 using less invasive methods than those associated with the installation of conventional implants placed in intervertebral disc space 140.

Disclosed herein are methods that insert implants 100 into uncinate joints 120 to stabilize cervical spine segment 180, while leaving intact intervertebral disc 150 located in intervertebral disc space 140. Herein, an "intact" intervertebral disc may refer to a disc that is entirely undisturbed by implants 100, or an intervertebral disc that is slightly altered by implant(s) 100 in a generally lateral dimension. In certain embodiments, the methods disclosed herein stabilize cervical spine segment 180 while preserving motion of cervical spine segment 180 and also allowing for normal health and functionality of intervertebral disc 150. These methods are, in certain embodiments, performed in a minimally invasive manner utilizing percutaneous access to uncinate joints 120. In contrast, conventional stabilization of cervical spine segment 180, based upon stabilization within intervertebral disc space 140, requires anterior access to intervertebral disc space 140, and relies on open access to intervertebral disc space 140. However, the methods discloses herein may, at least in some embodiments, be performed in open surgery. In one use scenario, the methods disclosed herein utilize biodegradable embodiments of implants 100, which stabilize uncinate joints 120 for a duration sufficient for healing of an injury to intervertebral disc 150, but subsequently degrades to play no or little role in the functionality of cervical spine segment 180. Also disclosed herein are methods that use implants 100 to stabilize uncinate joints 120 in conjunction with performing cervical discectomy. Whether implants 100 are used in conjunction with cervical discectomy or coexist in cervical spine segment 180 with an intact intervertebral disc 150, implants 100 may include or be substantially composed of bone graft material to promote (a) fusion of uncinate joints 120 or (b) bony ingrowth in uncinate joints 120 at the interfaces between implants 100 and one of cervical vertebrae 184 and 186. Since the surfaces of uncinate joints 120 are cortical bone, such fusion is expected to be fast and strong.

Figure 2:
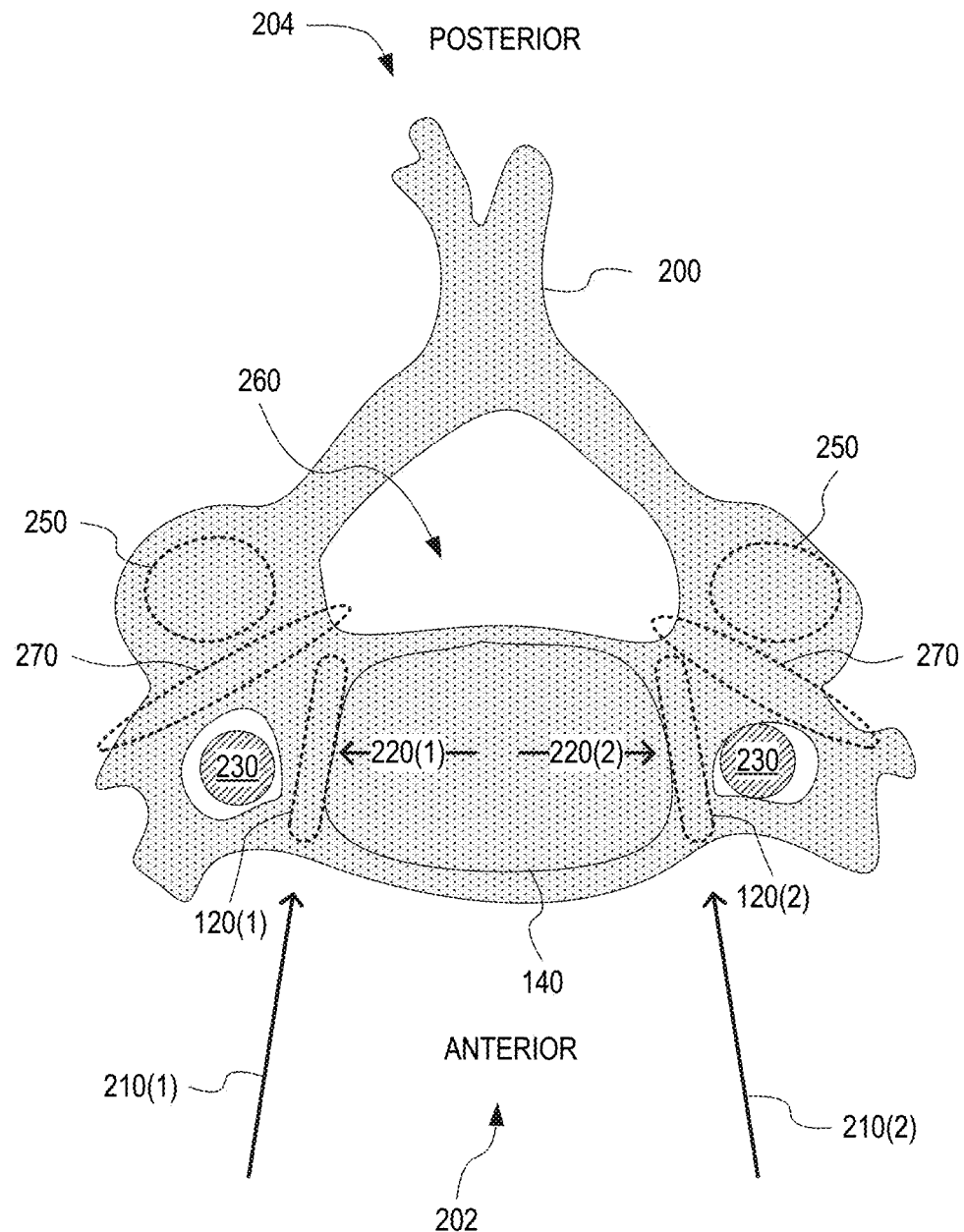
FIG. 2 shows an axial view (along the spine) of a cervical vertebra that is one of vertebra C3-C7.

FIG. 2 shows an axial view (along the spine) of a cervical vertebra 200 that is one of vertebrae C3-C7. Cervical vertebra 200 is, for example, one of cervical vertebrae 184 and 186. Label 202 indicates the anterior (front) side of cervical vertebra 200 and label 204 indicates the posterior (back) side of cervical vertebra 200. Uncinate joints 120 are located adjacent intervertebral disc space 140. Cervical vertebra 200 includes surfaces for forming facet joints 250 with a neighboring cervical vertebra 200. FIG. 2 further indicates the locations of vertebral arteries 230 passing through cervical vertebra 200. The spinal canal 260 is located posterior to intervertebral disc space 240. The spinal cord passes through spinal canal 260. Nerve roots pass through the neural foramen along paths 270.

Referring now to FIGS. 1 and 2 in combination, each implant 100 may be inserted into the respective uncinate joint 120 along an anterior-to-posterior direction 210. Herein, "anterior-to-posterior direction" refers to a direction that is generally from anterior side 202 towards posterior side 204, such that access to uncinate joint 120 along anterior-to-posterior direction 210 does not require passing through intervertebral disc space 140. Thus, when inserting implants 100 into uncinate joints 120 along anterior-to-posterior direction 210, intervertebral disc 150 may be left intact. Alternatively, each implant 100 may be inserted into the respective uncinate joint 120 along a medial-to-lateral direction 220. Herein, "medial-to-lateral direction" refers to a direction that is from intervertebral disc space 140 towards either one of uncinate joints 120. Thus, when inserting implants 100 into uncinate joints 120 along medial-to-lateral direction 220, implants 100 are inserted into uncinate joints 120 from intervertebral disc space 140.

Figure 3:
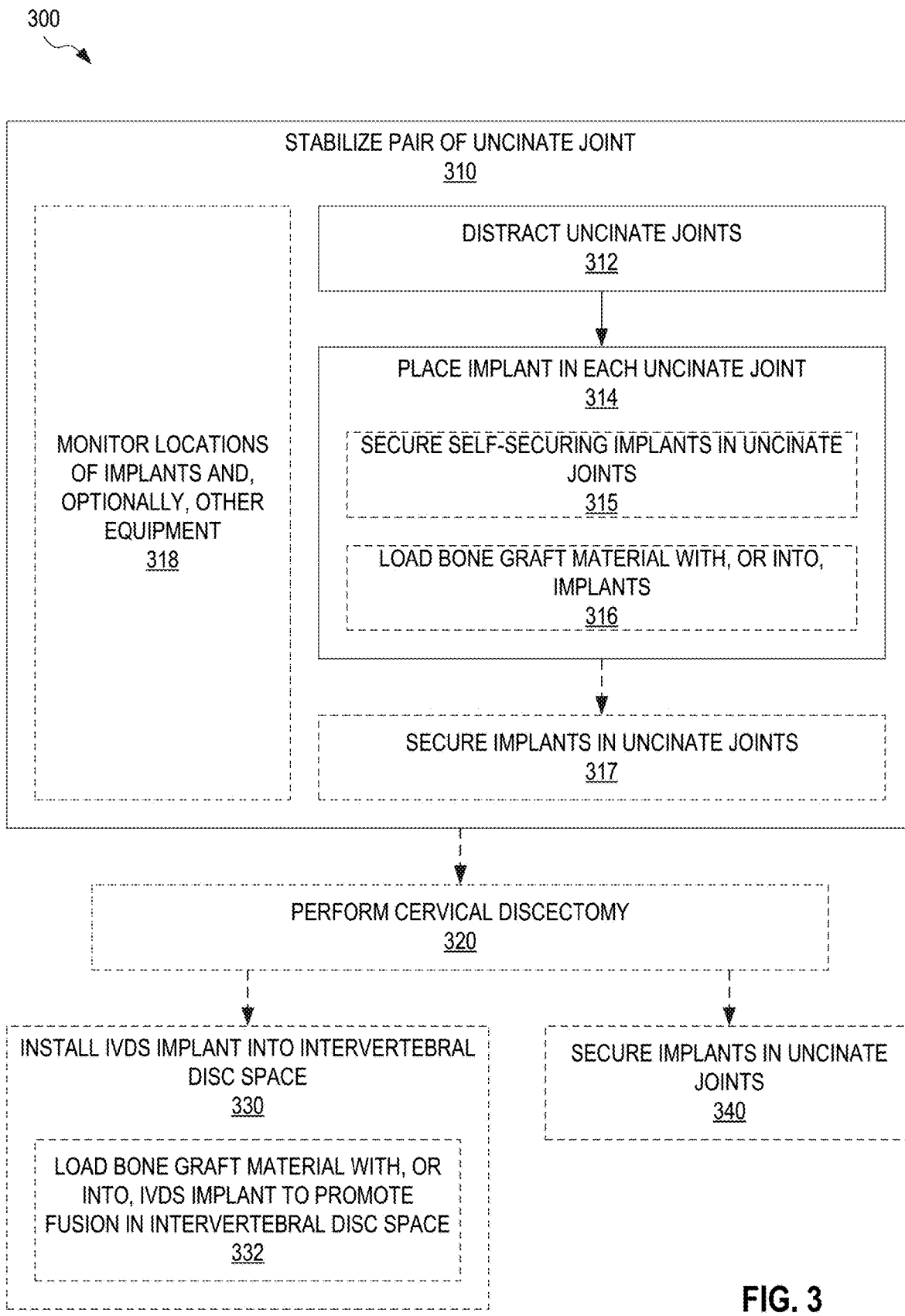
FIG. 3 illustrates a method for stabilizing a cervical spine segment by inserting implants into the uncinate joints of the cervical spine segment, according to an embodiment.

FIG. 3 illustrates one exemplary method 300 for stabilizing cervical spine segment 180 (FIG. 1) by inserting implants 100 into uncinate joints 120 of cervical spine segment 180. In method 300, uncinate joints 120 may be accessed via anterior-to-posterior directions 210 (FIG. 2) or via medial-to-lateral directions 220.

In a step 310, method 300 stabilizes uncinate joints 120. Step 310 includes steps 312 and 314. Step 312 distracts each uncinate joint 120 to prepare uncinate joints 120 for insertion of implants 100. In one example of step 312, a surgeon inserts a distraction tool into each uncinate joint 120 along anterior-to-posterior direction 210 or along medial-to-lateral directions 220, and uses this distraction tool to open uncinate joint 120. Herein, a "surgeon" may be assisted or replaced by robotic equipment without departing from the scope hereof. Step 314 places implants 100 into respective uncinate joints 120. Herein, a step of placing an implant may also be referred to as a step of implanting an uncinate joint stabilizer. In one example of step 314, a surgeon inserts implant 100 into each uncinate joint 120. Implants 100 used in step 314 may also perform step 312, and step 314 may be performed concurrently with or prior to step 312, without departing from the scope hereof.

In one implementation of method 300, implants 100 are self-securing and step 314 includes a step 315 of securing such self-securing embodiments of implants 100 in uncinate joints 120. Herein, a "self-securing" implant is an implant that stays in place without use of additional hardware. In one example, a self-securing embodiment of implant 100 has features that grip the surface of one or both of cervical vertebrae 184 and 186 at uncinate joint 120. A "self-securing" implant may secure itself at least in part by cooperation with a tension band. Herein, a "tension band" refers to one or more ligaments of cervical spine segment 180, which pull cervical vertebrae 184 and 186 toward each other. Hence, in one example of step 315, a surgeon places self-securing implants 100 in respective uncinate joints 120, where each implant 100 cooperates with respective uncinate joint 120 and, optionally, a tension band to secure itself.

In one implementation, step 314 includes a step 316 of loading bone graft material with, or into, implants 100 to promote subsequent (a) fusion of uncinate joints 120 or (b) bony ingrowth in uncinate joints 120 at interfaces between implants 100 and one of cervical vertebrae 184 and 186. In one example of step 314 implemented with step 316, a surgeon inserts, into each uncinate joint 120, an embodiment of implant 100 carrying bone graft material. In another example of step 314 implemented with step 316, a surgeon inserts, into each uncinate joint 120, an embodiment of implant 100 that has at least one void. This embodiment of implant 100 may include a porous portion, one or more fenestrations, and/or one or more cavities. Next, in this example, the surgeon loads bone graft material into the at least one void of implant 100.

In implementations of method 300 that do not utilize self-securing embodiments of implants 100, step 310 may further include a step 317 of securing implants 100 in uncinate joints 120. In one example of step 317, a surgeon secures each implant 100 to one or both of cervical vertebrae 184 and 186 using additional hardware, such as plates, screws, and/or pins.

In certain embodiments, step 310 includes a step 318 of monitoring locations of implants 100 and, optionally, equipment used to perform one, two, or all of steps 312, 314, and 317, to ensure that uncinate joints 120 are stabilized without unintentionally harming other structures. Step 318 may monitor the locations of implants 100, and optionally equipment used to handle implants 100, within patient 170 relative to the location of important structures such as vertebral arteries 230 (FIG. 2), nerve roots passing through the neural foramen (along paths 270 of FIG. 2), and spinal canal 260. In one example of step 318, real-time imaging of at least a portion of cervical spine segment 180 is performed concurrently with some or all of steps 312, 314, and 317. This real-time imaging may include fluoroscopy and/or other imaging method(s) known in the art.

Although not shown in FIG. 3, step 310 may be preceded by a step of locating uncinate joints 120, without departing from the scope hereof.

In one embodiment, method 300 further includes a step 320 of performing cervical discectomy. In one example of step 320, a surgeon removes at least the majority of intervertebral disc 150 from intervertebral disc space 140. Step 320 may utilize methods known in the art. Optionally, step 320 is followed by a step 330 that installs an intervertebral-disc-space (IVDS) implant in intervertebral disc space 140. In one implementation, step 330 includes a step 332 of loading bone graft material into intervertebral disc space 140, together with or into this IVDS implant, to promote subsequent fusion between cervical vertebrae 184 and 186 within intervertebral disc space 140. In one example of step 332, an IVDS implant, with at least one void capable of accommodating bone graft material, is inserted into intervertebral disc space 140. Bone graft material may be loaded into the void(s) prior to or after insertion of the IVDS implant into intervertebral disc space 140. In another example of step 332, the IVDS implant is a bag or malleable container with bone graft material.

In implementations of method 300 that include step 320 but do not utilize self-securing embodiments of implants 100 and also do not implement step 317, method 300 may further include a step 340, subsequent to step 320, of securing implants 100 in respective uncinate joints 120. Step 340 is, for example, performed in a manner similar to that of step 317.

Although for clarity not shown in FIG. 3, step 310 may utilize trial implants to stabilize uncinate joints 120, without departing from the scope hereof. Each such trial implant is an embodiment of implant 100, which is removed at a later stage. In one example, the trial implants are removed after step 320. When step 310 utilizes such trial implants, method 300 may include a later step of placing final implants 100 in uncinate joints 120. For example, method 300 may implement step 314 with final implants 100 after step 320 or during step 330.

Figure 4:
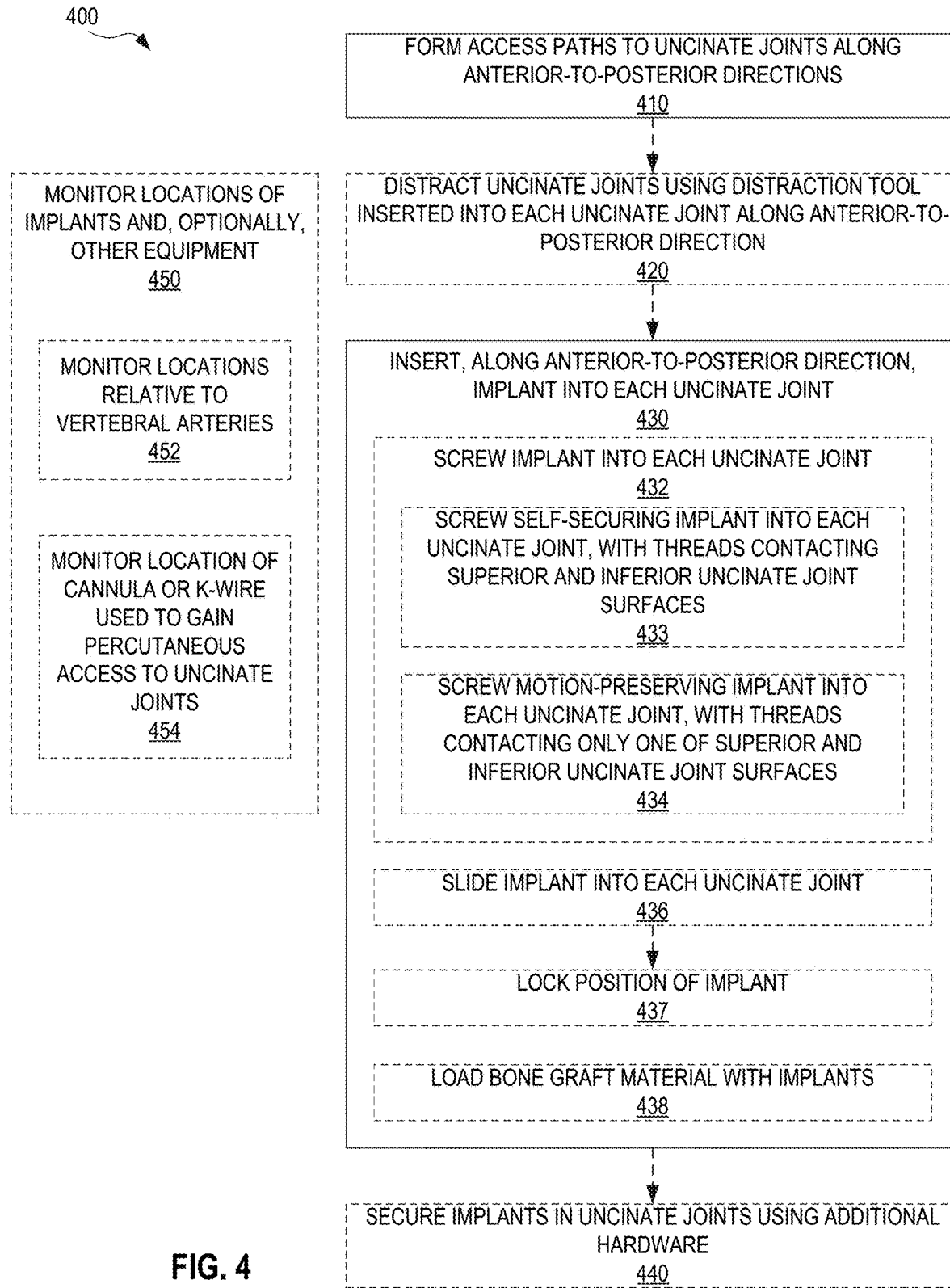
FIG. 4 illustrates a method for stabilizing the uncinate joints of a cervical spine segment, using access to the uncinate joints via anterior-to-posterior directions, according to an embodiment.

FIG. 4 illustrates one exemplary method 400 for stabilizing uncinate joints 120 (FIG. 1) of cervical spine segment 180, using access to uncinate joints 120 via anterior-to-posterior directions 210 (FIG. 2). Method 400 is an embodiment of step 310 of method 300 (FIG. 3) and may be performed percutaneously. Method 400 may be performed while leaving intervertebral disc 150 intact. In one implementation, method 400 facilitates fusion of uncinate joints 120. In another implementation, method 400 preserves motion of cervical spine segment 180. In yet another implementation, method 400 utilizes biodegradable implants that, after healing of an intervertebral disc injury, degrade and cease to play a role in the function of cervical spine segment 180.

In a step 410, an access path to each uncinate joint 120 is formed along a corresponding anterior-to-posterior direction 210, such that the access path is substantially in line with uncinate joint 120. In one example of step 410, for each uncinate joint 120, a guide wire is inserted into patient 170 along anterior-to-posterior direction 210. Herein, a "guide wire" refers to a wire that defines a direction and aids movement of tools and/or implants along this direction. A guide wire may refer to a Kirschner wire. The guide wire may be inserted to a depth of about 8-12 millimeters into uncinate joint 120. The guide wire may be threaded to cooperate with implants having a threaded cannulation. In another example of step 410, for each uncinate joint 120, a cannula is inserted into patient 170 along anterior-to-posterior direction 210. In yet another example, an access path is drilled along anterior-to-posterior direction 210, for example by implant 100 or a dedicated drill. Step 410 may utilize methods known in the art. For example, for each uncinate joint 120, a surgeon may use a robot or other device, mounted to patient 170 or mounted to a frame attached to patient 170, to align a guide wire with anterior-to-posterior direction 210, and then tapping the guide wire into patient 170 to reach uncinate joint 120. In one example, the access path goes through a longus colli muscle of patient 170.

In an optional step 420, each uncinate joint 120 is distracted using a distraction tool inserted into uncinate joint 120 along the corresponding access path formed in step 410. In one example of step 420, for each uncinate joint 120, a surgeon moves a cannulated distraction tool over a guide wire, placed in step 410, to reach uncinate joint 120, and then controls the distraction tool over the guide wire to distract uncinate joint 120. In another example of step 420, for each uncinate joint 120, a surgeon directs the distraction tool to uncinate joint 120 through a cannula, placed in step 410, to reach uncinate joint 120, and then controls the distraction tool through the cannula to distract uncinate joint 120. Alternatively, when method 400 is performed in open surgery, uncinate joints 120 may be distracted by distracting the superior and inferior vertebral bodies, for example using caspar pins.

In a step 430, for each uncinate joint 120, implant 100 is inserted into uncinate joint 120 using the access path formed in step 410. In one example of step 430, implants 100 are cannulated and, for each uncinate joint 120, a surgeon moves implant 100 over a guide wire to uncinate joint 120. In another example of step 430, for each uncinate joint 120, a surgeon moves implant 100 through a cannula to uncinate joint 120.

In certain implementations of method 400, compatible with both guide-wire insertion and through-cannula insertion of implants 100 into uncinate joints 120, each implant 100 includes threads and step 430 includes a step 432 of using the threads to screw implants 100 into place in uncinate joints 120. Such threaded embodiments of implants 100 are discussed below in reference to FIGS. 5A-8B, 13A-15, and 17A-18C. In one such implementation, step 432 includes a step 433 of screwing a self-securing and threaded embodiment of implant 100 into each uncinate joint 120, with the threads contacting both the superior surface and inferior surfaces of uncinate joint 120. The superior surface of uncinate joint 120 is that of superior cervical vertebra 184, and the inferior surface of uncinate joint 120 is that of inferior cervical vertebra 186. Exemplary implants compatible with step 433 are discussed below in reference to FIGS. 5A-8C. In another such implementation, step 432 includes a step 434 of screwing a motion-preserving embodiment of implant 100 into each uncinate joint 120, with the threads contacting only one of the superior surface and inferior surfaces of uncinate joint 120, while the other one of the superior surface and inferior surfaces of uncinate joint 120 is allowed to move relative to implant 100, at least during insertion of the implant into uncinate joint 120. Exemplary implants compatible with step 434 are discussed below in reference to FIGS. 13A-15 and 17A-D.

In another implementation of method 400, also compatible with both guide-wire insertion and through-cannula insertion of implants 100 into uncinate joints 120, step 430 includes a step 436 of sliding implants 100 into uncinate joints 120. Exemplary implants compatible with step 436 are discussed below in reference to FIGS. 9A-12B and 20A-21B. Optionally, step 436 is followed by a step 437, wherein, for each uncinate joint 120, a lock mechanism of each implant 100 is engaged to lock the position of implant 100 within uncinate joint 120. The lock may be engaged by rotating a portion of implant 100 to grip the surfaces of uncinate joint 120. Exemplary implants with such a lock mechanism are discussed below in reference to FIGS. 11A-12B. Alternatively, in step 437, all of implant 100 may be rotated to lock implant 100 in place in uncinate joint 120. An example of such an implant 100 is discussed below reference to FIGS. 20A-21B.

Optionally, step 430 includes a step 438 of loading bone graft material into each uncinate joint 120 together with, or into, the corresponding implant 100, to promote (a) fusion of uncinate joints 120 or (b) bony ingrowth in uncinate joints 120 at interfaces between implants 100 and one of cervical vertebrae 184 and 186. In one example of step 438, each implant 100 includes at least one void capable of accommodating bone graft material. Bone graft material may be loaded into the void(s) of each implant 100 before or after inserting implant 100 into uncinate joint 120. In another example of step 438, at least a portion of each implant 100 is a porous portion substantially composed of bone graft material. Since the surfaces of uncinate joints 120 are cortical bone, fusion promoted by step 438 may be stronger and/or faster than fusion within intervertebral disc space 140.

Without departing from the scope hereof, implant 100 and the distraction tool of step 420 may be integrated, or be the same. In this case, steps 420 and 430 may be performed concurrently. One example hereof is discussed below in reference to FIGS. 18A-19B. Another example implant capable of functioning as both distraction tool and implant is discussed below in reference to FIGS. 20A-21B.

In certain embodiments, method 400 includes a step 440 of securing each implant 100 to the corresponding uncinate joint 120 using additional hardware. In one example of step 440, a surgeon secures each implant 100 to both superior vertebra 184 and inferior vertebra 186 of cervical spine segment 180. In another example, a surgeon secures each implant 100 to only one of superior vertebra 184 and inferior vertebra 186 of cervical spine segment 180. Step 440 may be performed percutaneously. Exemplary implants compatible with step 440 are discussed in reference to FIGS. 9A-10B, 13A-15, and 17, for example.

In certain embodiments, method 400 includes a step 450 of monitoring the locations, within patient 170, of implants 100 and, optionally, other equipment used to perform one or more of steps 410-440. Step 450 may be performed during the execution of some or all of steps 410-440. Step 450 is an embodiment of step 318. In one embodiment, step 450 includes a step 452 of monitoring locations of implants 100, and optionally other equipment, relative to vertebral arteries 230 (FIG. 2). In implementations of method 400 based upon percutaneous access to uncinate joints 120, step 450 may include a step 454 of monitoring the locations of cannulae, guide wires, or other devices providing percutaneous access to uncinate joints 120.

Without departing from the scope hereof, method 400 may be performed independently for each of the two uncinate joints 120 of cervical spine segment 180.

FIGS. 5A and 5B illustrate one exemplary threaded implant 500 for stabilizing uncinate joint 120 (FIG. 1). Threaded implant 500 is an embodiment of implant 100 and may be implemented in method 400 as the self-securing implant of step 433. FIG. 5A shows threaded implant 500 in side elevation. FIG. 5B shows a cross sectional view of threaded implant 500, wherein the cross section is taken along line 5B-5B in FIG. 5A. FIGS. 5A and 5B are best viewed together.

Threaded implant 500 has length 580 and diameter 582. Length 580 is at least six millimeters, for example, to provide sufficient contact area between threaded implant 500 and surfaces of uncinate joint 120 that threaded implant 500 is capable of supporting the load of uncinate joint 120. Length 580 is at most eighteen millimeters, for example, to ensure that threaded implant 500 does not encroach the neural foramen. Diameter 582 may be in the range between two and seven millimeters, to produce a spacing, between superior and inferior surfaces of uncinate joint 120 when threaded implant 500 is inserted therein, which is sufficient to relieve impingement issues or pressure on intervertebral disc 150 (FIG. 1) while minimizing damage to uncinate joint 120 and allowing for percutaneous insertion of threaded implant 500. In one example, diameter 582 is such that threaded implant 500 may be inserted into uncinate joint 120 through a cannula.

Threaded implant 500 includes threads 510 along at least a portion of length 580. Threads 510 have pitch 588 and depth 584. Depth 584 is, for example, in the range between 0.5 and 1.2 millimeters. Pitch 588 is, for example, in the range between 0.5 and 2.0 millimeters. Optionally, depth 584 and/or pitch 588 changes along the length of threaded implant 500. In one such example, pitch 588 is in the range between 3 and 4 millimeters for the full extent of threads 510, but closer to leading end 520 (the end that first enters uncinate joint 120 when inserting threaded implant 500 therein) threads 510 include only one set of threads while, further from leading end 520, threads 510 include two sets of interlaced threads. Although not shown in FIGS. 5A and 5B, threaded implant 500 may include a non-threaded portion at the trailing end of threaded implant 500 (opposite leading end 520), without departing from the scope hereof.

In one implementation, leading end 520 of threaded implant 500 is tapered to ease insertion of threaded implant into uncinate joint 120. In another implementation, at least a portion of threaded implant, extending to leading end 520, is tapered as indicated by dashed lines 560 to ease insertion of threaded implant into uncinate joint 120. In this implementation, the taper angle 562 may be less than 15°, for example between 4° and 8°. Taper angle 562 may be configured to match the deviation from parallelism between cervical vertebrae 184 and 186 at uncinate joint 120, which stems from the lordosis of the cervical spine. Although FIG. 5A shows optional tapering (as indicated by dashed lines 560) as extending along the full length of threaded implant 500, threaded implant 500 may be tapered only along a portion of the length of threaded implant 500, without departing from the scope hereof. In one such example, a leading end of threaded implant 500 is tapered (as indicated by dashed lines 560) while a trailing end of threaded implant 500, adjacent the leading end of threaded implant 500, is not tapered.

In one embodiment, threaded implant 500 is cannulated with a through-hole 530 extending for the full length 580. Through-hole 530 has diameter 586. Diameter 586 may be in the range from 0.5 to 4 millimeters. In an exemplary use scenario, threaded implant 500 is threaded into uncinate joint 120 over a guide wire, wherein the guide wire is passing through through-hole 530.

Although not shown in FIGS. 5A and 5B, threaded implant 500 may include an interface at its trailing end, without departing from the scope hereof. This interface is configured to interface with a driver or drill, such that this driver or drill threads threaded implant 500 into place in uncinate joint 120.

In one embodiment, threaded implant 500 is substantially composed of a metal such as titanium, titanium alloy, stainless steel, cobalt, chromium, or a combination thereof. Without departing from the scope hereof, such metal embodiments of threaded implant 500 may include a coating, for example a hydroxyapatite coating, to achieve improved fixation of threaded implant 500 to uncinate joint 120. In another embodiment, threaded implant 500 includes a porous portion with pores capable of accommodating bone graft material, as discussed in reference to step 438 of method 400. In one example hereof, threaded implant 500 is substantially composed of, or includes, porous metal. In a related embodiment, at least a portion of threaded implant 500 is a porous portion substantially composed of bone graft material. In yet another embodiment, threaded implant 500 is substantially composed of allograft bone. In a further embodiment, threaded implant 500 is biodegradable or bioabsorbable and is composed, for example, of lactulose, proline, polyglycolic acid or a derivative thereof, poly-L-lactic acid or a derivative thereof, other biodegradable/bioabsorbable materials known in the art, or a combination thereof. In another embodiment, threaded implant 500 includes a polymer, such as polyetheretherketone (PEEK) or another polyaryletherketone (PAEK) polymer. Any of the above materials may be used in a 3-D printing process to make threaded implant 500.

FIG. 6A is a diagram 600 showing, in an anterior view, a pair of threaded implants 500 (FIGS. 5A and 5B) installed in uncinate joints 120 between cervical vertebrae 184 and 186 according to method 400. FIG. 6B is a close-up of diagram 600 showing one uncinate joint 120 with greater clarity. FIGS. 6A and 6B are best viewed together. When implemented in method 400, each threaded implant 500 is screwed into the corresponding uncinate joint 120 with threads 510 (not shown in FIGS. 6A and 6B) contacting both superior surface 684 and inferior surface 686 of uncinate joint 120. Threads 510 may grip superior surface 684 and inferior surface 686 and cooperate with a tension band to be self-securing in uncinate joint 120. Threaded implants 500 may be inserted into uncinate joints 120 while leaving intervertebral disc 150 intact. Method 400 may utilize optional through-hole 530 to insert threaded implant into uncinate joint 120 over a guide wire. Alternatively, or in combination therewith, method 400 may utilize optional through-hole 530 to carry or accept bone graft material used in step 438 of method 400.

FIGS. 7A and 7B illustrate one exemplary fenestrated, threaded implant 700 for stabilizing uncinate joint 120 (FIG. 1). Fenestrated, threaded implant 700 is an embodiment of threaded implant 500 (FIGS. 5A and 5B) and may be implemented in method 400 as the self-securing implant of step 432, as shown in FIGS. 6A and 6B. FIG. 7A shows fenestrated, threaded implant 700 in side elevation. FIG. 7B shows a cross section of fenestrated, threaded implant 700, wherein the cross section is taken along line 7B-7B in FIG. 7A. FIGS. 7A and 7B are best viewed together.

Fenestrated, threaded implant 700 is similar to threaded implant 500 as shown in FIGS. 5A and 5B, except for having fenestrations 720. Fenestrations 720 may serve to accommodate material displaced from uncinate joint 120 when fenestrated, threaded implant 700 is inserted therein. Fenestrations 720 may be particularly useful if using fenestrated, threaded implant 700 as the distraction tool in step 420 of method 400. Alternatively, or in combination therewith, fenestrations 720 may be cavities that carry bone graft material with the purpose of promoting fusion of uncinate joints 120. Furthermore, edges of fenestrations 720 may help secure fenestrated, threaded implant 700 in uncinate joint 120.

Although not shown in FIGS. 7A and 7B, fenestrations 720 may, at least in places, have depth sufficient to connect with through-hole 530 (if present), or fenestrations 720 may, at least in places, pass through fenestrated, threaded implant 700 from one side to another opposite side thereof, without departing from the scope hereof.

FIGS. 8A and 8B illustrate another exemplary fenestrated, threaded implant 800 for stabilizing uncinate joint 120 (FIG. 1). Fenestrated, threaded implant 800 is an embodiment of threaded implant 500 (FIGS. 5A and 5B) and may be implemented in method 400 (FIG. 4) as the self-securing implant of step 432, as shown in FIGS. 6A and 6B. FIG. 8A shows fenestrated, threaded implant 800 in side elevation. FIG. 8B shows a cross section of fenestrated, threaded implant 800, wherein the cross section is taken along line 8B-8B in FIG. 8A. FIGS. 8A and 8B are best viewed together.

Fenestrated, threaded implant 800 is similar to fenestrated, threaded implant 700 (FIGS. 7A and 7B), except for including cavities 830 in fenestrations 720. In one embodiment, at least some of cavities 830 are through-holes extending between fenestrations 720 located on opposite sides of fenestrated, threaded implant 800. In another embodiment, each cavity 830 is an separate pocket in fenestrated, threaded implant 800, which does not connect with other cavities 830 or with through-hole 530 (if present). In this embodiment, cavities 830 may serve to accommodate bone graft material loaded into cavities 830 prior to insertion of fenestrated, threaded implant 800 into uncinate joint 120. Thus, this embodiment of fenestrated, threaded implant 800 is compatible with embodiments of method 400 that include steps 432 and 438. In yet another embodiment, cavities 830 coexist with through-hole 530, and at least some of cavities 830 have depth sufficient to reach through-hole 530. In this embodiment, a surgeon may load bone graft material into through-hole 530, from anterior side 202, after placing fenestrated, threaded implant 800 in uncinate joint 120, whereafter the bone graft material is allowed to contact surfaces of uncinate joint 120 via cavities 830. Thus, this embodiment of fenestrated, threaded implant 800 is compatible with embodiments of method 400 that include steps 432 and 438.

FIG. 8C illustrates a cap 880 for sealing through-hole 530 of fenestrated, threaded implant 800 at the trailing end thereof. The trailing end of fenestrated, threaded implant 800 is the end opposite optionally tapered leading end 520. The trailing end is associated with a surface 802. Cap 880 may serve, for example in step 438, to seal the trailing-end portion of through-hole 530 after loading bone graft material into through-hole 530, to prevent bone graft material from leaking out of the trailing end of through-hole 530. In one implementation of method 400, sealing of through-hole 530 at leading end 520 is unnecessary since tissue of patient 170 provides resistance against bone graft material leaking out through through-hole 530 at leading end 520.

Cap 880 includes a cylindrical member 882 that fits in through-hole 530. Although not shown in FIGS. 8A-C, and without departing from the scope hereof, cylindrical member 882 and at least a portion of through-hole 530 may be threaded, such that a surgeon may screw cap 880 into through-hole 530. In one embodiment, cap 880 includes a larger-diameter element 884 with a surface 886 facing cylindrical member 882. In this embodiment, surface 886 of cap 880 faces surface 802 of fenestrated, threaded implant 800 when inserting cap 880 into through-hole 530. A surgeon may insert cap 880 into through-hole 530 to a depth determined by contact between surfaces 802 and 886.

In one implementation, cap 880 includes a recess 888 having shape matching that of a tool, for example a phillips-head screwdriver/drill or a star-head screwdriver/drill. A surgeon may insert such a tool into recess 888 to guide, and optionally screw, cylindrical member 882 into through-hole 530. In another embodiment, larger-diameter element 884 is shaped to at least partly fit within a tool, such as a hexagonal wrench, thus allowing a surgeon to use a tool to grab onto larger-diameter element 884 to guide, and optionally screw, cylindrical member 882 into through-hole 530.

FIG. 8D illustrates, in side elevation from direction opposite cylindrical member 882 and mounted in through-hole 530 of fenestrated, threaded implant 800, one exemplary cap 880' which is an implementation of cap 880 that further implements a locking lever. In cap 880', larger-diameter element 884 is implemented as an oblong element 884'. For example, oblong element 884' is oval, rectangular, or rectangular with rounded corners. The longer dimension of oblong element 884' extends beyond fenestrated, threaded implant 800 by a distance 850, while the shorter dimension of oblong element 884' has extent no greater than that of fenestrated, threaded implant 800. Optionally, at least a portion of oblong element 884' extending beyond fenestrated, threaded implant 800 includes a jagged surface 883. Jagged surface 883 is configured to grip a surface of uncinate joint 120 to at least participate in securing fenestrated, threaded implant 800 in uncinate joint 120. Without departing from the scope hereof, oblong element 884' may extend beyond fenestrated, threaded implant 800 in only one direction as opposed to the two directions shown in FIG. 8D.

In one embodiment, cylindrical member 882 of cap 880' is sized for pressure fit into through-hole 530. Tissue of patient 170 prevents fenestrated, threaded implant 800 from migrating in any other direction than back out in the posterior-to-anterior direction. Cap 880', when secured to uncinate joint 120, prevents fenestrated, threaded implant 800 from migrating in the posterior-to-anterior direction, such that cap 880' locks fenestrated, threaded implant 800 in uncinate joint 120. In an exemplary use scenario, cap 880' is inserted into through-hole 530 (either prior to or after insertion of fenestrated, threaded implant 800 into uncinate joint 120) with cap 880' aligned such that the longer dimension of oblong element 884' does not interfere with surfaces of uncinate joint 120. After insertion of cap 880' into through-hole 530, cap 880' is rotated about the axis of through-hole 530, for example by about 45 to about 135 degrees, to secure cap 880' to one or two surfaces of uncinate joint 120. Optionally, each surface of uncinate joint 120 to which cap 880' is secured is prepared, for example by a high-speed drill, to form a recess for accommodating cap 880'.

Figure 8E:
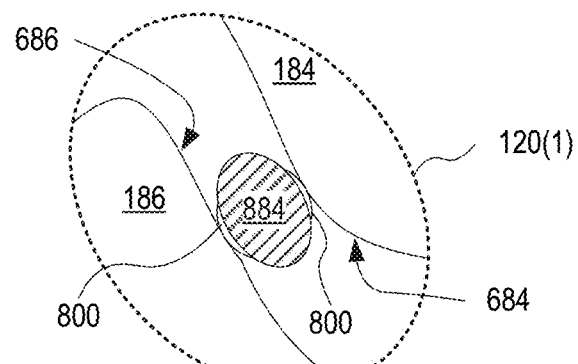
FIGS. 8E and 8F show, in an anterior view, the fenestrated, threaded implant of FIGS. 8A and 8B with the cap of FIG. 8D installed in uncinate joint 120, according to an embodiment.
Figure 8F:
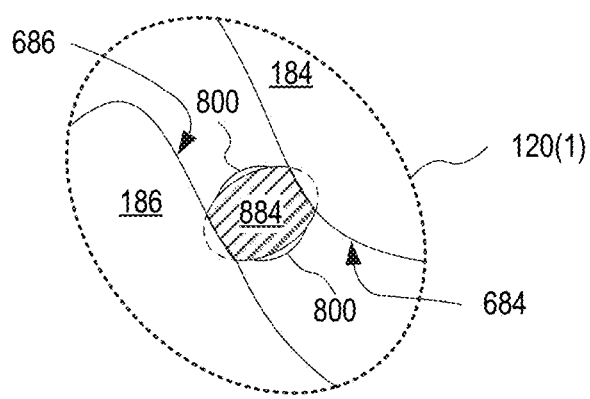

FIGS. 8E and 8F show, in an anterior view, fenestrated, threaded implant 800 (FIGS. 8A and 8B) with cap 880' (FIG. 8D) in uncinate joint 120, when installed in uncinate joint 120 according to method 400 (FIG. 4). FIGS. 8E and 8F are best viewed together. In FIG. 8E, cap 880' is in its unlocked configuration, after step 436 and before step 437 of method 400. In this configuration, fenestrated, threaded implant 800 contacts superior surface 684 (FIG. 6B) and inferior surface 686, respectively, but oblong member 884' does not grip either of superior surface 684 and inferior surface 686. In FIG. 8F, cap 880' is in its locked configuration, after step 437 of method 400. In this configuration, at least a portion of oblong member 884' is embedded into each of superior surface 684 and inferior surface 686, thus locking the position of fenestrated, threaded implant 800 in uncinate joint 120.

Figure 9A:
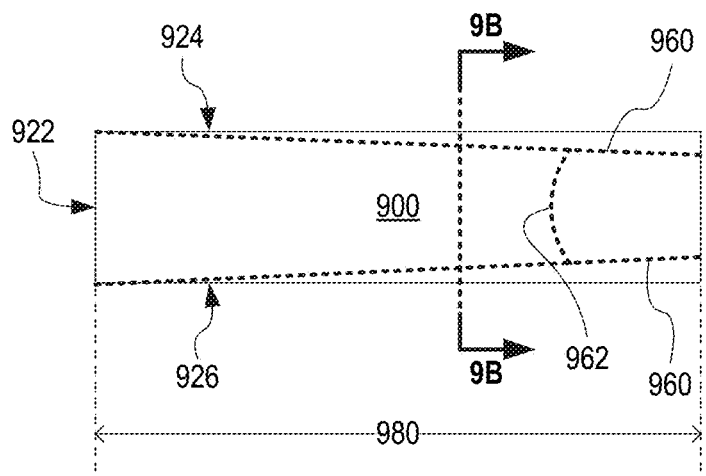
FIGS. 9A and 9B illustrate a shim implant for stabilizing an uncinate joint, according to an embodiment.
Figure 9B:
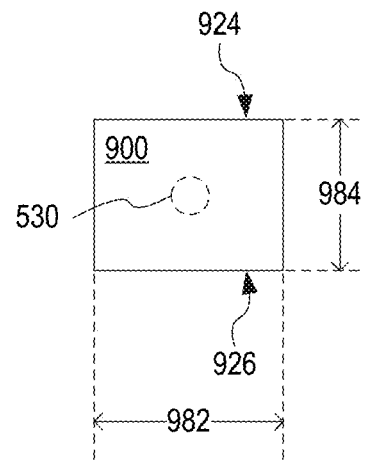

FIGS. 9A and 9B illustrate one exemplary shim implant 900 for stabilizing uncinate joint 120 (FIG. 1). Shim implant 900 is an embodiment of implant 100 and may be implemented in method 400 as the implant of step 436. FIG. 9A shows shim implant 900 in side elevation. FIG. 9B shows a cross section of shim implant 900, wherein the cross section is taken along line 9B-9B in FIG. 9A. FIGS. 9A and 9B are best viewed together.

Shim implant 900 has length 980, width 982, and height 984. Length 980 is at least six millimeters, for example, to provide sufficient contact area, between shim implant 900 and surfaces of uncinate joint 120, that shim implant 900 is capable of supporting the load of uncinate joint 120. Length 980 is at most eighteen millimeters, for example, to ensure that shim implant 900 does not encroach the neural foramen. Width 982 may be in the range between two and seven millimeters to provide sufficient contact area, between shim implant 900 and surfaces of uncinate joint 120, while minimizing lateral displacement of intervertebral disc 150 (FIG. 1). Height 984 may be in the range between two and seven millimeters, to produce a spacing, between superior and inferior surfaces of uncinate joint 120 when shim implant 900 is inserted therein, which is sufficient to relieve impingement issues or pressure on intervertebral disc 150 (FIG. 1), while minimizing damage to uncinate joint 120 and allowing for percutaneous insertion of shim implant 900.

Shim implant 900 has surfaces 924 and 926 configured to contact the superior surface and the inferior surface, respectively, of uncinate joint 120. Shim implant 900 also has a surface 922 configured to be the trailing surface of shim implant 900, when inserting shim implant 900 into uncinate joint 120 according to method 400. Without departing from the scope hereof, surfaces 924 and 926, as well as other surfaces of shim implant 900 may be non-planar. For example, shim implant 900 may be tapered, as indicated by dashed lines 960, with a taper angle 962. Taper angle 962 may be less than 15°, for example between 4° and 8°. Taper angle 962 may be configured to match the deviation from parallelism between cervical vertebrae 184 and 186 at uncinate joint 120, which stems from the lordosis of the cervical spine.

Optionally, shim implant 900 is cannulated with through-hole 530 extending for the full length 980, such that shim implant 900 may be inserted into uncinate joint 120 over a guide wire.

In one embodiment, shim implant 900 is substantially composed of a metal such as titanium, titanium alloy, stainless steel, cobalt, chromium, or a combination thereof. Without departing from the scope hereof, such metal embodiments of shim implant 900 may include a coating, for example a hydroxyapatite coating, on surfaces 924 and 926 to achieve improved fixation of shim implant 900 to uncinate joint 120. In another embodiment, shim implant 900 includes a porous portion with pores that may carry bone graft material to uncinate joint 120, as discussed in reference to step 438 of method 400. In one example, surfaces 924 and 926 are porous. In another example, shim implant 900 is substantially composed of, or includes, porous metal. In a similar embodiment, this porous portion is substantially composed of bone graft material that promotes bone growth in the pores thereof. In yet another embodiment, shim implant 900 is substantially composed of allograft bone. In a further embodiment, shim implant 900 includes a polymer. The polymer is, for example, polyetheretherketone (PEEK) or another polyaryletherketone (PAEK) polymer. In a further embodiment, shim implant 900 is biodegradable or bioabsorbable and is composed, for example, of lactulose, proline, polyglycolic acid or a derivative thereof, poly-L-lactic acid or a derivative thereof, other biodegradable/bioabsorbable materials known in the art, or a combination thereof. Any of the above materials may be used in a 3-D printing process to make shim implant 900.

Although not shown in FIGS. 9A and 9B, shim implant 900 may include hollow portions and associated openings in the surfaces of shim implant 900, without departing from the scope hereof. Such hollow portions may accommodate bone graft material, as discussed in reference to step 438 of method 400.

Figure 10A:
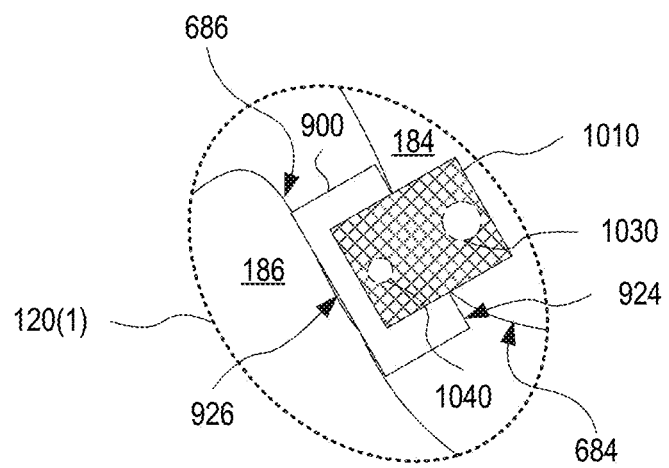
FIGS. 10A and 10B illustrate, in an anterior view, the shim implant of FIGS. 9A and 9B secured to an uncinate joint using additional hardware, according to an embodiment.
Figure 10B:
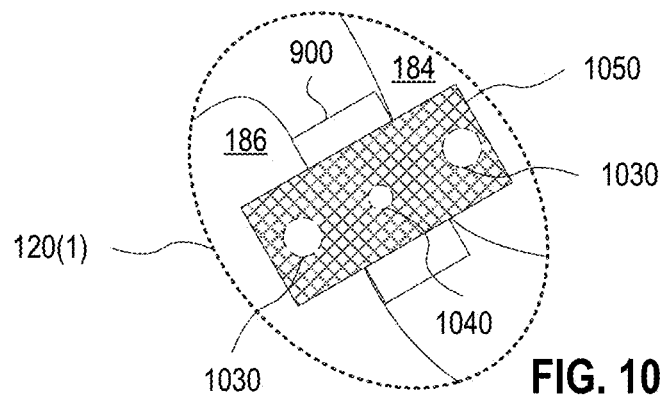

FIGS. 10A and 10B illustrate, in an anterior view, shim implant 900 (FIGS. 9A and 9B) secured to uncinate joint 120

(FIG. 1) using exemplary additional hardware, as discussed in reference to step 440 of method 400 (FIG. 4). Shim implant 900 is placed in uncinate joint 120 with surfaces 924 and 926 contacting superior surface 684 (FIG. 6B) and inferior surface 686, respectively, of uncinate joint 120, and with surface 922 facing anterior side 202 (FIG. 2).

In FIG. 10A, shim implant 900 is secured to superior cervical vertebra 184 by affixing a bracket 1010 to shim implant 900 and superior cervical vertebra 184. Bracket 1010 may be affixed to shim implant 900 and superior cervical vertebra 184 by fasteners 1040 and 1030, respectively. Fastener 1030 is, for example, a screw or a pin. Fastener 1040 is, for example, a screw or a bolt. In one example, fastener 1040 is configured to attach to through-hole 530. Through-hole 530 may be threaded. In the implementation shown in FIG. 10A, surface 926 may be configured to allow relative movement between inferior surface 686 and surface 926, such that shim implant 900 is motion-preserving. Alternatively, surface 926 is textured to grip inferior surface 686, thus fixing inferior surface 686 with respect to superior surface 684.

In one example of the implementation shown in FIG. 10A, shim implant 900 includes voids at the interface with superior cervical vertebra 184. These voids are capable of accommodating bone graft material to promote bony ingrowth at this interface. The voids may be connected with through-hole 530, such that bone graft material may be loaded into the voids via through-hole 530 from anterior side 202 when shim implant 900 is located in uncinate joint 120. Fastener 1040, optionally in cooperation with bracket 1010, may function as a cap for sealing through-hole 530, to prevent leakage of bone graft material out of the trailing end of through-hole 530.

Without departing from the scope hereof, shim implant 900 may be mounted via bracket 1010 to inferior cervical vertebra 186 instead of superior cervical vertebra 184. Additionally, bracket 1010 may have shape different from that shown in FIG. 10A.

In FIG. 10B, shim implant 900 is secured to both superior cervical vertebra 184 and inferior cervical vertebra 186 by affixing a bracket 1050 to shim implant 900, superior cervical vertebra 184, and inferior cervical vertebra 186. Bracket 1050 may be affixed to shim implant 900, superior cervical vertebra 184, and inferior cervical vertebra 186 by fasteners 1040, 1030, and 1030, respectively, as discussed above in reference to FIG. 10A.

In one example of the implementation shown in FIG. 10B, shim implant 900 includes voids, at least at the interfaces with cervical vertebrae 184 and 186. These voids are capable of accommodating bone graft material to promote fusion of uncinate joint 120. The voids may be connected with through-hole 530, such that bone graft material may be loaded into the voids via through-hole 530 from anterior side 202 when shim implant 900 is located in uncinate joint 120. Fastener 1040, optionally in cooperation with bracket 1050, may function as a cap for sealing through-hole 530, to prevent leakage of bone graft material out of through-hole 530, as discussed in reference to FIG. 8C.

Figure 11A:
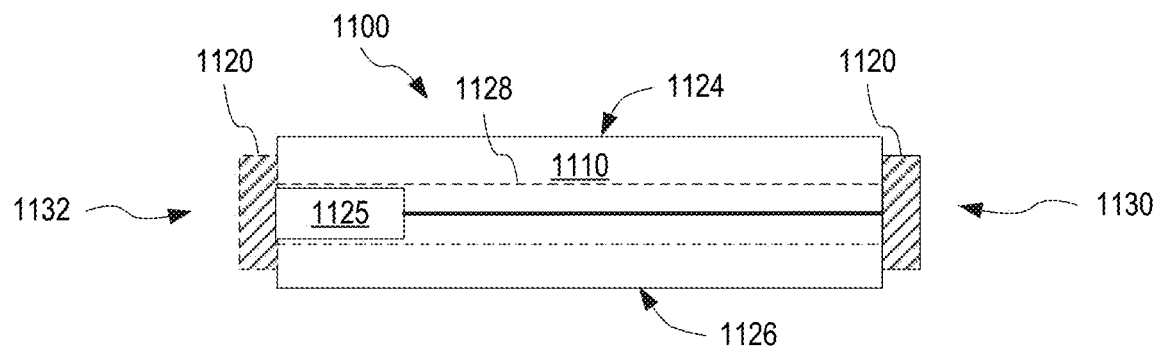
FIGS. 11A, 11B, 11C, 11D and 11E illustrate a locking implant for stabilizing uncinate joint 120, according to an embodiment.
Figure 11B:
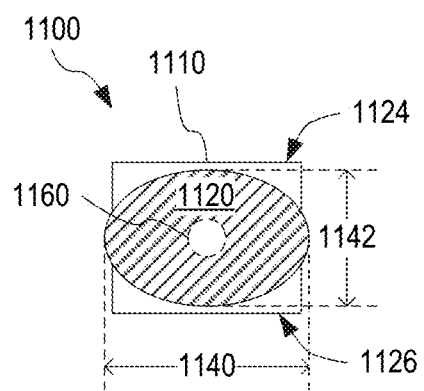
Figure 11C:
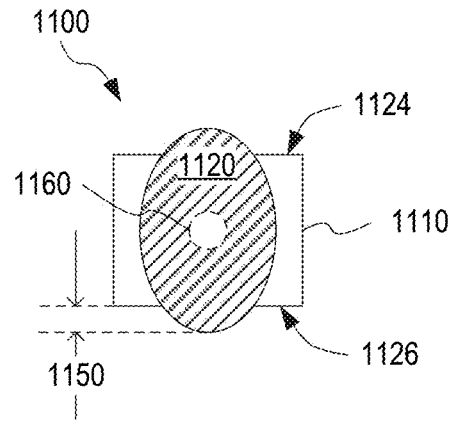

FIGS. 11A, 11B, and 11C illustrate one exemplary locking implant 1100 for stabilizing uncinate joint 120 (FIG. 1). Locking implant 1100 is an embodiment of implant 100 and may be implemented in method 400 (FIG. 4) as the implant of steps 436 and 437. FIG. 11A shows locking implant 1100 in side elevation. FIGS. 11B and 11C show a front elevation view of leading end 1130 of locking implant 1100, wherein leading end 1130 is the end of locking implant 1100 that first enters uncinate joint 120 when inserting locking implant 1100 into uncinate joint 120 according to method 400. In FIGS. 11A and 11B, locking implant 1100 is in its unlocked configuration. In FIG. 11C, locking implant 1100 is in its locked configuration. FIGS. 11A, 11B, and 11C are best viewed together.

Locking implant 1100 includes a body 1110 that is similar to shim implant 900 (FIG. 9). Body 1110 may be tapered as discussed in reference to shim implant 900. Body 1110 has surfaces 1124 and 1126 configured to face superior surface 684 (FIG. 6B) and inferior surface 686, respectively, of uncinate joint 120, when locking implant 1100 is placed in uncinate joint 120. At leading end 1130, locking implant 1100 further includes a locking lever 1120 attached to body 1110.

Locking implant 1100 has a longer dimension 1140 and a shorter dimension 1142. Shorter dimension 1142 is such that, when locking implant 1100 is in its unlocked configuration (see FIG. 11B), locking lever 1120 does not extend beyond surfaces 1124 and 1126. Longer dimension 1140 is such that, when locking implant 1100 is in its locked configuration (see FIG. 11C), locking lever 1120 extends beyond each of surfaces 1124 and 1126 by a distance 1150. Distance 1150 is, for example, in the range between 0.2 and 1.0 millimeters. The cross section of locking lever 1120 may be oval (as shown in FIGS. 11B and 11C), rectangular, or otherwise elongated to meet these requirements to longer dimension 1140 and shorter dimension 1142. Locking implant 1100 includes a rotation mechanism 1125 coupled with locking lever 1120. Rotation mechanism 1125 is accessible from trailing end 1132 of locking implant 1100. When actuated, rotation mechanism 1125 rotates locking lever 1120, for example from its unlocked position (FIG. 11B) to its locked position (FIG. 11C).

In one embodiment, locking implant 1100 is cannulated with a through-hole 1160 extending from leading end 1130 to trailing end 1132. Method 400 may utilize through-hole 1160 to insert locking implant 1100 into uncinate joint 120 over a guide wire, as discussed in reference to FIG. 4.

Rotation mechanism 1125 may be implemented in a shaft 1128 rigidly coupled to locking lever 1120. Shaft 1128 may implement rotation mechanism 1125 as a receptacle for a driver, such that rotation of the driver, when engaged with the receptacle, results in rotation of locking lever 1120. The receptacle may be male or female or a combination thereof. Shaft 1128 may implement a portion of through-hole 1160.

Optionally, locking implant 1100 includes two or more locking levers 1120. In one example, a second locking lever 1120 is located at trailing end 1132. Rotation mechanism 1125 may be coupled with all locking levers 1120 of locking implant 1100 to simultaneously rotate all locking levers 1120. In embodiments including two or more locking levers 1120, all locking levers 1120 may be rigidly interconnected (for example via shaft 1128) and rotation mechanism 1125 may be integrated in one of locking levers 1120 as a receptacle for a driver, such that the driver, when acting on rotation mechanism 1125, rotates all locking levers 1120 in the same manner. The receptacle may be male or female or a combination thereof.

Without departing from the scope hereof, locking implant 1100 may include a locking lever 1120 only at trailing end 1132. In such an embodiment, rotation mechanism 1125 may be integrated in locking lever 1120 as a receptacle for a driver. The receptacle may be male or female or a combination thereof.

In one embodiment, locking implant 1100 is substantially composed of a metal such as titanium, titanium alloy, stainless steel, cobalt, chromium, or a combination thereof.

Without departing from the scope hereof, such metal embodiments of locking implant 1100 may include a coating, for example a hydroxyapatite coating, on surfaces 1124 and 1126 and/or on locking lever(s) 1120 to achieve improved fixation of locking implant 1100 to uncinate joint 120. In another embodiment, locking implant 1100 includes a porous portion with pores that may carry bone graft material to uncinate joint 120, as discussed in reference to step 438 of method 400. For example, surfaces 1124 and 1126, or all of body 1110, may be porous. Surfaces 1124 and 1126, or all of body 1110, may be porous metal. In a similar embodiment, the porous portion is substantially composed of bone graft material that promotes bone growth in the pores thereof. In yet another embodiment, body 1110 is substantially composed of allograft bone. Although not shown in FIGS. 11A, 11B, and 11C, body 1110 may include hollow portions and associated openings in the surfaces of body 1110, without departing from the scope hereof. Such hollow portions may carry bone graft material, as discussed in reference to step 438 of method 400. In a further embodiment, locking implant 1100 is biodegradable or bioabsorbable and is composed, for example, of lactulose, proline, polyglycolic acid or a derivative thereof, poly-L-lactic acid or a derivative thereof, other biodegradable/bioabsorbable materials known in the art, or a combination thereof. Any of the above materials may be used in a 3-D printing process to make body 1110.

Figure 11D:
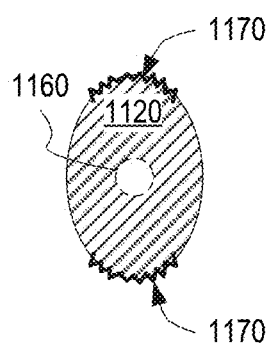

FIG. 11D illustrates one exemplary implementation of locking lever 1120 that includes a jagged surface 1170 on at least on a portion of locking lever 1120 configured to contact superior surface 684 and inferior surface 686.

Figure 11E:
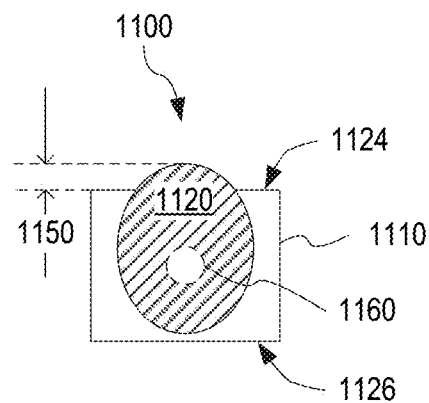

FIG. 11E illustrates another exemplary implementation of locking lever 1120, wherein locking lever extends beyond only one of surfaces 1124 and 1126 when in locked position. In this implementation, locking implant 1100 is configured such that locking lever 1120 contacts only one of superior surface 684 and inferior surface 686. Although not shown in FIG. 11E, the portion of locking lever 1120, which is configured to contact one of superior surface 684 and inferior surface 686, may be jagged as shown in FIG. 11D.

Figure 12A:
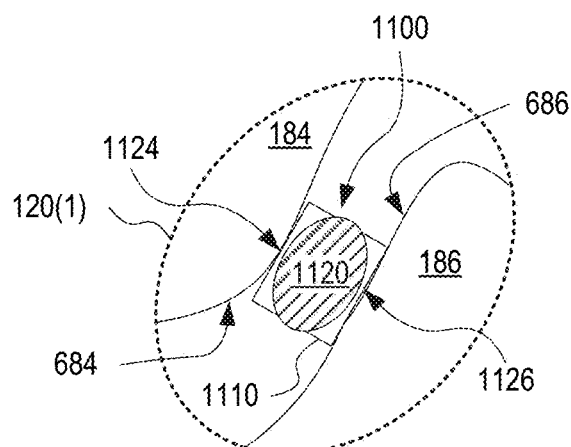
FIGS. 12A and 12B show, in a posterior view, the locking implant of FIGS. 11A-E) installed in an uncinate joint, according to an embodiment.
Figure 12B:
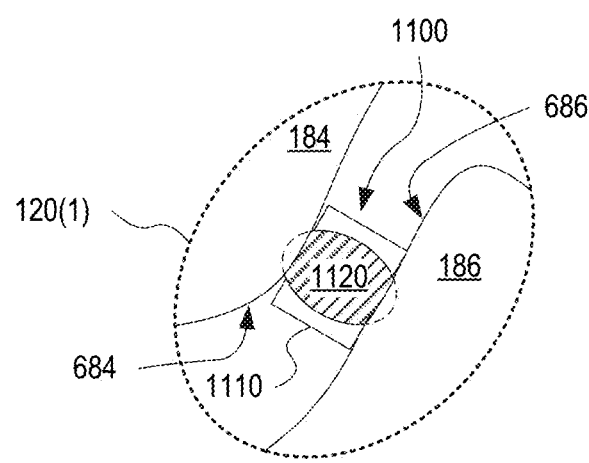

FIGS. 12A and 12B show, in a posterior view, locking implant 1100 (FIGS. 11A-E) in uncinate joint 120, when installed in uncinate joint 120 according to method 400 (FIG. 4). FIGS. 12A and 12B are best viewed together. In FIG. 12A, locking implant 1100 is in its unlocked configuration, after step 436 and before step 437 of method 400. In this configuration, surfaces 1124 and 1126 contact superior surface 684 (FIG. 6B) and inferior surface 686, respectively, but locking lever 1120 does not contact either of superior surface 684 and inferior surface 686. In FIG. 12B, locking implant 1100 is in its locked configuration, after step 437 of method 400. In this configuration, at least a portion of locking lever 1120 is embedded into each of superior surface 684 and inferior surface 686, thus locking the position of locking implant 1100 in uncinate joint 120.

FIGS. 13A, 13B, 13C, and 13D illustrate one exemplary motion-preserving implant 1300 for stabilizing uncinate joint 120 (FIG. 1). Motion-preserving implant 1300 is an embodiment of implant 100 and may be implemented in method 400 as the implant of step 434. FIG. 13A shows motion-preserving implant 1300 in side elevation. FIG. 13B shows motion-preserving implant 1300 in cross-sectional view, wherein the cross section is taken along line 13B-13B in FIG. 13A. FIG. 13C shows leading end 1330 of motion-preserving implant 1300 in elevation view, while FIG. 13D shows trailing end 1332 of motion-preserving implant 1300 in elevation view. Leading end 1330 is the end that first enters uncinate joint 120 when inserting motion-preserving implant 1300 into uncinate joint 120 according to method 400. FIGS. 13A-D are best viewed together.

Motion-preserving implant 1300 includes a screw 1310 with threads 1312. Threads 1312 may be similar to threads 510 (FIG. 5). Motion-preserving implant 1300 further includes a housing 1320 that partly contains screw 1310. Screw 1310 protrudes, by a distance 1386, through an opening 1324 of housing 1320, such that threads 1312 may contact a surface of uncinate joint 120. Distance 1386 is, for example, around one millimeter or a fraction of a millimeter. Distance 1386 may be such that housing 1320 contacts the surface of uncinate joint 120. Housing 1320 includes a surface 1322 that is able to slide on a surface of uncinate joint 120. In one example, surface 1322 is smooth. Surface 1322 may be curved to accommodate a variety of angles between surface 1322 and a surface of uncinate joint 120 in contact with surface 1322. Surface 1322 generally faces away from opening 1324. Motion-preserving implant 1300 further includes a rotation mechanism 1315 that, when actuated, rotates screw 1310. Rotation mechanism 1315 may be accessible from trailing end 1332. In one embodiment, rotation mechanism 1315 is a recess configured to accept a driver or drill, for example a hex driver or drill, such that this driver or drill may rotate screw 1310.

Motion-preserving implant 1300 has length 1380, width 1382, and height 1384, which may be similar to length 980, width 982, and height 984 of shim implant 900 (FIGS. 9A and 9B).

Optionally, motion-preserving implant 1300 is cannulated with a through-hole 1360 extending from leading end 1330 to trailing end 1332. Method 400 may utilize through-hole 1360 to insert motion-preserving implant 1300 into uncinate joint 120 over a guide wire, as discussed in reference to FIG. 4. Through-hole 1360 is centered relative to the cross section of screw 1310, such that screw 1310 may rotate while motion-preserving implant 1300 is placed over a guide wire.

Screw 1310 may be of similar material and/or structural composition as threaded implant 500 (FIGS. 5A and 5B). Housing 1320 may be of similar material and/or structural composition as shim implant 900.

Without departing from the scope hereof, housing 1320 may be tapered. In one example, housing 1320 is tapered, as indicated by dashed line 1370, with a taper angle 1372. Taper angle 1372 may be less than 15°, for example between 4° and 8°. Taper angle 1372 may be configured to match the deviation from parallelism between cervical vertebrae 184 and 186 at uncinate joint 120, which stems from the lordosis of the cervical spine. In another example, housing 1320 is curved and tapered, such that curved surface 1322 has orientation generally along dashed line 1370.

Figure 14A:
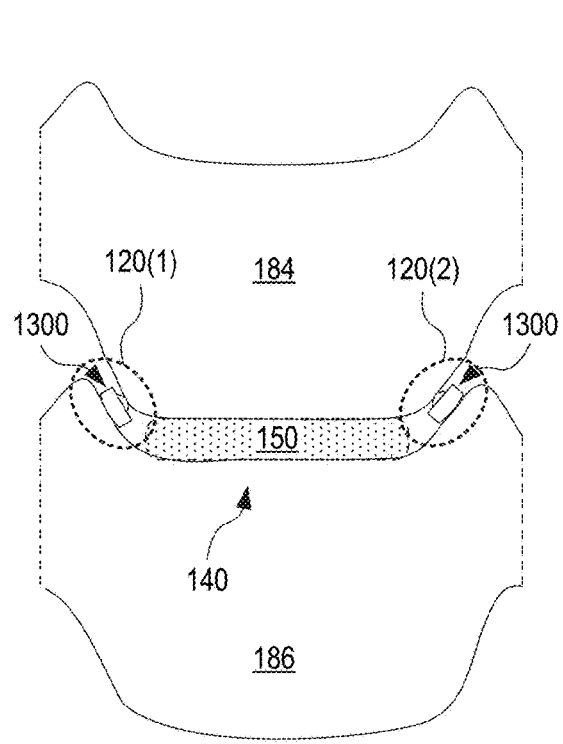
FIGS. 14A and 14B show, in an anterior view, a pair of the motion-preserving implant of FIGS. 13A-D installed in the uncinate joints of a cervical spine segment according to the method of FIG. 4, according to an embodiment.
Figure 14B:
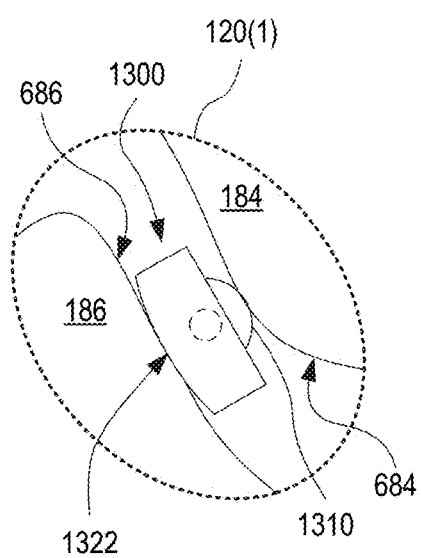

FIG. 14A shows, in an anterior view, a pair of motion-preserving implants 1300 (FIGS. 13A-D) installed in uncinate joints 120 according to method 400 (FIG. 4). FIG. 14B is a close-up of FIG. 14A showing one uncinate joint 120 in further detail. FIGS. 14A and 14B are best viewed together.

When inserting motion-preserving implant 1300 into corresponding uncinate joint 120, in step 434 of method 400, motion-preserving implant 1300 is oriented such that screw 1310 contacts superior surface 684 (FIG. 6B), while surface 1322 contacts inferior surface 686. A surgeon rotates screw 1310 using rotation mechanism 1315 (for clarity not shown in FIGS. 14A and 14B). Since screw 1310 contacts superior surface 684, this rotation screws motion-preserving implant 1300 into uncinate joint 120. Surface 1322 contacts inferior surface 686 while allowing relative movement between motion-preserving implant 1300 and inferior surface 686.

Figure 15:
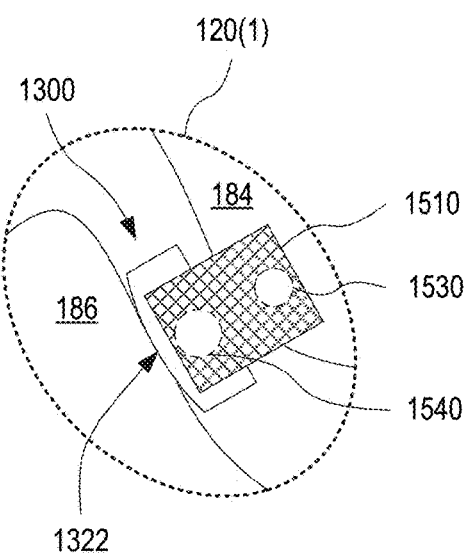
FIG. 15 shows, in an anterior view, the motion-preserving implant of FIGS. 13A-D secured to an uncinate joint using additional hardware, according to an embodiment.

FIG. 15 shows, in an anterior view, motion-preserving implant 1300 (FIGS. 13A-D) secured to uncinate joint 120 (FIG. 1) using exemplary additional hardware, as discussed in reference to step 440 of method 400 (FIG. 4). Motion-preserving implant 1300 is located in uncinate joint 120 with screw 1310 contacting and gripping superior surface 684 (FIG. 6B). Motion-preserving implant 1300 is secured to superior cervical vertebra 184 by affixing a bracket 1510 to motion-preserving implant 1300 and superior cervical vertebra 184. Bracket 1510 may be affixed to motion-preserving implant 1300 and superior cervical vertebra 184 by fasteners 1540 and 1530, respectively. Fastener 1530 is, for example, a screw or a pin. Fastener 1540 is, for example, a screw or a bolt. In one example, fastener 1540 is configured to attach to through-hole 1360. Without departing from the scope hereof, bracket 1510 may have shape different from that shown in FIG. 15.

FIGS. 16A, 16B, 16C, and 16D illustrate one exemplary bracket 1600 for securing two implants 100, located in uncinate joints 120 of cervical spine segment 180 (FIG. 1), to one vertebra of cervical spine segment 180. Bracket 1600 is common to both implants 100. FIGS. 16A-D show a scenario, wherein bracket 1600 secures a pair of motion-preserving implants 1300 (FIGS. 13A-D) to cervical spine segment 180. However, bracket 1600 may be applied to other embodiments of implant 100, such as shim implant 900 (FIGS. 9A and 9B) and screw-in implant 1700 discussed below in reference to FIGS. 17A-D. Method 400 (FIG. 4) may implement bracket 1600 in step 440.

Figure 16A:
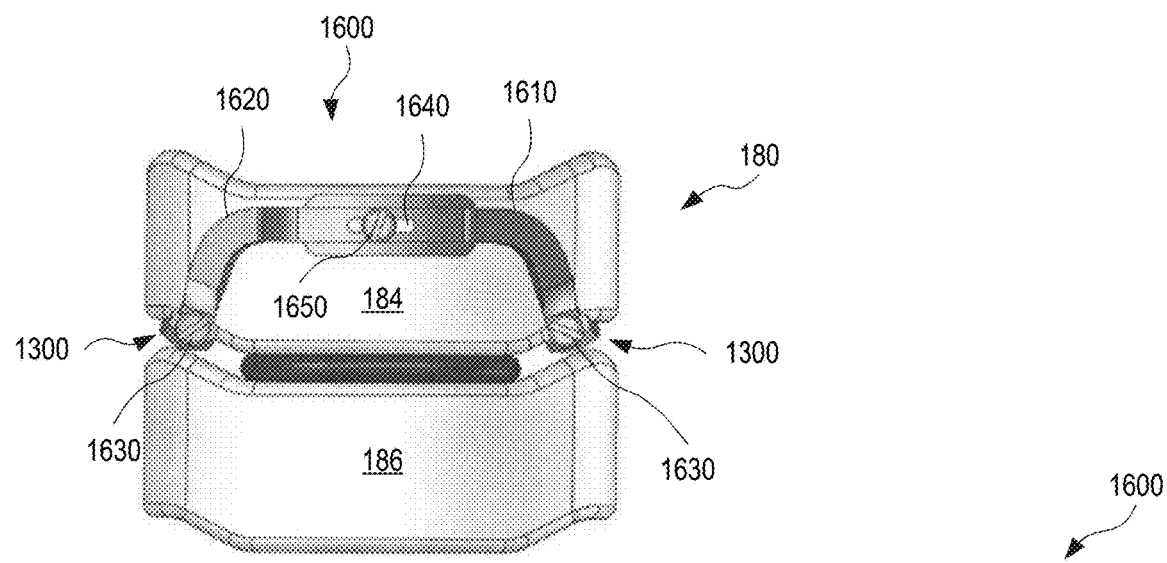
FIGS. 16A, 16B, 16C, and 16D illustrate a bracket for securing two implants, located in the uncinate joints of a cervical spine segment, to one vertebra of the cervical spine segment, according to an embodiment.
Figure 16B:
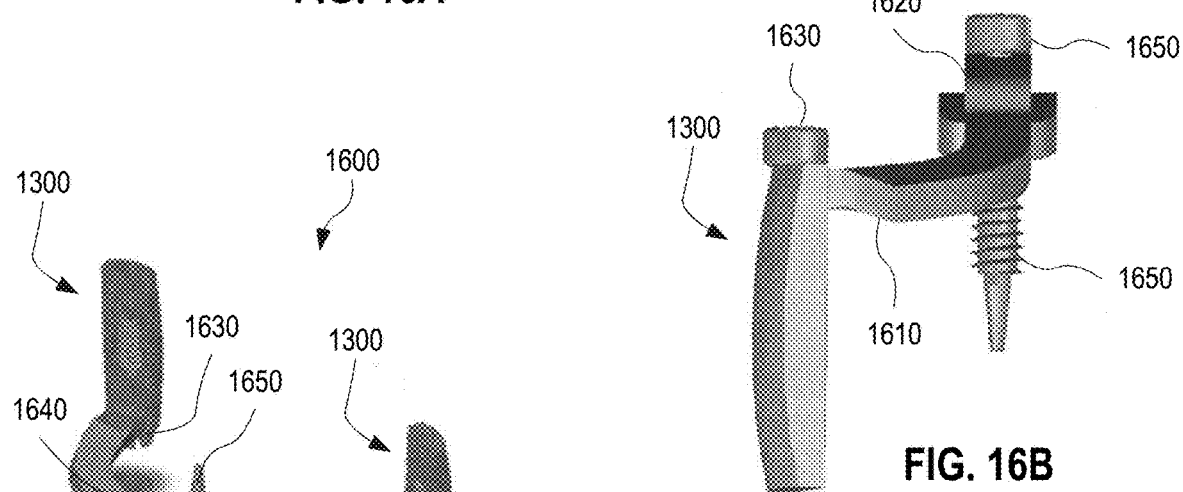
Figure 16C:
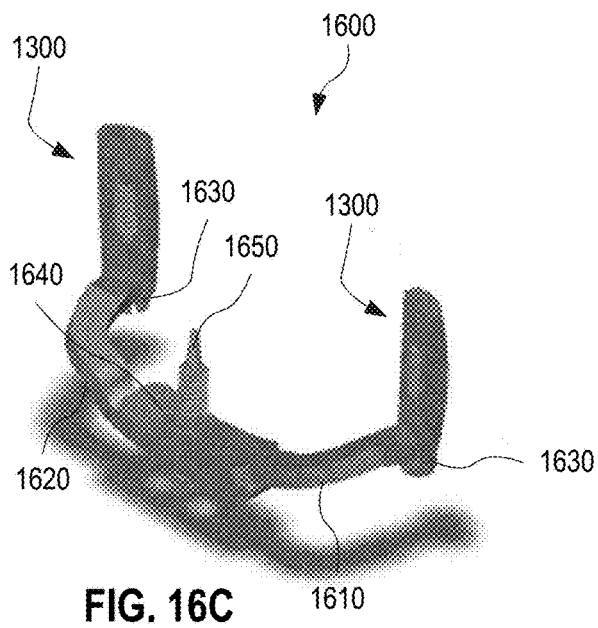
Figure 16D:
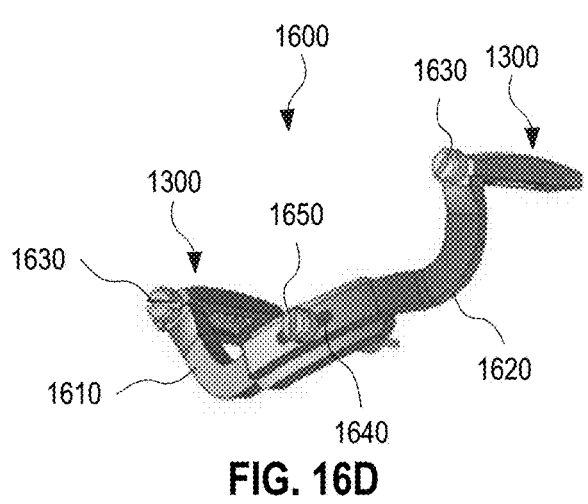

FIG. 16A shows, in an anterior view, a pair of motion-preserving implants 1300 (FIGS. 13A-D) secured to uncinate joints 120 (FIG. 1) using bracket 1600. FIG. 16B shows bracket 1600 in side elevation view, separate from cervical spine segment 180. Each of FIGS. 16C and 16D shows bracket 1600 in perspective view, separate from cervical spine segment 180. FIGS. 16A-D are best viewed together.

Bracket 1600 includes a half-bracket 1610 and a half-bracket 1620. Each of half-brackets 1610 and 1620 is attached to one motion-preserving implant 1300 by a fastener 1630. Fastener 1630 is, for example, a bolt or a screw. Each of half-brackets 1610 and 1620 has a slot 1640 configured to accept a screw 1650. Screw 1650 secures half-brackets 1610 and 1620 to an anterior surface of the vertebral body of superior cervical vertebra 184. The shape of half-brackets 1610 and 1620 may be different from those shown in FIGS. 16A-D, without departing from the scope hereof.

Although FIGS. 14-16D illustrate a configuration wherein motion-preserving implant 1300 is secured to superior cervical vertebra 184, motion-preserving implant 1300 may be inserted into uncinate joint 120 with screw 1310 contacting inferior surface 686 and with surface 1322 facing superior surface 684, such that motion-preserving implant 1300 may be secured to inferior cervical vertebra 186, without departing from the scope hereof.

Figure 17A:
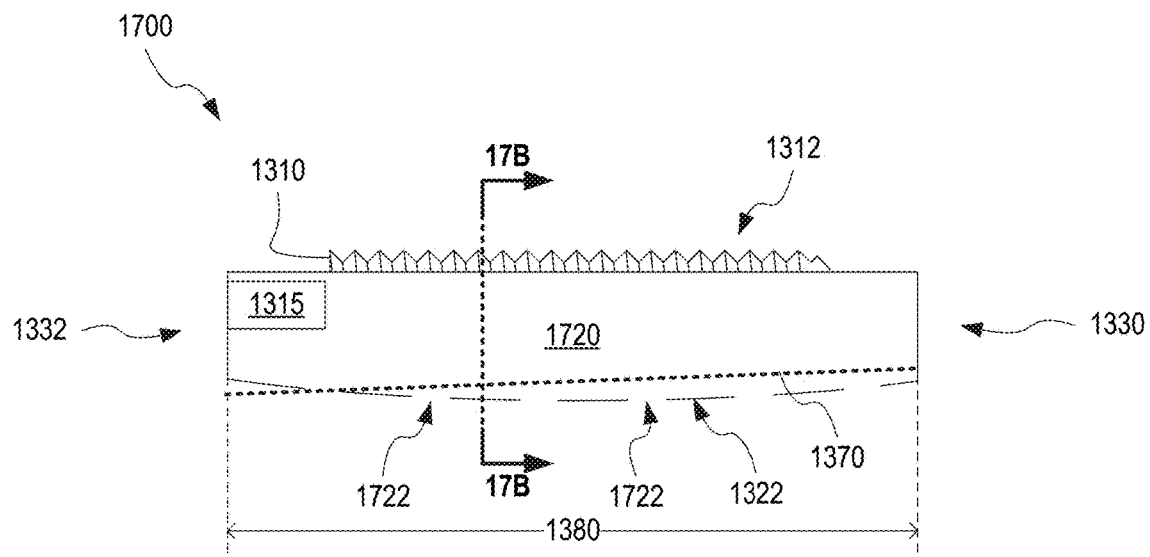
FIGS. 17A, 17B, 17C, and 17D illustrate a screw-in implant for stabilizing an uncinate joint, according to an embodiment.
Figure 17B:
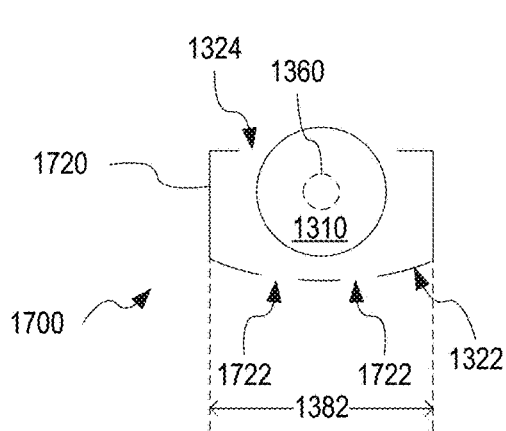
Figure 17C:
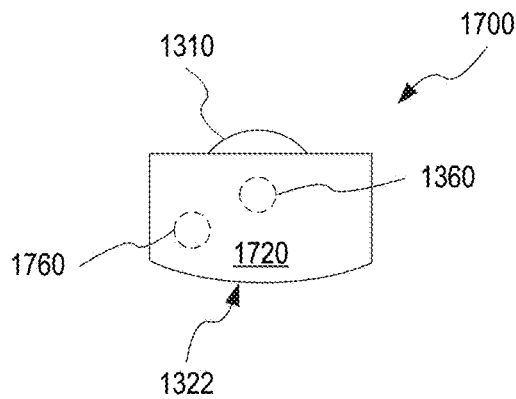
Figure 17D:
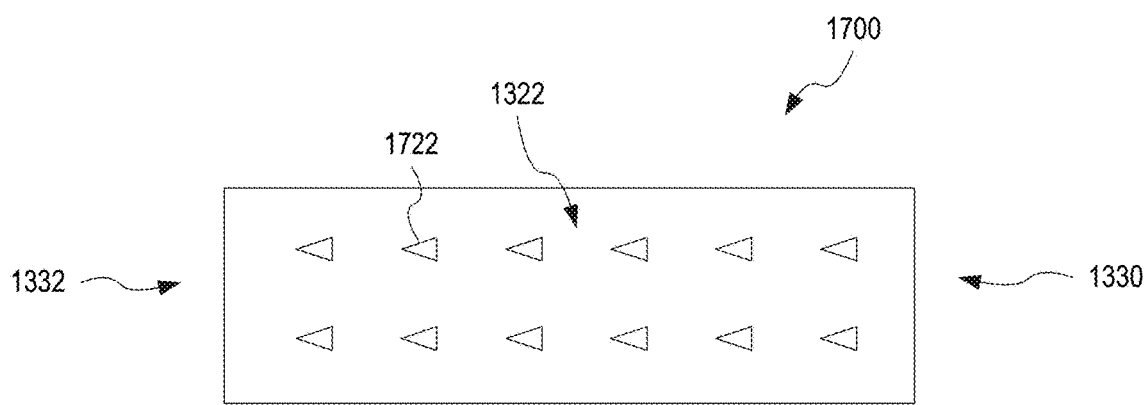

FIGS. 17A, 17B, 17C, and 17D illustrate one exemplary screw-in implant 1700 for stabilizing uncinate joint 120 (FIG. 1). Screw-in implant 1700 is similar to motion-preserving implant 1300 (FIGS. 13A-D) except that screw-in implant 1700 includes fenestrations 1722 that at least help secure screw-in implant 1700 to the surface of uncinate joint 120 opposite the surface of uncinate joint interfacing with screw 1310. Thus, screw-in implant 1700 is configured to fix motion of uncinate joint 120. Additionally, screw-in implant 1700 may include an access port 1760 that accepts bone graft material into screw-in implant 1700 from its trailing end 1332. FIG. 17A shows screw-in implant 1700 in side elevation. FIG. 17B shows screw-in implant 1700 in cross-sectional view, wherein the cross section is taken along line 17B-17B in FIG. 17A. FIG. 17C shows trailing end 1332 of screw-in implant 1700 in elevation view. FIG. 17D shows a fenestrated surface of screw-in implant 1700. FIGS. 17A-D are best viewed together.

As compared to motion-preserving implant 1300, screw-in implant 1700 includes a housing 1720 instead of housing 1320. Housing 1720 is similar to housing 1320, except that surface 1322 in housing 1720 includes fenestrations 1722. For clarity of illustration, not all fenestrations 1722 are labeled in FIGS. 17A-D. FIG. 17C shows surface 1322. Fenestrations 1722 may aid in securing screw-in implant 1700 to uncinate joint 120 through friction between fenestrations 1722 and an associated one of superior surface 684 and inferior surface 686.

In one embodiment, each fenestration 1722 is wider (in dimension associated with width 1382) closer to leading end 1330 and narrower closer to trailing end 1332. This shape may result in greater friction against lateral movement and posterior-to-anterior movement of surface 1322 in uncinate joint 120 than the friction between surface 1322 and uncinate joint 120 associated with insertion of screw-in implant 1700 along anterior-to-posterior direction 210 (FIG. 2). However, the shape of fenestration 1722 may differ from that shown in FIG. 17C, without departing from the scope hereof. Likewise, the number of fenestrations 1722, and/or the pattern in which fenestrations 1722 are arranged, may be different from what is shown in FIGS. 17A-C.

In one implementation, screw-in implant 1700 is self-securing by virtue of threads 1312. In another implementation, screw-in implant 1700 is secured to cervical spine segment 180 using a mounting bracket, and associated fasteners. In one example, screw-in implant 1700 is secured to cervical spine segment 180 using bracket 1510 (FIG. 15), bracket 1050 (FIG. 10B), or bracket 1600 (FIGS. 16A-D). In another example, screw-in implant 1700 is secured to cervical spine segment 180 using two brackets 1600 with one bracket secured to superior vertebra 184 and the other bracket secured to inferior vertebra 186.

In one exemplary scenario, screw-in implant 1700 is implemented in method 400 according to an embodiment of method 400, which includes step 434 and 438. In this scenario, bone graft material is loaded into housing 1720 and allowed to contact both superior surface 684 and inferior surface 686 (FIG. 6B) of uncinate joint 120 through fenestrations 1722 and opening 1324. In one implementation of step 438, bone graft material is loaded into housing 1720 prior to insertion of screw-in implant 1700 into uncinate joint 120. In another implementation of step 438, bone graft material is loaded into housing 1720 after insertion of screw-in implant 1700 into uncinate joint 120. In this implementation, bone graft material may be loaded into housing 1720 at trailing end 1332 via through-hole 1360, and with screw 1310 implemented with fenestrations that connect through-hole 1360 to an external surface of screw 1310 (as discussed in reference to fenestrated, threaded implant 800 (FIGS. 8A-D). Optionally, through-hole 1360 is subsequently sealed with a cap. In one example, sealing is accomplished by a mounting bracket, and/or associated fastener, used to secure screw-in implant 1700 to cervical spine segment 180. Such sealing may be accomplished using (a) fastener 1540 (FIG. 15) optionally with bracket 1510, (b) fastener 1040 optionally with bracket 1050 (FIG. 10B), or (c) fastener 1630 (FIGS. 16A-D) optionally with bracket 1600. In yet another implementation of step 438, bone graft material is loaded into housing 1720, via an access port 1760, after insertion of screw-in implant 1700 into uncinate joint 120. Access port 1760 may be subsequently sealed using a cap.

Without departing from the scope hereof, screw-in implant 1700 may be configured to allow for removal of screw 1310, along a posterior-to-anterior direction, when screw-implant 1700 is in place in uncinate joint 120. In this case, bone graft material may be loaded into housing 1720 after removal of screw 1310.

Figure 18A:
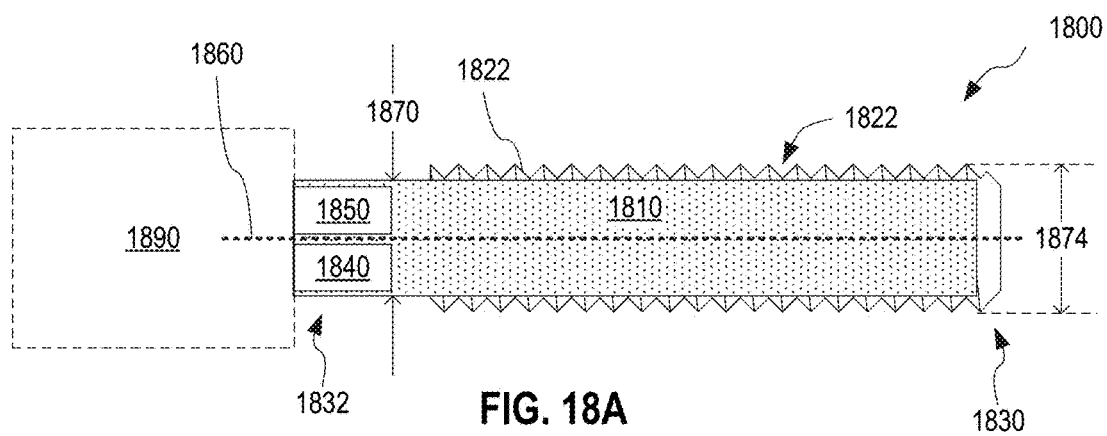
FIGS. 18A, 18B, 18C, and 18D illustrate an implant system including an implant, for stabilizing an uncinate joint, and a screw for inserting the implant into the uncinate joint, according to an embodiment.
Figure 18B:
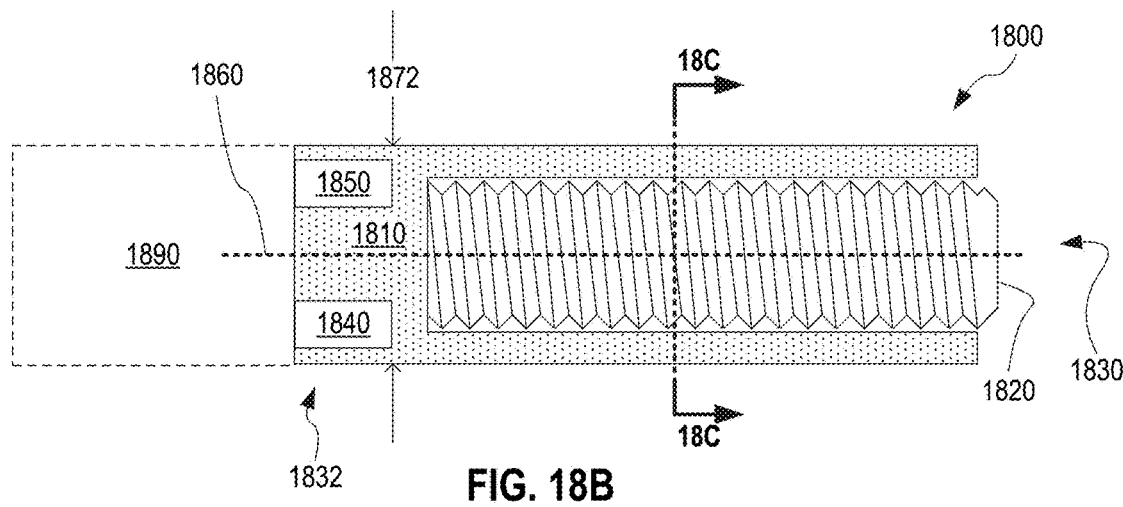
Figure 18C:
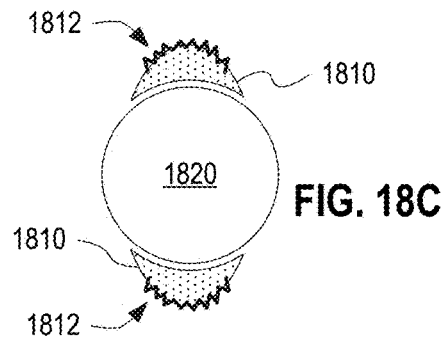
Figure 18D:
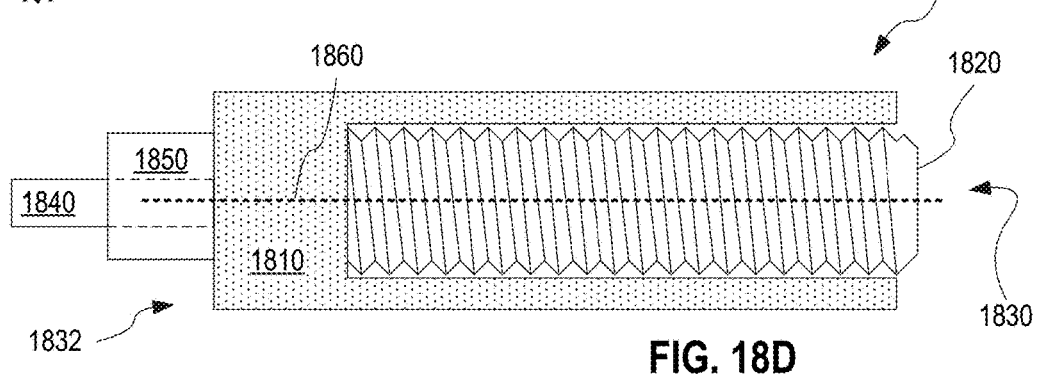

FIGS. 18A-D illustrate one exemplary implant system 1800 including (a) one exemplary implant 1810 for stabilizing uncinate joint 120 (FIG. 1) and (b) one exemplary screw 1820 for inserting implant 1810 into uncinate joint 120. Implant 1810 is an embodiment of implant 100. Implant system 1800 is associated with a longitudinal axis 1860. Longitudinal axis 1860 is generally oriented along anterior-to-posterior direction 210 (FIG. 2) when implant system 1800 is located in uncinate joint 120. FIGS. 18A and 18B show implant system 1800 in mutually orthogonal side elevation views, both orthogonal to longitudinal axis 1860. FIG. 18C shows implant system 1800 in cross-sectional view, wherein the cross section is taken along line 18C-18C in FIG. 18B. FIG. 18D shows one example of implant system 1800 in the same view as used for FIG. 18B. FIGS. 18A-D are best view together. Implant system 1800 is configured to insert implant 1810 into uncinate joint 120 along anterior-to-posterior direction 210. Implant system 1800 and implant 1810 may be implemented in method 400 (FIG. 4).

Implant system 1800 has a leading end 1830 that enters uncinate joint 120 first, when inserting implant system 1800 into uncinate joint 120. Opposite leading end 1830, implant system has a trailing end 1832. Implant 1810 has an elongated cross section in the plane orthogonal to longitudinal axis 1860 (see FIG. 18C). For example, implant 1810 is oval, rectangular, or rectangular with rounded corners. The cross section of screw 1820 is circular in the plane orthogonal to longitudinal axis 1860. Screw 1820 includes threads 1822. Threads 1822 may have properties similar to threads 510 of threaded implant 500 (FIGS. 5A and 5B).

FIG. 18A shows implant system 1800 in an orientation associated with a minimum extent 1870 of implant 1810 in the plane orthogonal to longitudinal axis 1860. FIG. 18B shows implant system 1800 in an orientation associated with a maximum extent 1872 of implant 1810 in the plane orthogonal to longitudinal axis 1860. Screw 1820 has diameter 1874 that is greater than minimum extent 1870 and less than maximum extent 1872. Thus, in the dimension associated with minimum extent 1870, threads 1822 protrude from implant 1810, while in the dimension associated with maximum extent 1872, screw 1820 is enclosed by implant 1810.

Implant 1810 includes a rough surface 1812 on at least on a portion of implant 1810 configured to contact superior surface 684 and inferior surface 686 when implant 1810 is placed in uncinate joint 120. For clarity of illustration, rough surface 1812 is not indicated in FIGS. 18A and 18B. Rough surface 1812 may include fenestrations, protruding features, surface texture, or other elements to form rough surface 1812.

Implant system 1800 further includes interfaces 1840 and 1850, located at trailing end 1832. A surgeon may couple a tool 1890 to interfaces 1840 and 1850 to rotate implant 1810 and screw 1820, respectively, about longitudinal axis 1860. Tool 1890 and interfaces 1840 and 1850 are configured such that the surgeon may rotate screw 1820 independently of implant 1810. Without departing from the scope hereof, one or both of interfaces 1840 and 1850 may include functionality to rotate implant 1810 and screw 1820 in response to actuation by tool 1890. Tool 1890 may include two different tools respectively configured to interface with interfaces 1840 and 1850. In one embodiment, interface 1840 is nested in interface 1850 and/or protrudes interface 1840. In this embodiment, the tool configured to interface with interface 1850 fits over interface 1840, and optionally also over the tool configured to interface with interface 1840. FIG. 18D shows one such example of implant system 1800, wherein interface 1850 is an extension of implant 1810 away from leading end 1830, and interface 1840 is a shaft coupled to screw 1820 and extending through interface 1850 in the direction away from leading end 1830. In an alternate embodiment, 1850 has an opening for inserting a tool therethrough to engage with an interface 1840 closer than interface 1850 to leading end 1830.

Although not shown in FIGS. 18A and 18B, one or both of implant 1810 and screw 1820 may be tapered, as discussed for threaded implant 500 (FIGS. 5A and 5B), without departing from the scope hereof.

Figure 19A:
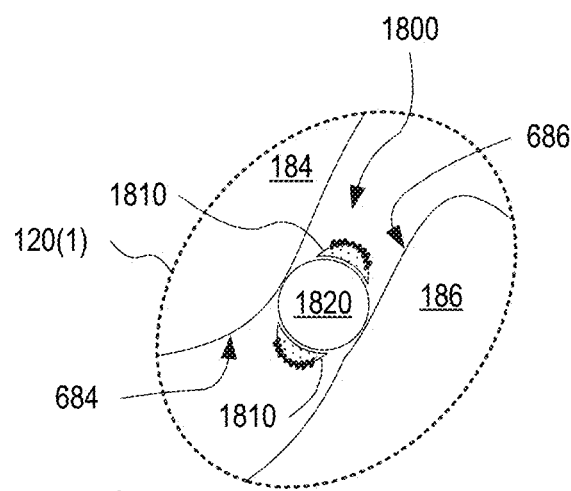
FIGS. 19A and 19B illustrate, in a posterior view, insertion of the implant of FIGS. 18A-D), using the implant system of FIGS. 18A-D, into an uncinate joint along an anterior-to-posterior direction, according to an embodiment.
Figure 19B:
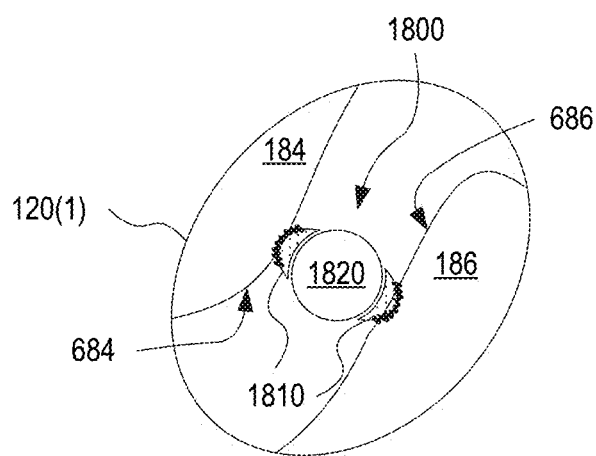

FIGS. 19A and 19B illustrate, in a posterior view, insertion of implant 1810 (FIGS. 18A-D), using implant system 1800, into uncinate joint 120 (FIG. 1) along anterior-to-posterior direction 210 (FIG. 2) according to method 400 (FIG. 4). Implant system 1800 may perform steps 420 and 430 of method 400. FIGS. 19A and 19B are best viewed together.

FIG. 19A shows implant system 1800 during insertion of implant system 1800 into uncinate joint 120 along anterior-to-posterior direction 210. During this operation, the surgeon operates tool 1890 (not shown in FIGS. 19A and 19B) to orient implant 1810 such that threads 1822 of screw 1820 are in contact with superior surface 684 (FIG. 6B) and inferior surface 686 of uncinate joint 120. The surgeon operates tool 1890 to rotate screw 1820 to screw implant system 1800 into uncinate joint 120. When implant system 1800 is in a location within uncinate joint 120, suitable for stabilizing uncinate joint 120 using implant 1810, the surgeon uses tool 1890 to rotate implant 1810, such that rough surfaces 1812 grip superior surface 684 and inferior surface 686 (see FIG. 19B). This operation secures implant 1810 to uncinate joint 120. Additionally, this operation may serve to distract uncinate joint 120 to increase the spacing between superior surface 684 and inferior surface 686. In turn, increasing the spacing between superior surface 684 and inferior surface 686 may relieve pathological issues in cervical spine segment 180, such as nerve impingement or damage to intervertebral disc 150. In one exemplary scenario, the spacing between superior surface 684 and inferior surface 686 is increased by one or several millimeters, when implant 1810 is rotated as shown in FIG. 19B.

After rotating implant 1810, as shown in FIG. 19B, the surgeon may use tool 1890 to back screw 1820 out of uncinate joint 120, along a posterior-to-anterior direction, while leaving implant 1810 in uncinate joint 120. Subsequently, the surgeon may load bone graft material into implant 1810 from trailing end 1832, and optionally seal trailing end 1832 with a cap, similar to the cap shown in FIG. 8C.

FIGS. 20A and 20B illustrate one exemplary implant 2000 configured to be tapped or slid into uncinate joint 120 and, after positioning in uncinate joint 120, rotated to distract uncinate joint 120 and to be locked in place in uncinate joint 120. Implant 2000 is an embodiment of implant 100. Implant 2000 is associated with a longitudinal axis 2002. Longitudinal axis 2002 is generally oriented along anterior-to-posterior direction 210 (FIG. 2) when implant 2000 is located in uncinate joint 120. FIG. 20A shows implant 2000 in side elevation view, and FIG. 20B shows implant 2000 in cross-sectional view, wherein the cross section is taken along line 20B-20B in FIG. 20A. FIGS. 20A and 20B are best viewed together. Implant 2000 may be implemented in method 400 (FIG. 4).

Implant 2000 has length 2080 in the dimension parallel to longitudinal axis 2002. The cross section of implant 2000, in the dimensions orthogonal to length 2080, has a shorter extent 2082 and a longer extent 2084. Although FIGS. 20A and 20B show implant 2000 as having oval cross section, the cross section of implant 2000 may be of another oblong shape such as rectangular with rounded corners, without departing from the scope hereof. Length 2080 may be similar to length 580 of threaded implant 500. Longer extent 2084 may be similar to maximum extent 1872. Shorter extent 2082 may be between at least one millimeter less than longer extent 2084, for example between two and four millimeters less than longer extent 2084.

In one embodiment, implant 2000 is tapered as indicated by dashed lines 2060 to ease insertion of threaded implant into uncinate joint 120 and/or to match the deviation from parallelism between cervical vertebrae 184 and 186 at uncinate joint 120 stemming from the lordosis of the cervical spine. In this embodiment, the taper angle 2062 may be less than 15°, for example between 4° and 8°. Although FIG. 20A shows optional tapering (as indicated by dashed lines 2060) as extending along the full length of implant 2000, implant 2000 may be tapered only along a portion of the length of implant 2000, without departing from the scope hereof. In one such example, a leading end of implant 2000 is tapered (as indicated by dashed lines 2060) while a trailing end of implant 2000 is not tapered.

Surfaces 2024 and 2026 at the polar ends of implant 2000, associated with longer extent 2084, are configured to contact superior surface 684 and inferior surface 686 when implant 2000 is secured in uncinate joint 120 in its final position in uncinate joint 120. Surfaces 2024 and 2026 may be rough to self-secure implant 2000 in uncinate joint 120. To achieve roughness, surfaces 2024 and 2026 may include fenestrations, protruding features, surface texture, or other non-smooth elements. In certain embodiments, implant 2000 includes a receptacle 2050 configured to interface with a tool. This tool may be used to control rotation of implant 2000 about longitudinal axis 2060 during and/or after insertion of implant 2000 into uncinate joint 120. Implant 2000 may be cannulated with through-hole 530 along the full length 2080 of implant 2000, such that implant 2000 may be inserted into uncinate joint 120 over a guide wire.

Although not shown in FIGS. 20A and 20B, implant 2000 may have at least one void capable of accommodating bone graft material, without departing from the scope hereof. Such embodiments of implant 2000 may be utilized in step 2224 of method 2200, in step 2370 of method 2300, and in step 2418 of method 2400. Implant 2000 may include a coating, for example a hydroxyapatite coating, to achieve improved fixation of implant 2000 to uncinate joint 120, without departing from the scope hereof.

In one embodiment, implant 2000 is substantially composed of a metal such as titanium, titanium alloy, stainless steel, cobalt, chromium, or a combination thereof. In another embodiment, implant 2000 includes a porous portion with pores capable of accommodating bone graft material within uncinate joint 120, or a porous portion substantially composed of bone graft material, as discussed in reference to step 2224 of method 2200, in step 2370 of method 2300, and in step 2418 of method 2400. In one example, implant 2000 is substantially composed of, or includes, porous metal. In yet another embodiment, implant 2000 is substantially composed of allograft bone. In a further embodiment, implant 2000 is substantially composed of polymer. The polymer is, for example, polyetheretherketone (PEEK) or another polyaryletherketone (PAEK) polymer. Any of the above materials may be used in a 3-D printing process to make implant 2000.

FIGS. 21A and 21B illustrate, in anterior view, insertion of implant 2000 (FIGS. 20A and 20B) into uncinate joint 120 (FIG. 1) along anterior-to-posterior direction 210 (FIG. 2) according to method 400 (FIG. 4). Implant 2000 may perform steps 420 and 430 of method 400. FIGS. 21A and 21B are best viewed together.

FIG. 21A shows implant 2000 during insertion of implant 2000 into uncinate joint 120 along anterior-to-posterior direction 210. During this operation, the surgeon orients implant 2000 with longer extent 2084 generally along the opening of uncinate joint 120, such that the spacing between superior surface 684 and inferior surface 686 does not need to accommodate longer extent 2084 and such that optionally rough surfaces 2024 and 2026 are away from contact with superior surface 684 and inferior surface 686.

When implant 2000 is in a location within uncinate joint 120, suitable for stabilizing uncinate joint 120 using implant 2000, the surgeon rotates implant 2000, such that surface 2024 comes grips superior surface 684 and surface 2026 grips inferior surface 686 (see FIG. 21B). This operation secures implant 2000 to uncinate joint 120. Additionally, this operation may serve to distract uncinate joint 120 to increase the spacing between superior surface 684 and inferior surface 686. In turn, increasing the spacing between superior surface 684 and inferior surface 686 may relieve pathological issues in cervical spine segment 180, such as nerve impingement or damage to intervertebral disc 150. In one exemplary scenario, the spacing between superior surface 684 and inferior surface 686 is increased by one or several millimeters, when implant 2000 is rotated as shown in FIG. 20B.

Without departing from the scope hereof, a bracket, such as bracket 1010 or bracket 1050, may be used to fix implant 2000 in uncinate joint 120, either alone or in cooperation with roughness of surfaces 2024 and 2026.

Figure 22:
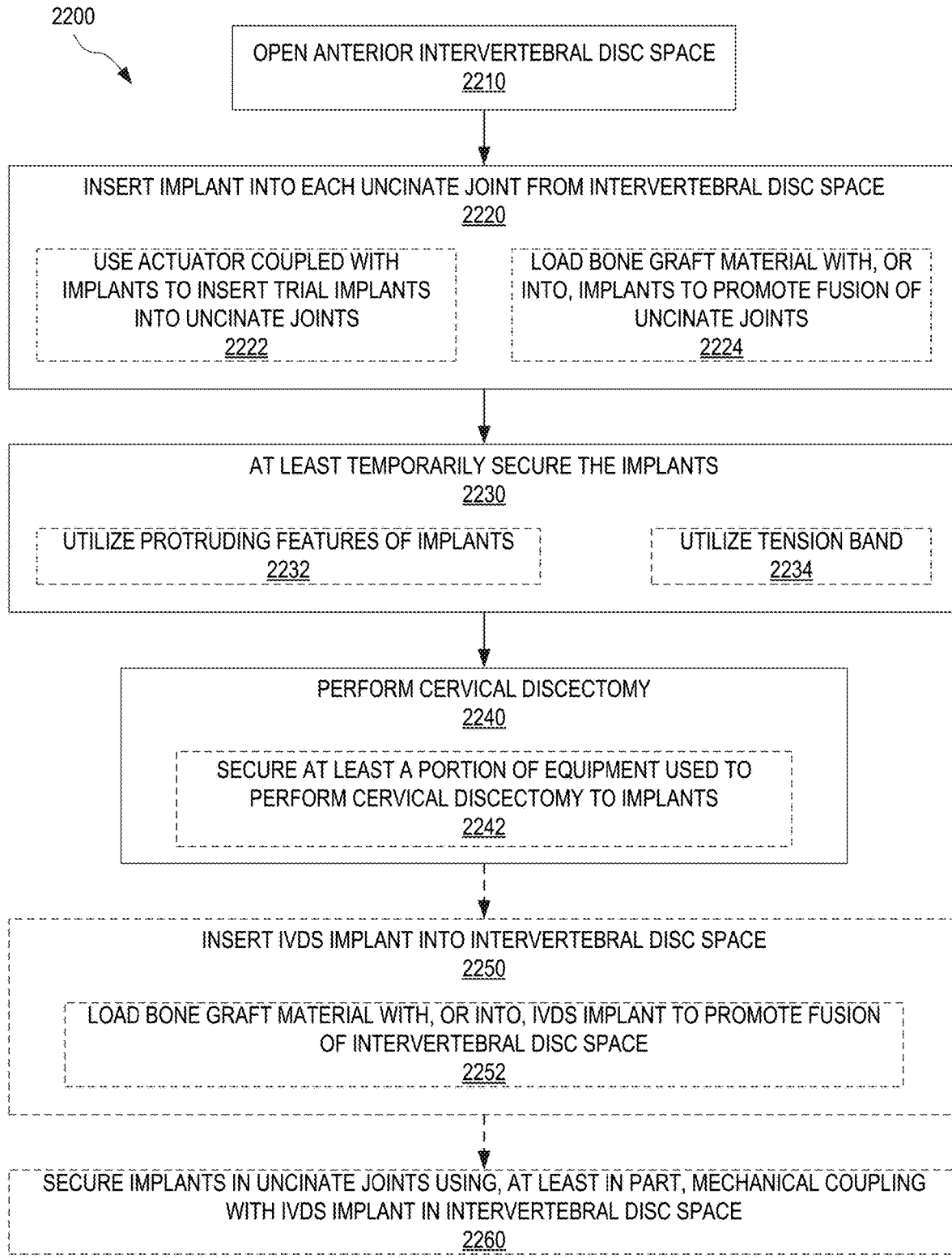
FIG. 22 illustrates a method for stabilizing the uncinate joints of a cervical spine segment, using access to the uncinate joints via medial-to-lateral directions, according to an embodiment.

FIG. 22 illustrates one exemplary method 2200 for stabilizing uncinate joints 120 (FIG. 1) of cervical spine segment 180, using access to uncinate joints 120 via medial-to-lateral directions 220 (FIG. 2). Method 2200 is an embodiment of method 300 (FIG. 3).

In a step 2210, at least an anterior portion of intervertebral disc space 140 is opened to gain access to uncinate joints 120 via medial-to-lateral directions 220. Step 2210 may utilize methods known in the art. For example, a surgeon may access intervertebral disc space 140 by (a) making a skin incision in the front of the neck, (b) making a tunnel to the spine by moving aside muscles and retracting the trachea, esophagus, and arteries, and (c) lifting and holding aside the muscles that support the front of the spine. Optionally, the surgeon increases the height of intervertebral disc space 140, for example by screwing pins into both superior cervical vertebra 184 and inferior cervical vertebra 186 and using these pins to distract intervertebral disc space 140, or by distracting uncinate joints 120 from intervertebral disc space 140 as discussed below in reference to FIGS. 37A-C and 38.

In a step 2220, for each uncinate joint 120, implant 100 is inserted into uncinate joint 120 from intervertebral disc space 140 along medial-to-lateral directions 220. Exemplary implants compatible with use in step 2220 are discussed below in reference to FIGS. 25A-28 and 36A-F. In one embodiment, step 2220 includes a step 2222 of using an actuator coupled with implants 100 to insert implants 100 into uncinate joints 120. In one example of step 2222, a surgeon uses an actuator, holding a pair of implants 100, to insert implants 100 into uncinate joints 120 from intervertebral disc space 140. Exemplary actuators are discussed below in reference to FIGS. 29-35B. Optionally, step 2220 includes a step 2224 of loading bone graft material with, or into, implants 100 to promote fusion of uncinate joints 120. In one example of step 2224, each implant 100 used in step 2220 has at least one void capable of accommodating bone graft material. Bone graft material may be loaded into the void(s) of each implant 100 before or after inserting implant 100 into uncinate joint 120. In another example of step 2224, at least a portion of each implant 100 is a porous portion substantially composed of bone graft material.

In a step 2230, implants 100, inserted into uncinate joints 120 in step 2220, are at least temporarily secured to respective uncinate joints 120. Step 2230 may be an integrated element of step 2220. Step 2230 may utilize self-securing embodiments of implants 100 or utilize additional hardware to secure implants 100 in uncinate joints 120. In one embodiment, step 2230 includes a step 2232 of, for each uncinate joint 120, utilizing one or more protruding features of implant 100 to grip at least one of superior surface 684 (FIG. 6B) and inferior surface 686, and thus at least temporarily securing implant 100 in uncinate joint 120. Exemplary protruding features include barbs, ribs, and surface texture. Exemplary implants compatible with step 2232 are discussed below at least in reference to FIGS. 25A-D, 27, 36A-F, and 41. Step 2230 may include a step 2234, wherein a tension band is utilized to secure each implant 100 to the corresponding uncinate joint 120. Steps 2232 and 2234 may be implemented in combination. Although not shown in FIG. 22, the actuator of step 2222 may remain coupled to implants 100 during step 2230, such that the actuator at least participates in securing implants 100 in uncinate joints 120.

In a step 2240, method 2200 performs cervical discectomy to remove intervertebral disc 150, or at least the majority thereof, from intervertebral disc space 140. Step 2240 may utilize methods and tools known in the art. Since implants 100 are located in uncinate joints 120, implants 100 prevent the surgeon from accidentally damaging the vertebral arteries 230 of patient 170. In one embodiment, step 2240 utilizes at least one of implants 100 located in uncinate joints 120, and includes a step 2242 of securing at least a portion of the equipment, used to perform the cervical discectomy, to implants 100. In one example of step 2242, at least one of implants 100 is coupled with an extension that extends outside the corresponding uncinate joint 120 in an anterior direction, and cervical discectomy equipment is attached to this at least one extension. For example, a soft-tissue retractor, used to retract soft tissue of the neck, may be attached to at least one implant 100 or extension thereof. Exemplary extensions and soft-tissue retractors are discussed below in reference to FIGS. 30-35B.

In one embodiment, method 2200 further includes a step 2250 subsequent to step 2240. In step 2250, an IVDS implant is inserted into intervertebral disc space 140. In one embodiment, the IVDS implant is an artificial disc device configured to preserve motion of cervical spine segment 180. In this embodiment, implants 100 may be motion-preserving as well or, alternatively, implants 100 are biodegradable/bioabsorbable and, after some time, cease to play a role in the mobility of cervical spine segment 180. In another embodiment, step 2250 promotes fusion of cervical spine segment 180 within intervertebral disc space 140. In this embodiment, step 2250 includes a step 2252 of loading bone graft material with, or into, the IVDS implant. Method 2200 may implement step 2252 together with step 2224 to achieve fusion strength and/or speed superior to that possible when fusing only intervertebral disc space 140. In one example, steps 2250 and 2252 utilize an IVDS implant that is a rigid structure with at least one void capable of accommodating bone graft material. The void(s) may be loaded with bone graft material prior to or after insertion of the IVDS implant into intervertebral disc space 140. In another example, steps 2250 and 2252 utilize an IVDS implant that is or includes a porous element substantially composed of bone graft material. In yet another example, the IVDS implant of steps 2250 and 2252 is a bag with bone graft material. The use of a non-rigid IVDS implant, such as a bag, in step 2250 is facilitated by stabilizing uncinate joints 120 through steps 2220 and 2230.

In certain embodiments, the IVDS implant of step 2250 is not load bearing in cervical spine segment 180, or carries only a fraction of the load. These embodiments are facilitated by the load bearing capacity of implants 100 inserted into uncinate joints 120 in step 2220. This is in contrast to conventional intervertebral cages that must be configured to carry the load of cervical spine segment 180, which imposes significant requirements on how the conventional intervertebral cages contact cervical vertebrae 184 and 186. In comparison, a non-load bearing or partial-load bearing IVDS implant, used in step 2250, may have less contact area with cervical vertebrae 184 and 186, for example.

Optionally, step 2250 is followed by a step 2260 of securing implants 100 (inserted into uncinate joints 120 in step 2220) using, at least in part, mechanical coupling with an IVDS implant inserted into intervertebral disc space 140 in step 2252. For example, this IVDS implant may contact implants 100 to prevent implants 100 from migrating towards intervertebral disc space 140. In one exemplary scenario, intervertebral disc 150 participates in the tension band of step 2234. After cervical discectomy in step 2240, the tension band may be loosened and it may be preferred to employ additional measures to secure implants 100 in uncinate joints 120. Step 2260 serves to provide such measures. FIGS. 41-47B, discussed below, illustrate one exemplary embodiment of implant 100 and one exemplary IVDS implant, which are compatible with step 2260. Without departing from the scope hereof, step 2252 may be performed after step 2260. Step 2260 may utilize a non-load bearing or partial-load bearing IVDS implant.

Figure 23:
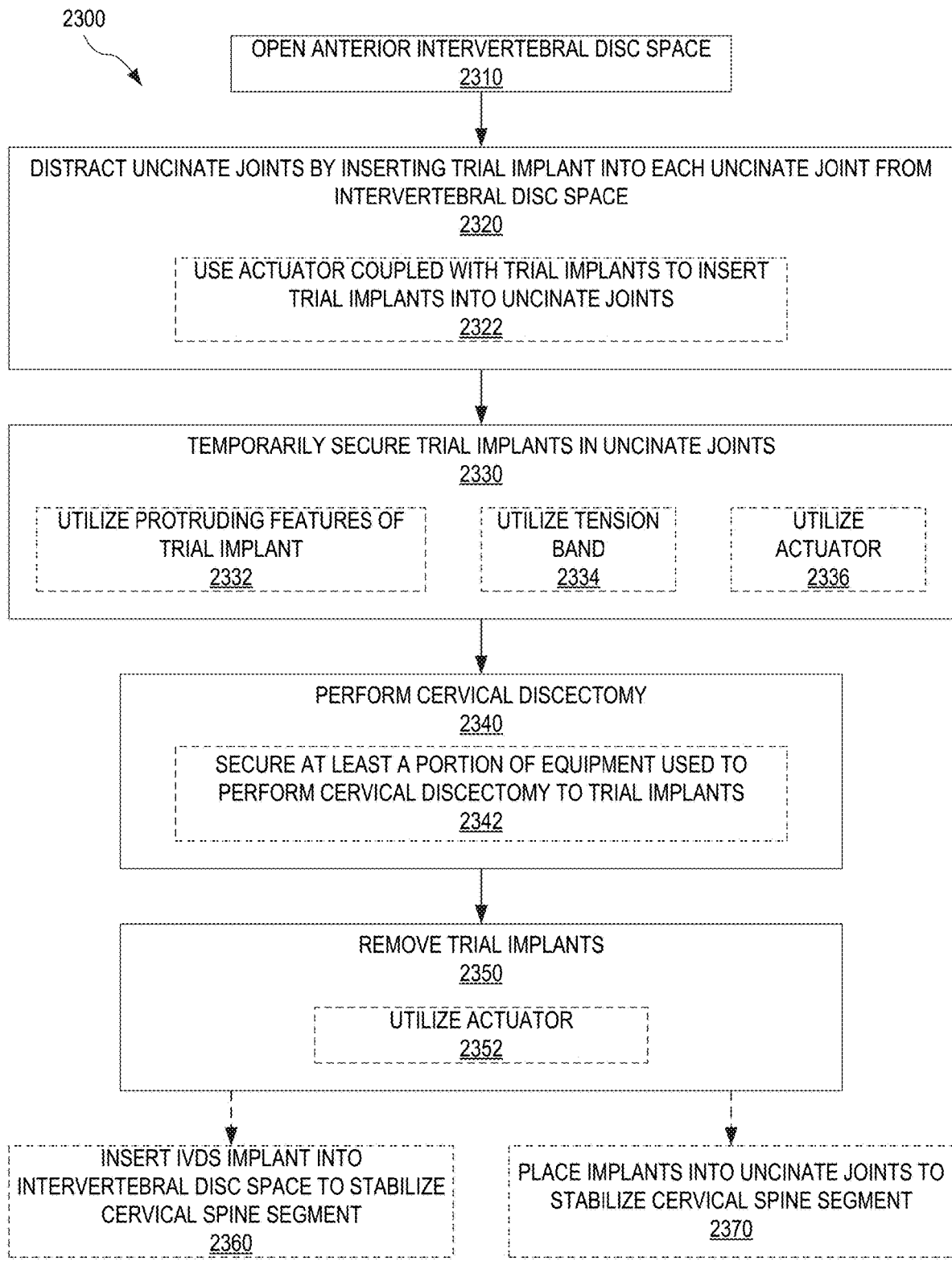
FIG. 23 illustrates a method for stabilizing the uncinate joints of a cervical spine segment at least while performing cervical discectomy, according to an embodiment.

FIG. 23 illustrates one exemplary method 2300 for stabilizing uncinate joints 120 of cervical spine segment 180 (FIG. 1) at least while performing cervical discectomy. Method 2300 accesses uncinate joints 120 from intervertebral disc space 140 along medial-to-lateral directions 220 (FIG. 2). Method 2300 is an embodiment of method 300 (FIG. 3), which utilizes temporary trial implants for at least a portion of the procedure. Trial implants are embodiments of implant 100 configured to be removable.

In a step 2310, at least an anterior portion of intervertebral disc space 140 is opened to gain access to uncinate joints 120 via medial-to-lateral directions 220. Step 2310 is similar to step 2210 of method 2200 (FIG. 22).

In a step 2320, each uncinate joint 120 is distracted by inserting a trial implant into uncinate joint 120 from intervertebral disc space 140 along medial-to-lateral direction 220. In one example of step 2320, a surgeon inserts a removable embodiment of implant 100 into each uncinate joint 120 from intervertebral disc space 140 along medial-to-lateral direction 220. Exemplary implants compatible with use in step 2220 are discussed below in reference to FIGS. 25A-28 and 32A-36F.

In a step 2330, the trial implants of step 2320 are temporarily secured in uncinate joints 120. Step 2330 may be an integrated element of step 2320. Step 2330 may utilize self-securing embodiments of implants 100. In one embodiment, step 2330 includes a step 2332 of, for each uncinate joint 120, utilizing one or more protruding features of implant 100 to grip at least one of superior surface 684 (FIG. 6B) and inferior surface 686, and thus temporarily securing the trial implant in uncinate joint 120. Exemplary protruding features include barbs, ribs, and surface texture. Exemplary implants compatible with step 2332 are discussed below in reference to FIGS. 25A-D, 27, 36A-F, and 41. Step 2330 may include a step 2334, wherein a tension band is utilized to secure each trial implant to the corresponding uncinate joint 120. Steps 2332 and 2334 may be implemented in combination.

In a step 2340, method 2300 performs cervical discectomy to remove intervertebral disc 150, or at least the majority thereof, from intervertebral disc space 140. Step 2340 may utilize methods and tools known in the art. Since the trial implants are located in uncinate joints 120, the trial implants prevent the surgeon from accidentally damaging the vertebral arteries 230 of patient 170. In one embodiment, step 2340 utilizes at least one of the trial implants located in uncinate joints 120, and includes a step 2342 of securing at least a portion of the equipment, used to perform the cervical discectomy, to this at least one trial implant. In one example of step 2342, at least one of the trial implants, or an extension coupled therewith, extends outside the corresponding uncinate joint 120 in an anterior direction, and cervical discectomy equipment is attached to this at least one trial implant or extension thereof. For example, a soft-tissue retractor, used to retract soft tissue of the neck, may be attached to at least one trial implant or extension thereof. Exemplary extensions are discussed below in reference to FIGS. 30-35B.

In a step 2350, the trial implants are removed from uncinate joints 120. The trial implants may be removed using methods known in the art. Step 2350 may include pulling out the trial implants using plier-type tools and/or tapping out the trial implants. Step 2350 may include breaking the trial implants.

In certain embodiments, at least a portion of method 2300 utilizes an actuator to handle the trial implants. Step 2320 may include a step 2322 of utilizing an actuator coupled with the trial implants to insert the trial implants into uncinate joints 120. In one example of step 2322, a surgeon uses an actuator, holding a pair of trial implants, to insert the trial implants into uncinate joints 120 from intervertebral disc space 140. Exemplary actuators are discussed below in reference to FIGS. 29-35B. Step 2330 may include a step 2336 of utilizing an actuator to at least assist in securing the trial implants in uncinate joints 120. In one example of steps 2322 and 2336, the actuator used in step 2322 remains coupled with the trial implants during step 2336 to at least participate in securing the trial implants in uncinate joints 120. Step 2350 may include a step 2352 of utilizing an actuator coupled with the trial implants to remove the trial implants. Step 2350 may combine step 2352 with other removal methods such as tapping. In one example of step 2322 and 2352, the actuator used in step 2322 remains coupled with the trial implants during step 2336 to at least participate in removing the trial implants from uncinate joints 120.

In one embodiment, method 2300 further includes a step 2360 of inserting an IVDS implant into intervertebral disc space 140 to stabilize cervical spine segment 180. One example of step 2360 utilizes methods and IVDS implants known in the art.

In another embodiment, method 2300 further includes a step 2370, subsequent to step 2350, of placing implants 100 in uncinate joints 120 to stabilize uncinate joints 120 permanently or for a longer period of time, such that patient 170 leaves the procedure with implants 100 in uncinate joints 120. Method 2300 may include both of steps 2360 and 2370.

Figure 24:
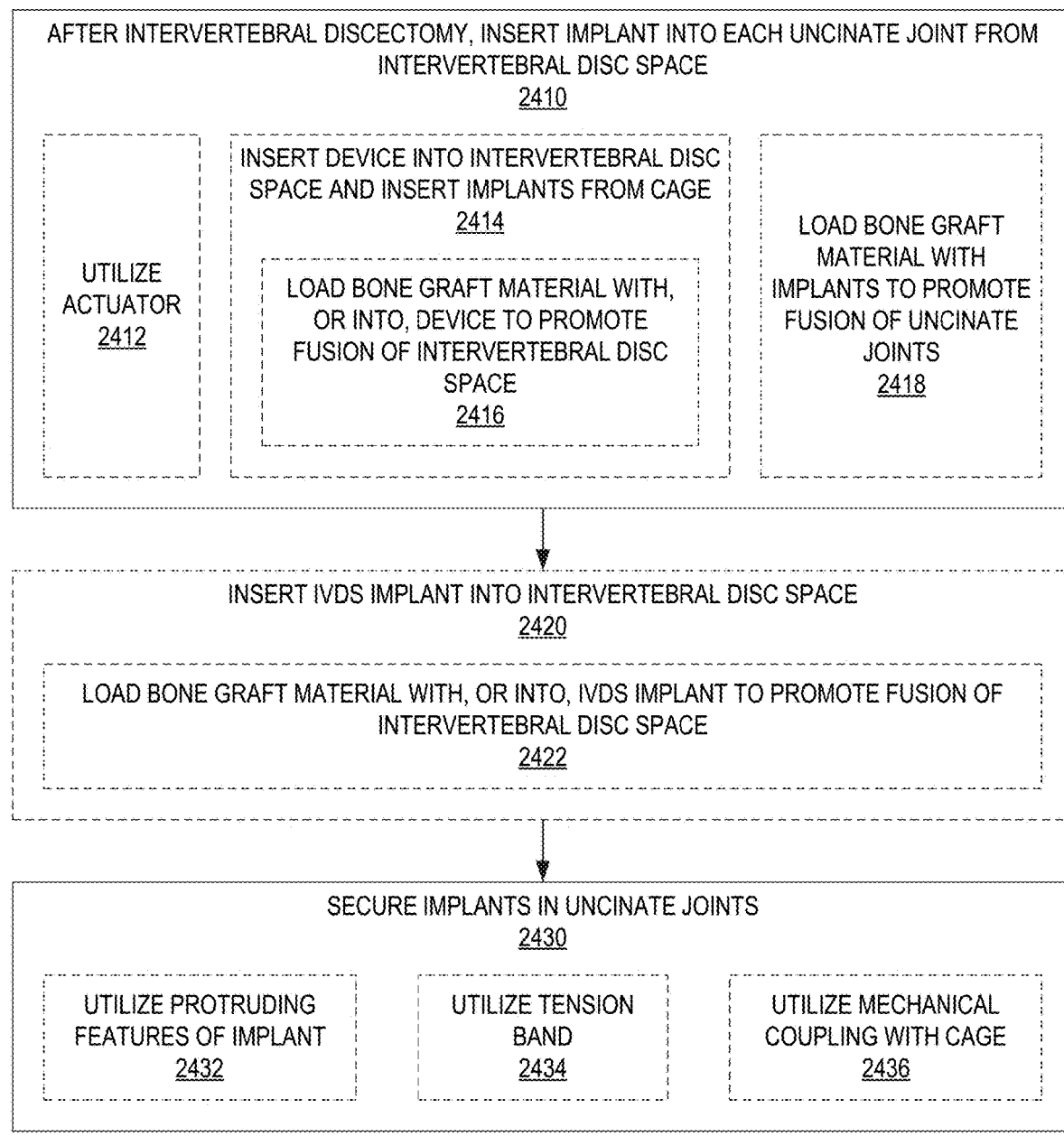
FIG. 24 illustrates a method of stabilizing the uncinate joints of a cervical spine segment after intervertebral discectomy of the cervical spine segment, according to an embodiment.

FIG. 24 illustrates one exemplary method 2400 of stabilizing uncinate joints 120 of a cervical spine segment 180 (FIG. 1) after intervertebral discectomy of cervical spine segment 180. Method 2400 accesses uncinate joints 120 from intervertebral disc space 140 along medial-to-lateral directions 220. Method 2400 may be incorporated into method 2300 (FIG. 23) to implement step 2370 and, optionally, step 2360.

In a step 2410, a pair of implants 100 are inserted from intervertebral disc space 140 into the pair of uncinate joints 120, respectively. Exemplary embodiments of implant 100, which are compatible with step 2410, are discussed below in reference to FIGS. 25A-28, 32A-36F, and 41-43.

In one embodiment, step 2410 includes a step 2412 of utilizing an actuator to insert implants 100 into uncinate joints 120 from intervertebral disc space 140. Step 2412 is similar to step 2222 of method 2200 (FIG. 22) and may be performed as discussed in reference to step 2222.

In another embodiment, step 2410 includes a step 2414 of inserting an IVDS implant into intervertebral disc space 140 and inserting implants 100 from this IVDS implant into uncinate joints 120. This IVDS implant may be non-load bearing or partial-load bearing, as discussed in reference to FIG. 22. Examples of IVDS implants, which are compatible with step 2414, are discussed below in reference to FIGS. 53 and 54. In one implementation, step 2414 includes a step 2416 of loading bone graft material, with, or into, the IVDS implant to promote fusion of cervical spine segment 180 within intervertebral disc space 140. In one example of step 2416, the IVDS implant has at least one void capable of accommodating bone graft material. Bone graft material may be loaded into the void(s) before or after inserting the IVDS implant into intervertebral disc space 140. In another example of step 2416, the IVDS implant is or includes a porous element substantially composed of bone graft material.

Optionally, step 2410 includes a step 2418 of loading bone graft material with, or into, implants 100 to promote fusion of uncinate joints 120. In one example of step 2410, implants 100 have at least one void that carry bone graft material. Bone graft material may be loaded into the void(s) of each implant 100 before or after inserting implant 100 into uncinate joint 120. In another example of step 2410, at least a portion of each implant 100 is a porous portion substantially composed of bone graft material that promotes bone growth in the pores thereof. Since the surfaces of uncinate joints 120 are cortical bone, fusion promoted by step 2410 may be stronger and/or faster than fusion within intervertebral disc space 140. Method 2400 may implement step 2418 together with step 2416 to achieve fusion strength and/or speed superior to that possible when fusing only intervertebral disc space 140.

Embodiments of method 2400, which do not include step 2414, may include a step 2420 of inserting an IVDS implant into intervertebral disc space 140. Step 2420 is similar to step 2250 of method 2200 and may be performed as discussed in reference to step 2250.

Method 2400 further includes a step 2430 of securing implants 100 in uncinate joints 120. In one implementation, step 2430 includes a step 2432 of securing each implant 100 in the corresponding uncinate joint 120 using one or more protruding features of implant 100 to grip at least one of superior surface 684 (FIG. 6B) and inferior surface 686, and thus securing implant 100 in uncinate joint 120. Exemplary protruding features include barbs, ribs, and surface texture. Exemplary implants compatible with step 2432 are discussed below in reference to FIGS. 25A-D, 27, 36A-F, and 41. Step 2430 may include a step 2434, wherein a tension band is utilized to secure each implant 100 to the corresponding uncinate joint 120. In certain embodiments, step 2430 includes a step 2436 of utilizing mechanical coupling with an IVDS implant inserted into intervertebral disc space 140 in step 2414 or step 2420. Step 2436 may utilize a non-load bearing or partial-load bearing IVDS implant, as discussed in reference to FIG. 22. FIGS. 38-47 discussed below illustrate exemplary embodiments of implant 100 and exemplary IVDS implants, which are compatible with step 2436. In embodiments of method 2400, which implement steps 2422 and 2436, step 2422 may be performed after step 2436, without departing from the scope hereof.

Method 2200 may implement two or more of steps 2432, 2434, and 2436 in combination. Without departing from the scope hereof, method 2200 may perform step 2430 as an integrated element of step 2410 and/or step 2420.

Figure 25A:
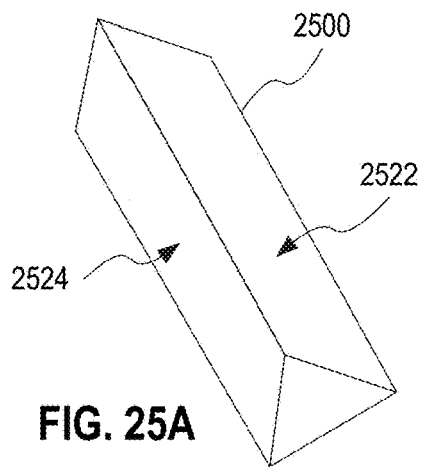
FIGS. 25A, 25B, 25C, and 25D illustrate a tapered implant for stabilizing an uncinate joint, according to an embodiment.
Figure 25B:
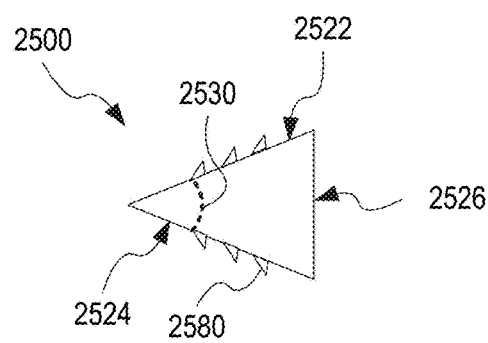
Figure 25C:
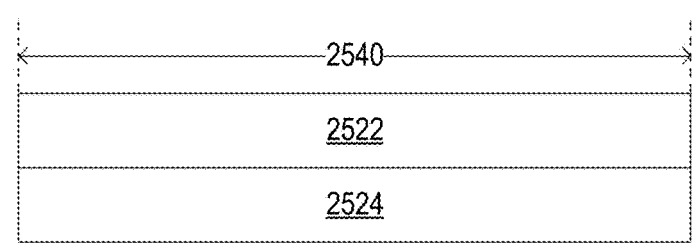
Figure 25D:
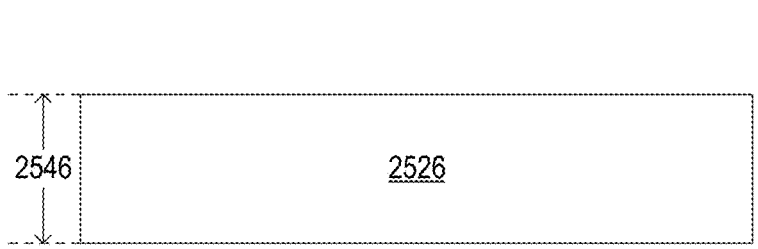

FIGS. 25, 25B, 25C, and 25D illustrate one exemplary tapered implant 2500 for stabilizing uncinate joint 120 (FIG. 1). Tapered implant 2500 is an embodiment of implant 100 (FIG. 1). Tapered implant 2500 may be implemented in method 2200 (FIG. 22), in method 2300 (FIG. 23) as the trial implant or the implant of step 2370, or in method 2400 (FIG. 24). Tapered implant 2500 may also be implemented in the methods discussed below in reference to FIGS. 37A-38 and 49-52. FIG. 25A shows tapered implant 2500 in perspective view. FIG. 25B shows tapered implant 2500 in cross-sectional side view. FIGS. 25C and 25D are elevation views of tapered implant 2500 from directions in the plane of the cross-sectional view of FIG. 25B. FIGS. 25A-D are best viewed together.

Tapered implant 2500 includes two surfaces 2522 and 2524 forming a taper with a taper angle of 2530. Taper angle 2530 is, for example, in the range between 10° and 45°, or in the range between 5° and 60°. Taper angles 2530 less than 5°-10°, may result in insufficient distraction of uncinate joints 120, while taper angles 2530 greater than 45°-60° may result in insufficient support of uncinate joint 120 and/or trouble securing tapered implant 2500 in uncinate joint 120. Tapered implant 2500 is configured to be placed in uncinate joint 120 with surfaces 2522 and 2524 contacting superior surface 684 (FIG. 6B) and inferior surface 686 of uncinate joint 120. Tapered implant 2500 includes a surface 2526 generally facing intervertebral disc space 140, when tapered implant 2500 is located in uncinate joint 120.

Tapered implant 2500 has length 2540. When placed in uncinate joint 120, length 2540 is oriented along uncinate joint 120 substantially along anterior-to-posterior direction 210. In one example, length 2540 is at least six millimeters, for example, to provide sufficient contact area, between tapered implant 2500 and surfaces of uncinate joint 120, such that tapered implant 2500 is capable of supporting the load of uncinate joint 120. Length 2540 is at most eighteen millimeters, for example, to ensure that tapered implant 2500 does not encroach on the neural foramen. In another example, length 2540 is such that tapered implant 2500 protrudes from uncinate joint 120 in the anterior direction to easy coupling of tapered implant 2500 with another device, such as the actuator or extensions discussed in reference to FIGS. 23 and 24. In this example, length 2540 may be in the range between 15 and 70 millimeters.

When implemented in method 2200, 2300, or 2400, or the methods discussed below in reference to FIGS. 37A-38 and 49-52, tapered implant 2500 is inserted into uncinate joint 120 with the taper (characterized by taper angle 2530) facing uncinate joint 120 (i.e., with surfaces 2522 and 2524 facing uncinate joint 120 and surface 2526 facing away from uncinate joint 120). Tapered implant 2500 has a maximum thickness 2546. Maximum thickness 2546 exceeds the spacing between superior surface 684 and inferior surface 686 at the locations where tapered implant 2500 contacts superior surface 684 and inferior surface 686, such that tapered implant 2500 is capable of distracting uncinate joint 120. In one embodiment, the value of maximum thickness 2546 is sufficiently large that maximum thickness 2546 exceeds a desired spacing between superior surface 684 and inferior surface 686, at the locations where tapered implant 2500 contacts superior surface 684 and inferior surface 686, for the vast majority of patients 170. This embodiment of tapered implant 2500 is suitable for use with the vast majority of patients 170 without requiring customization or custom size selection. In one example, maximum thickness 2546 is in the range between four and ten millimeters, to provide sufficient distraction of uncinate joint 120 to relieve impingement issues while fitting between cervical vertebrae 184 and 186. In another example, maximum thickness 2546 is no greater than six millimeters. In yet another example, maximum thickness 2546 is greater than two millimeters.

In certain embodiments, tapered implant 2500 includes features 2580 that protrude from surfaces 2522 and 2524 and/or form fenestrations in surfaces 2522 and 2524. Each of methods 2200, 2300, and 2400 may utilize features 2580 in steps 2232, 2332, and 2432, respectively, to secure tapered implant 2500 in uncinate joint 120. Features 2580 may be barbs, ribs, surface texture, and/or fenestrations. For clarity of illustration, features 2580 are not shown in FIGS. 25A and 25C. Embodiments of tapered implant 2500 that include features 2580 may be self-securing.

Although not shown in FIGS. 25A-D, tapered implant 2500 may have at least one void capable of accommodating bone graft material, without departing from the scope hereof. Such embodiments of tapered implant 2500 may be utilized in step 2224 of method 2200, in step 2370 of method 2300, and in step 2418 of method 2400. Tapered implant 2500 may include a coating, for example a hydroxyapatite coating, to achieve improved fixation of tapered implant 2500 to uncinate joint 120, without departing from the scope hereof.

In one embodiment, tapered implant 2500 is substantially composed of a metal such as titanium, titanium alloy, stainless steel, cobalt, chromium, or a combination thereof. In another embodiment, tapered implant 2500 includes a porous portion with pores capable of accommodating bone graft material within uncinate joint 120, or a porous portion substantially composed of bone graft material, as discussed in reference to step 2224 of method 2200, in step 2370 of method 2300, and in step 2418 of method 2400. In one example, tapered implant 2500 is substantially composed of, or includes, porous metal. In yet another embodiment, tapered implant 2500 is substantially composed of allograft bone. In a further embodiment, tapered implant 2500 is substantially composed of polymer. The polymer is, for example, polyetheretherketone (PEEK) or another polyaryletherketone (PAEK) polymer. Any of the above materials may be used in a 3-D printing process to make tapered implant 2500.

Although not shown in FIGS. 25A-D, tapered implant 2500 may further be tapered along the dimension associated with length 2540 to account for the lordosis of the cervical spine, as discussed in reference to threaded implant 500 (FIGS. 5A and 5B), without departing from the scope hereof.

Figure 26:
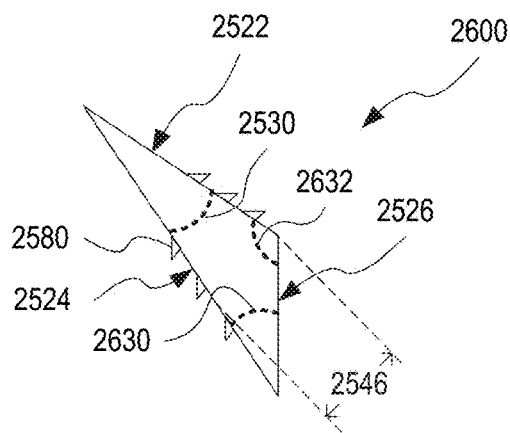
FIG. 26 illustrates another tapered implant for stabilizing an uncinate joint, according to an embodiment.

FIG. 26 illustrates another exemplary tapered implant 2600 for stabilizing uncinate joint 120. Tapered implant 2600 is similar to tapered implant 2500, except that angle 2630 between surfaces 2524 and 2526 is less than angle 2632 between surface 2522 and 2526.

Figure 27:
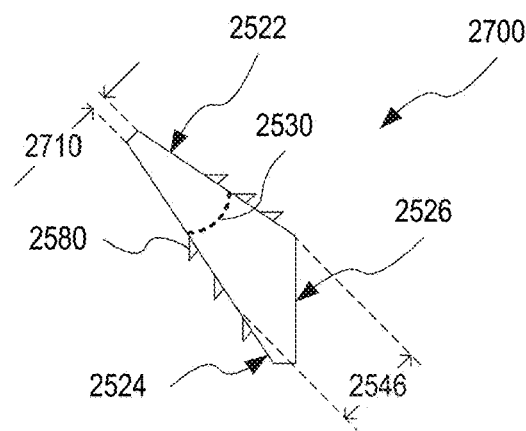
FIG. 27 illustrates yet another tapered implant for stabilizing an uncinate joint, according to an embodiment.

FIG. 27 illustrates yet another exemplary tapered implant 2700 for stabilizing uncinate joint 120. Tapered implant 2700 is similar to tapered implant 2600, except that the corner formed by surfaces 2522 and 2524 is truncated, and the corner formed by surfaces 2524 and 2526 is truncated. Tapered implant 2700 has a minimum thickness 2710. Minimum thickness 2710 may be sufficiently small that tapered implant 2700 can enter uncinate joint 120 for the vast majority of patients 170. Minimum thickness 2710 is in the range between 0.5 and 2 millimeters, for example.

Figure 28:
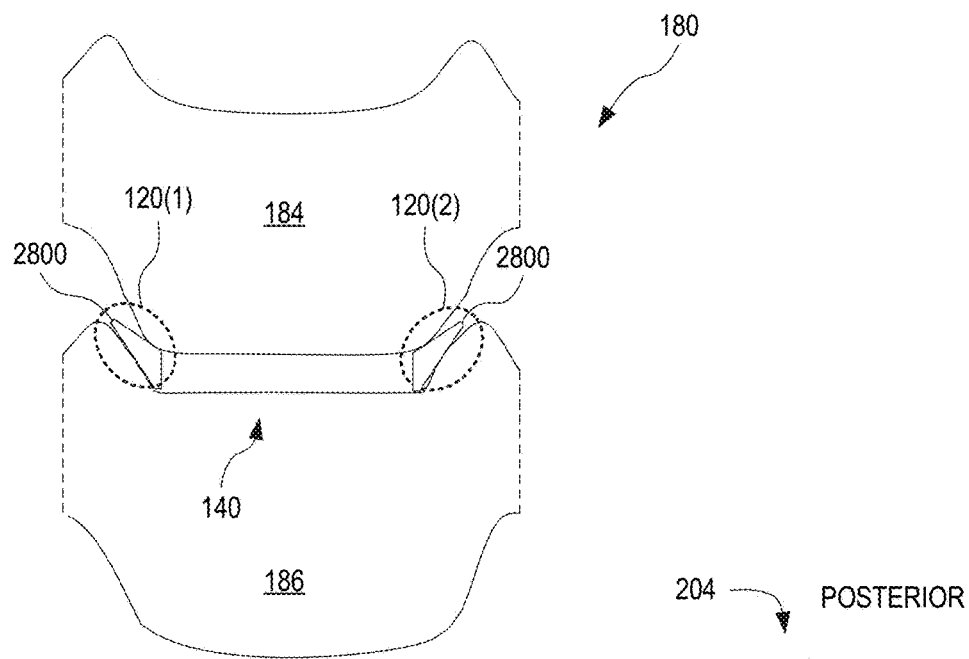
FIG. 28 illustrates, in an anterior view, a pair of tapered implants located in the uncinate joints of a cervical spine segment, after insertion into the uncinate joints according to the method of FIG. 22, the method of FIG. 23, or the method of FIG. 24, according to an embodiment.

FIG. 28 illustrates, in an anterior view, a pair of exemplary tapered elements 2800 located in uncinate joints 120 of cervical spine segment 180 (FIG. 1), after insertion into uncinate joints 120 according to method 2200 (FIG. 22), 2300 (FIG. 23), or 2400 (FIG. 24), or according to the methods discussed below in reference to FIGS. 37A-38 and 49-52. Each tapered element 2800 is, for example, one of tapered implants 2500 (FIG. 25), 2600 (FIG. 26), and 2700 (FIG. 27). Tapered element 2800 may be used as a trial implant and/or as a distractor tip that at least partly distracts uncinate joint 120. Embodiments of tapered element 2800 serving as trial implant or distractor tip may be disposable.

Figure 29:
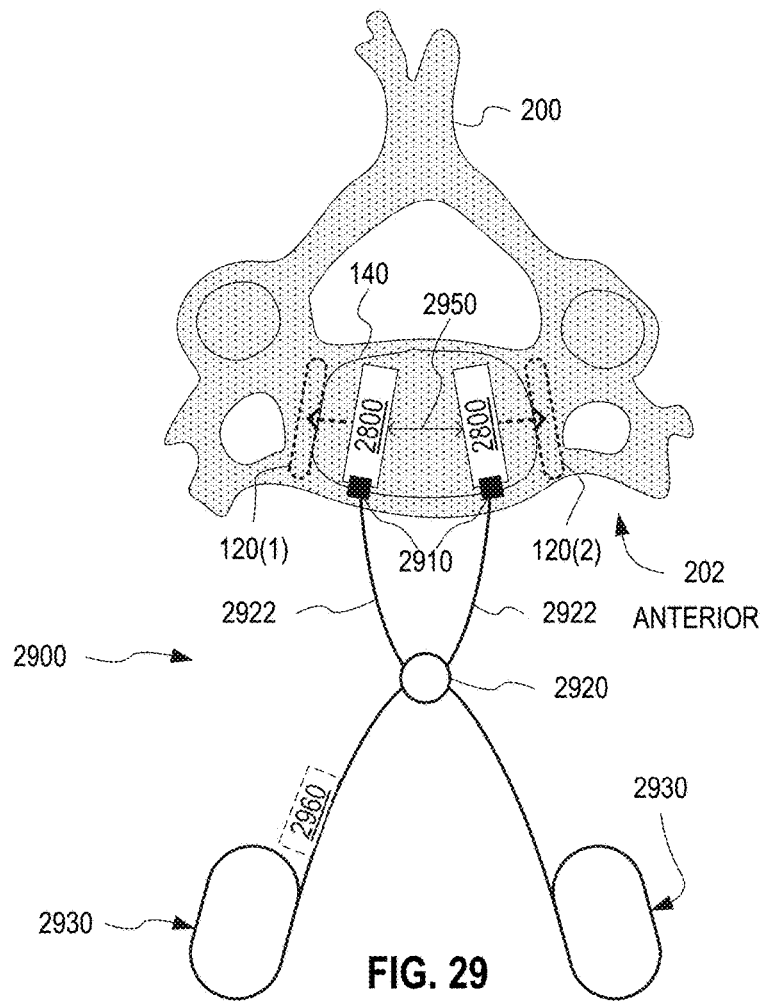
FIG. 29 illustrates, in an axial view, an actuator for inserting tapered implants into the uncinate joints of a cervical spine segment, according to an embodiment.

FIG. 29 illustrates, in an axial view, one exemplary actuator 2900 for inserting tapered elements 2800 (FIG. 28) into uncinate joints 120 of cervical spine segment 180 (FIG. 1). Actuator 2900 may be utilized by methods 2200 (FIG. 22), 2300 (FIG. 23), and 2400 (FIG. 24). Together, actuator 2900 and tapered elements 2800 form a system for distracting uncinate joints 120. In one example of use, tapered elements 2800 are final implants left in cervical spine segment 180 to stabilize cervical spine segment 180. In another example of use, tapered elements 2800 are trial implants, and actuator 2900 and tapered elements 2800 may cooperate to perform step 2320 of method 2300. In this example of use, tapered elements 2800, or portions of tapered elements 2800 contacting a surface of uncinate joints 120, may be made of a polymer. In a more general embodiment, tapered elements 2800 are made of one or more of the materials discussed above in reference to threaded implant 500. Any one of these materials may be used to make tapered element 2800 in a 3-D printing process.

Actuator 2900 includes a hinge 2920, handles 2930, and two connector arms 2922 connecting hinge 2920 to two respective tapered elements 2800. For the purpose of coupling with actuator 2900, each tapered element 2800 includes a coupling interface 2910. A surgeon may manipulate handles 2930 to control the position of tapered elements 2800 through hinge 2920, to move tapered elements 2800 within cervical spine segment 180 along medial-to-lateral directions 220 (FIG. 2). In one embodiment, hinge 2920 is configured for scissor action, such that tapered elements 2800 move towards uncinate joints 120 when handles 2930 are moved away from each other. In another embodiment, hinge 2920 is configured for reverse scissor action, such that tapered elements 2800 move towards uncinate joints 120 when handles 2930 are towards each other.

Optionally, actuator 2900 includes a dial 2960 that indicates, to the surgeon, distance 2950 between tapered elements 2800 or another measure related to distance 2950. With knowledge of the shape of tapered elements 2800, other information may be derived from distance 2950, such as the spacing between superior surface 684 (FIG. 6B) and inferior surface 686. If, furthermore, a known force is applied to handles 2930, forces associated with distraction of uncinate joints 120 may be derived from distance 2950. In one example of use of dial 2960, actuator 2900 is implemented in step 2320 of method 2300 (FIG. 23) to obtain information about uncinate joints 120 and/or distraction of uncinate joints 120. This information may be utilized in step 2410 of method 2400 (FIG. 24), for example to select implants of suitable geometry for cervical spine segment 180 of patient 170. In one implementation, a surgeon utilizes dial 2960 to actuate handles 2930. In this implementation, dial 2960 may be configured to be operable in discrete increments that each corresponds to a known change of distance 2950. For example, each increment of dial 2960 corresponds to a change of distance 2950 by 0.5 or 1.0 millimeters.

Although not shown in FIG. 29, tapered elements 2800 may have length 2540 (FIG. 25C) sufficient to extend beyond uncinate joints 120 in an anterior direction, when tapered elements 2800 are placed in uncinate joints 120, without departing from the scope hereof.

In addition to inserting implants 100 into uncinate joints 120, actuator 2900 may serve to maintain anterior access to intervertebral disc space 140, by holding aside the esophagus, muscles, and other tissue of patient 170, for example in a manner similar to that discussed below in reference to FIGS. 32A-37A.

Actuator 2900 may also be used to insert, into uncinate joints 120, distractor tips, trial implants, and uncinate joint stabilizers that are different from tapered elements 2800. For example, actuator 2900 may, instead of inserting tapered elements 2800, insert distractor tips, trial implants, and uncinate joint stabilizers discussed below in reference to FIGS. 32A, 32B, and 36A-F.

Figure 30:
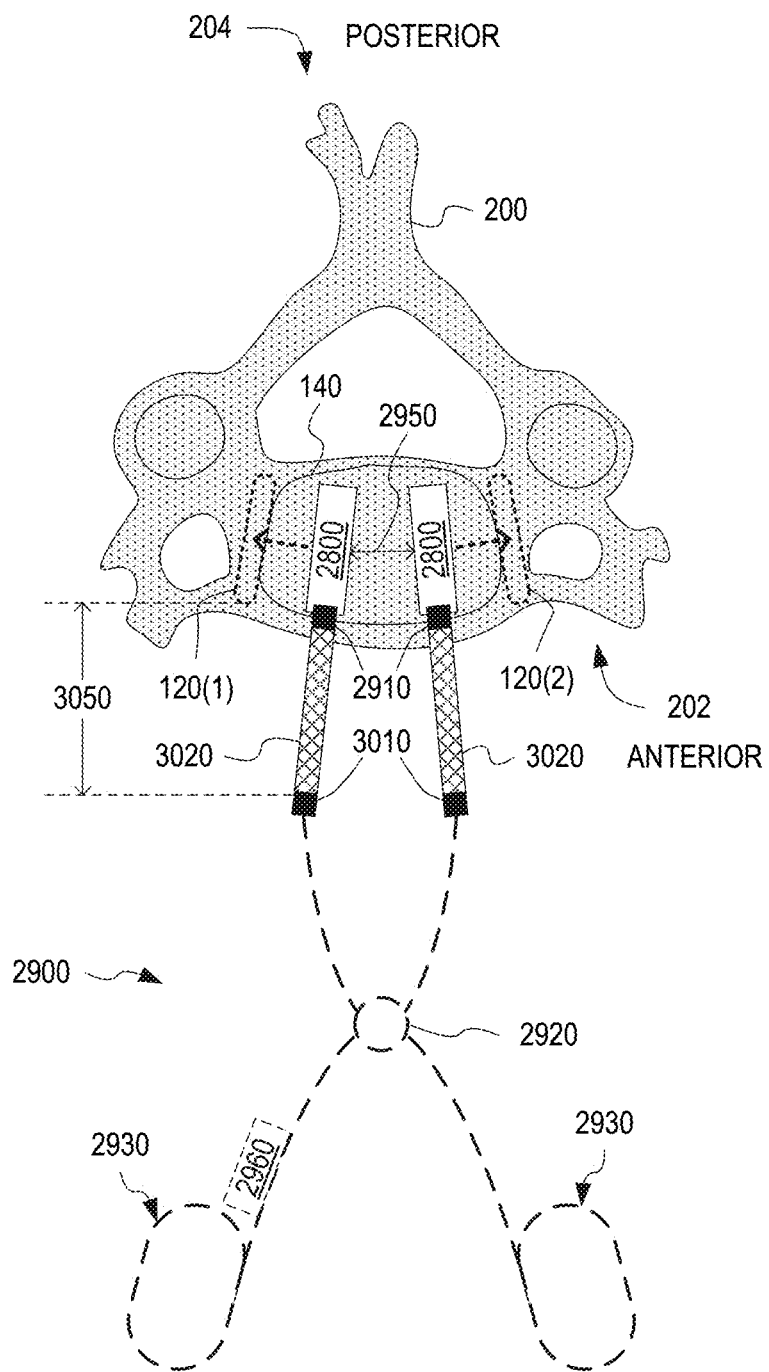
FIG. 30 illustrates, in an axial view, extensions that may be coupled with tapered implants to extend the tapered implants in an anterior direction, according to an embodiment.

FIG. 30 illustrates, in an axial view, exemplary extensions 3020 that may be coupled with tapered elements 2800 (FIG. 28) to extend tapered elements 2800 in an anterior direction. Extensions 3020 may be used by methods 2200 (FIG. 22), 2300 (FIG. 23), and 2400 (FIG. 24).

Each extension 3020 has length 3050. Length 3050 is in the range between 20 and 60 millimeters, for example. Each extension 3020 couples to coupling interface 2910 of tapered element 2800. Optionally, each extension 3020 includes a coupling interface 3010, such that extensions 3020 may be coupled with actuator 2900 (FIG. 29).

Actuator 2900 may be coupled with extensions 3020 to serve as a soft tissue retractor for the surgery, with or without tapered elements 2800 coupled therewith.

FIG. 31A illustrates another exemplary actuator 3100. Actuators 2900 and 3100 may be applied interchangeably throughout the present disclosure. Actuator 3100 includes two connector arms 3110 and a link 3120 onto which connector arms 3110 are mounted. Distal ends 3112 of connector arms 3110 are configured to couple to tapered elements 2800, or to other distractor tips, trial implants, or uncinate joint stabilizers such as those discussed below in reference to FIGS. 32A, 32B, and 36A-F. At least one of connector arms 3110 is capable of being translated along link 3120 (as indicated by arrow 3150) to change distance 3160 between connector arms 3110. FIG. 31A shows connector arm 3110(1) as being in a fixed position relative to link 3120 and connector arm 3110(2) as being allowed to translate along link 3120. However, without departing from the scope hereof, both of connector arms 3110(1) and 3110(2) may be capable of being translated along link 3120. The role of the joint(s) between connector arm(s) 3110 and link 3120 is similar to that of hinge 2920 of actuator 2900.

In an embodiment, actuator 3100 includes a control 3130 for adjusting and/or locking distance 3160 between connector arms 3110. The role of control 3130 is similar to that of handles 2930 and/or dial 2960, of actuator 2900. In one example, control 3130 is a fastener that may be fastened to lock the position of a respective connector arm 3110 relative to link 3120. In another example, control 3130 may be activated to translate one of connector arms 3110. Actuator 3100 may further include dial 2960.

Referring now to FIGS. 29 and 31A in combination, the role of handles 2930, and optionally dial 2960, as implemented in actuator 2900 is similar to that of control 3130, and optionally dial 2960, as implemented in actuator 3100.

FIG. 31B illustrates an actuator 3170 with mutually converging connector arms 3172(1) and 3172(2). Actuator 3170 is an embodiment of actuator 3100, and connector arms 3172(1) and 3172(2) are embodiments of connector arms 3110(1) and 3110(2). At least a distal portion 3174 of each connector arm 3172 is angled inwards (toward the other connector arm 3172) by an angle 3178. In one implementation, angle 3178 is such that the orientation of distal portions 3174 approximately matched the orientation of the mutually converging uncinate joints 120. In an example, angle 3178 is in the range between 5 and 30 degrees. Without departing from the scope hereof, each connector arm 3172 may be oriented at angle 3178 along the full distance from link 3120 to distal end 3112. Angle 3178 may be adjustable.

FIG. 31C is a lateral view of actuator 3100 or actuator 3170, as seen from the direction indicated by arrow 3102 in FIGS. 31A and 31B. Connector arm 3110/3172 has height 3118 in the axial dimension when distal ends 3112 are substantially anterior facing. In one embodiment, height 3118 is sufficient for connector arm 3110/3172 to retract soft tissue anterior to cervical spine segment 180. In this embodiment, each of actuators 3100 and 3170 may function as an integrated soft-tissue-retractor and uncinate-joint-distractor tool. In cooperation with a pair of tapered elements 2800 or a pair of other distractor tips, trial implants, and uncinate joint stabilizers (such as those discussed below in reference to FIGS. 32A, 32B, and 36A-F) this integrated soft-tissue-retractor and uncinate-joint-distractor tool is capable of both (a) distracting uncinate joints 120 of cervical spine segment 180 and (b) retracting soft tissue anterior of cervical spine segment 180 to provide access to cervical spine segment 180. In one example compatible with soft-tissue retraction, height 3118 is at least 5 millimeters, for example between one and five centimeters.

Without departing from the scope hereof, a portion of connector arm 3110/3172 may have height 3118 sufficient to distract soft tissue, while another portion of connector arm 3110/3172 is characterized by a smaller height 3118. Even so, connector arm 3110/3172 may still be capable of retracting soft tissue anterior to cervical spine segment 180 to provide access to cervical spine segment 180.

Referring now to FIG. 29, at least a portion of each connector arm 2922 may have height 3118, such that actuator 2900 may be used to distract uncinate joints 120 as well as retract soft tissue anterior of cervical spine segment 180 to provide access to cervical spine segment 180. Similarly, in reference to FIG. 30, at least a portion of each extension 3020 may implement height 3118 sufficient to, in cooperation with actuator 2900, retract soft tissue anterior to cervical spine segment 180 to provide access to cervical spine segment 180.

In certain embodiments of actuator 2900 actuator 3100, and actuator 3170, the connector arms may have retractor blades mounted thereto for retraction of soft tissue. Similarly, embodiments of extensions 3020 may have retractor blades mounted thereto for retraction of soft tissue.

FIG. 31D is a lateral view of a connector arm 3182 that is angled to position link 3120, and optionally control 3130 and/or dial 2960 away from the space anterior of cervical spine segment 180. Connector arm 3182 represents an embodiment of connector arm 3110 and an embodiment of connector arm 3172. When distal ends 3112 are at cervical spine segment 180 and are substantially anterior facing, connector arms 3182 places the bulk of actuator 3100 or 3170 (e.g., link 3120, optional control 3130, and optional dial 2960) away from an anterior line of sight to cervical spine segment 180, the potentially providing improved physical and imaging access to cervical spine segment 180. Connector arm 3182 includes a distal segment 3184 and a proximate segment 3186 oriented at an angle 3188 to each other. Angle 3188 is, for example, in the range between 70 and 140 degrees. Angle 3188 may be adjustable. Distal segment 3184 has height 3118, as discussed above in reference to FIG. 31C.

Figure 32A:
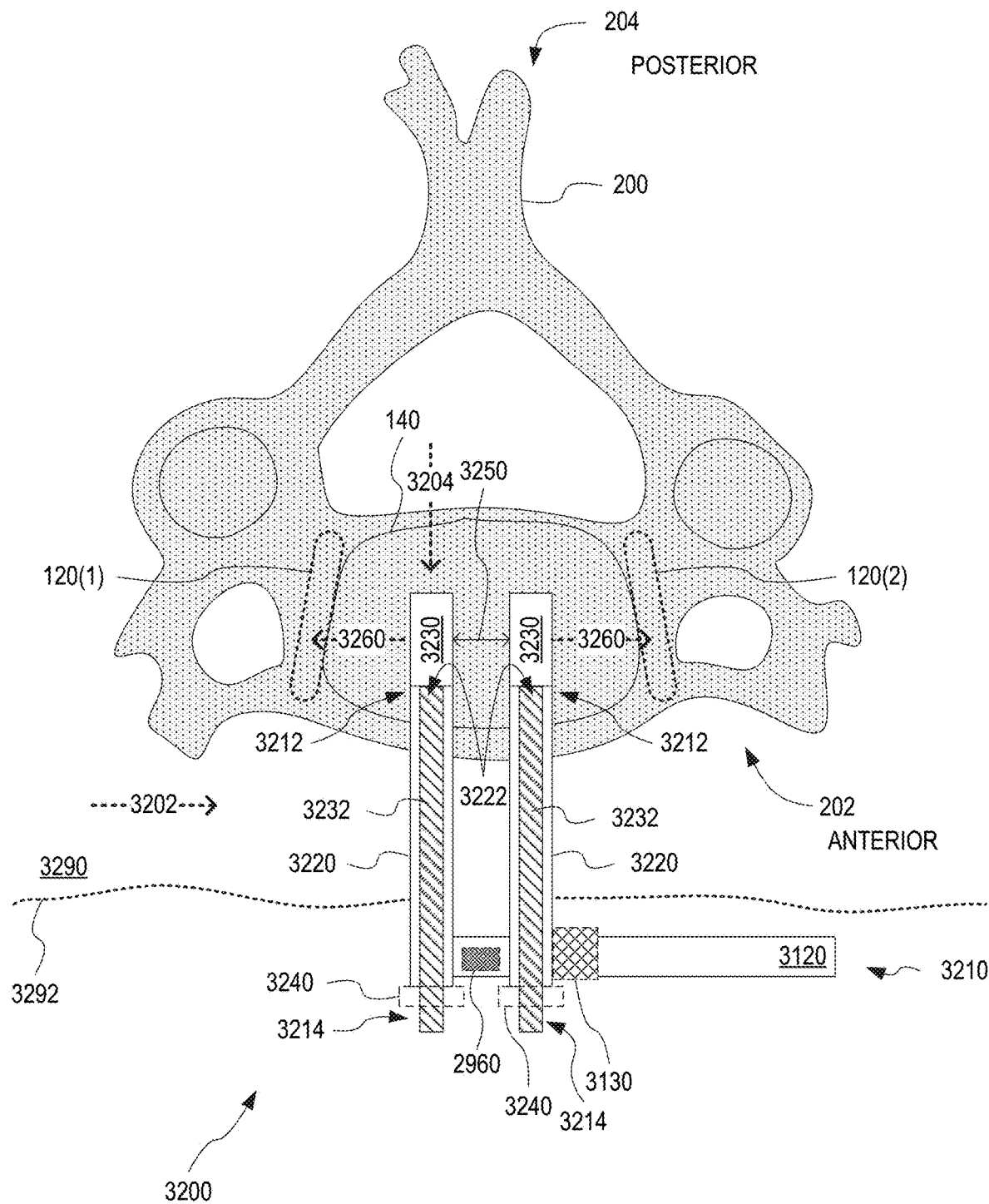
FIGS. 32A and 32B illustrate a system for distraction of uncinate joints 120 of cervical spine segment 180 and/or insertion of implants into uncinate joints 120, according to an embodiment.
Figure 32B:
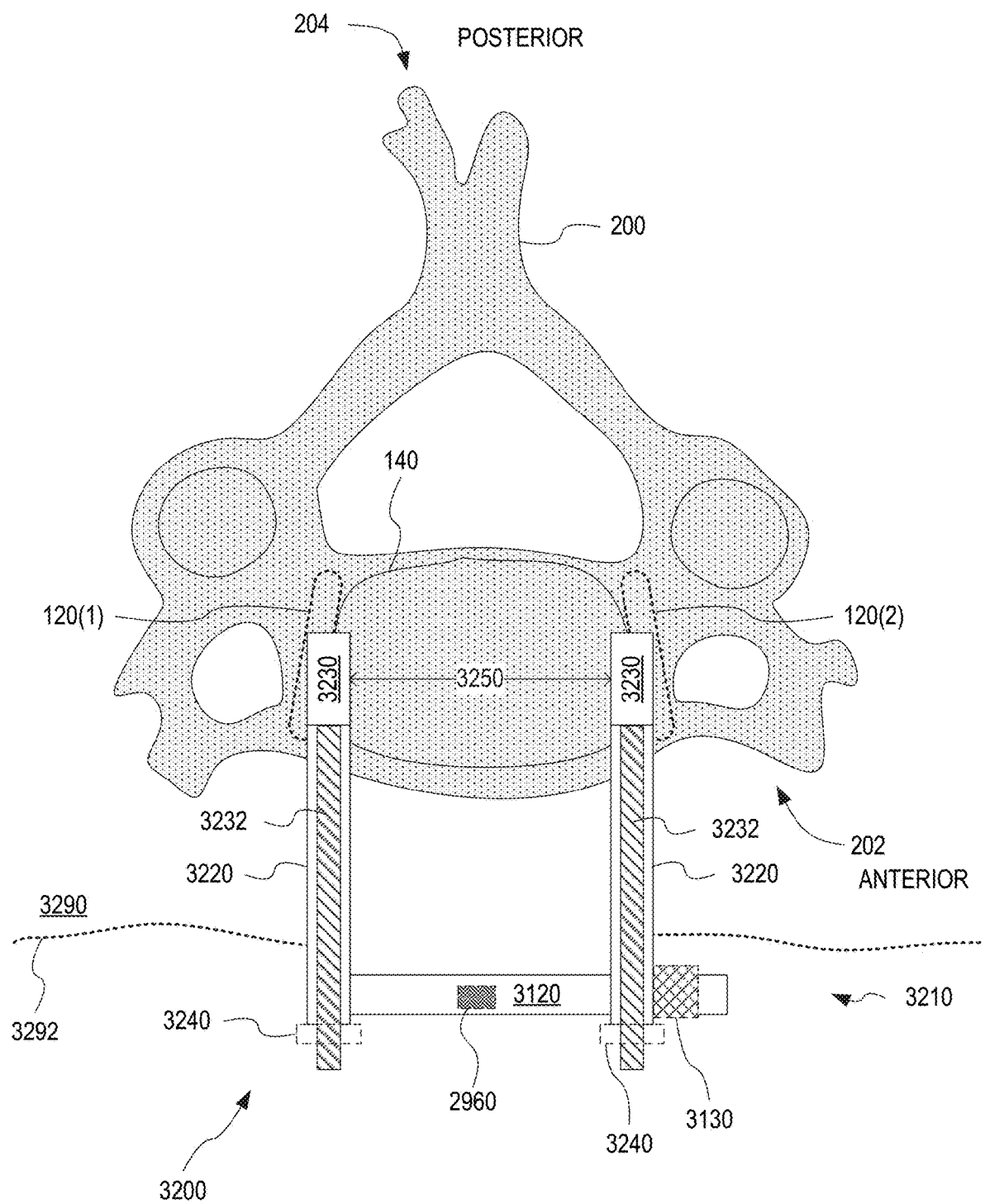

FIGS. 32A and 32B illustrate one exemplary system 3200 for distraction of uncinate joints 120 of cervical spine segment 180 and/or insertion of implants into uncinate joints 120. In certain embodiments, system 3200 is further capable of retracting soft tissue 3290 anterior to cervical spine segment 180. FIGS. 32A and 32B show the configuration of system 3200 at two different stages during exemplary use of system 3200. FIGS. 32A and 32B are best viewed together.

System 3200 includes an actuator 3210. As depicted in FIGS. 32A and 32B, actuator 3210 is an embodiment of actuator 3100. Actuator 3210 implements connector arms 3110 as connector arms 3220, respectively. Each connector arm 3220 forms a receptacle 3222 configured to hold an extension 3232 coupled to a tip 3230, such that tip 3230 is beyond the distal end 3212 of connector arm 3220. Actuator 3210 is capable of changing the distance 3250 between connector arms 3220. Without departing from the scope hereof, system 3200 may instead be based on an embodiment of actuator 2900, with connector arms 2922 implemented as connector arms 3220.

Tip 3230 may be a distractor tip, a trial implant, or an uncinate joint stabilizer. Tip 3230 may be similar to tapered element 2800. Alternatively, tip 3230 is another distractor tip, trial implant, or uncinate joint stabilizers (such as those discussed below in reference to FIGS. 32A, 32B, and 36A-F). Tips 3230 may be disposable. Extensions 3232 may also be disposable. Tips 3230 and extensions 3232 may be made from metal or a polymer (such as plastic). In one embodiment, each pair of tip 3230 and extension 3232 are integrally formed. In another embodiment, each tip 3230 is removably connected to the corresponding extension 3232. In this embodiment, tips 3230 may be decoupled from extensions 3232 and left in uncinate joints 120, after extraction of actuator 3210 and extensions 3232 from patient 170, to function as uncinate joint stabilizers. Also in this embodiment, it is possible to replace each tip 3230 with another tip 3230 without removing extensions 3232 from receptacles 3222. In one example of this embodiment, extension 3232 is threaded onto tip 3230.

System 3200 may include tips 3230 and extensions 3232. Optionally, system 3200 is provided with tips 3230 connected to extensions 3232 and extensions 3232 preloaded in receptacles 3222. Alternatively, actuator 3210 may be provided as a standalone tool configured to cooperate with tips 3230 and extensions 3232, for example provided by a third party.

In one use scenario, the surgeon inserts connector arms 3220, with tips 3230 coupled thereto via extensions 3232, into an incision in patient 170 anterior of cervical spine segment 180. The surgeon positions tips 3230 in intervertebral disc space 140 (see FIG. 32A). Next, the surgeon manipulates actuator 3210 to increase distance 3250 between connector arms 3220, thereby pushing tips 3230 into uncinate joints 120 (see FIG. 32B) along medial-to-lateral directions 3260 (indicated in FIG. 32A). Connector arms 3220, or retractor blades mounted thereto, may retract soft tissue 3290 anterior to cervical spine segment 180 by forcing soft tissue 3290 laterally outwards. When distraction of uncinate joints 120 is no longer needed, the surgeon may remove tips 3230, extensions 3232, and actuator 3210 from patient 170.

In another use scenario, the surgeon performs a similar procedure with trial implants. In this scenario, the surgeon may read dial 2960 while the trial implants are in uncinate joints 120 to obtain a measure of the optimal size of implants to be used as uncinate joint stabilizers before extracting the trial implants from cervical spine segment 180. Also in this example, the surgeon may use the trial implants to at least partly distract uncinate joints 120, to eliminate the need for a separate distraction process prior to insertion of the trial implants into uncinate joints 120.

In yet another use scenario, the surgeon uses uncinate joint stabilizers in the place of tips 3230 and leaves the uncinate joint stabilizers in uncinate joints 120. In this scenario, the surgeon may also use the uncinate joint stabilizers to at least partly distract uncinate joints 120, to eliminate the need for a separate distraction process prior to insertion of the uncinate joint stabilizers into uncinate joints 120.

In the embodiment shown in FIGS. 32A and 32B, distal ends 3214 of extensions 3232 are accessible to the surgeon anterior to the skin 3292 of patient 170. This allows the surgeon to, if necessary, exert control directly on extensions 3232, for example to adjust the orientation of tips 3230 about the axis of respective connector arms 3220.

In one embodiment, each extension 3232 has rotational symmetry about its longitudinal axis, i.e., the axis parallel to direction 3204 (FIG. 32A). In this embodiment, extension 3232 may be rotated in receptacle 3222, for example to adjust the corresponding orientation of tip 3230 and/or to allow tip 3230 to roll into uncinate joint 120 from intervertebral disc space 140. Alternatively, extension 3232 may lack rotational symmetry but receptacle 3222 nevertheless permits rotation of extension 3232 about the longitudinal axis of connector arm 3220. In another embodiment, extension 3232 does not have rotational symmetry about its longitudinal axis, and receptacle 3222 is configured to lock the orientation of extension 3232 about its longitudinal axis, so as to lock the corresponding orientation of tip 3230.

In certain embodiments, system 3200 is configured to allow rotation of extension 3232 about the longitudinal axis of connector arm 3220, and system 3200 further includes, or is configured to cooperate with, a pair of rotation controls 3240. Each rotation control 3240 controls the orientation of a respective extension 3232, and thereby tip 3230, about the longitudinal axis of the respective connector arm 3220 (i.e., the axis parallel to direction 3204 indicated in FIG. 32A). In one such embodiment, each rotation control 3240 enables the surgeon to adjust the orientation of the respective extension 3232 about the longitudinal axis of connector arm 3220, and each rotation control 3240 may include a handle or a grip on the respective extension 3232. In another such embodiment, rotation control 3240 is configured to lock the orientation of extension 3232 about the longitudinal axis of connector arm 3220, and each rotation control 3240 may include a fastener. In yet another such embodiment, each rotation control 3240 enables both adjustment and locking of the orientation of the respective extension 3232 about the longitudinal axis of connector arm 3220. In this embodiment, each rotation control may include a fastener and a grip/handle, optionally integrated with each other.

Actuator 3210 may be provided with rotation controls 3240, or extensions 3232 may be provided with rotation controls 3240.

Without departing from the scope hereof, extensions 3232 may be shorter than shown in FIGS. 32A and 32B. For example, distal ends 3214 of extensions 3232 may be positioned posterior to the couplings between connector arms 3220 and link 3120, optionally posterior to skin 3292. In this example, the surgeon may not have access to distal ends 3214 when extensions 3232 are held in receptacles 3222 of connector arms 3220.

Although not shown in FIGS. 32A and 32B, system 3200 may include, or be configured to cooperate with, a pair of fasteners that lock the position of extensions 3232 in receptacles 3222 to position tips 3230 at a desired distance from distal ends 3212.

Figure 33A:
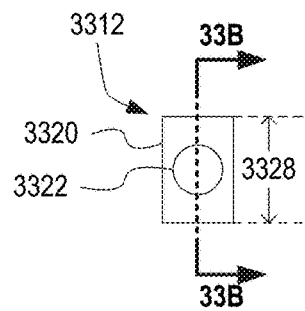
FIGS. 33A-D illustrate exemplary connector arms.
Figure 33B:
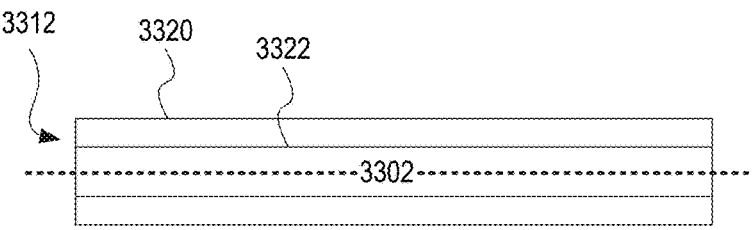

FIGS. 33A and 33B illustrate one exemplary connector arm 3320 for holding tip 3230. Connector arm 3320 is an embodiment of connector arm 3220. FIG. 33A is a posterior end view of a distal end 3312 of connector arm 3320, equivalent to a view of connector arm 3320 along direction 3204 (FIG. 32A) when connector arm 3320 is implemented in system 3200. FIG. 33B is a cross-sectional side view of connector arm 3320, with the cross section taken along line 33B-33B indicated in FIG. 33A. The view of FIG. 33B is equivalent to a lateral view along direction 3302 (FIG. 32A) of connector arm 3320 when implemented in system 3200. FIGS. 33A and 33B are best viewed together.

Connector arm 3320 forms a receptacle 3322 which is an embodiment of receptacle 3222. Receptacle 3322 is a channel through connector arm 3320. The cross section of receptacle 3322, as shown in FIG. 33A, is circular, such that receptacle 3322 does not restrict the orientation of a corresponding extension 3232 about longitudinal axis 3302 of connector arm 3320, when extension 3232 is held in receptacle 3322. Connector arm 3320 has height 3328 in the axial dimension when distal end 3312 is substantially anterior facing. Height 3328 is similar to height 3118.

Although FIG. 33A shows connector arm 3320 as having rectangular cross sections, both in the plane of FIG. 33A and in the plane of FIG. 33B, one or both of these cross sections may be non-rectangular, without departing from the scope hereof. For example, the cross section of connector arm 3320 in the plane of FIG. 33A may be circular, oval, or rectangular with rounded corners.

Figure 33C:
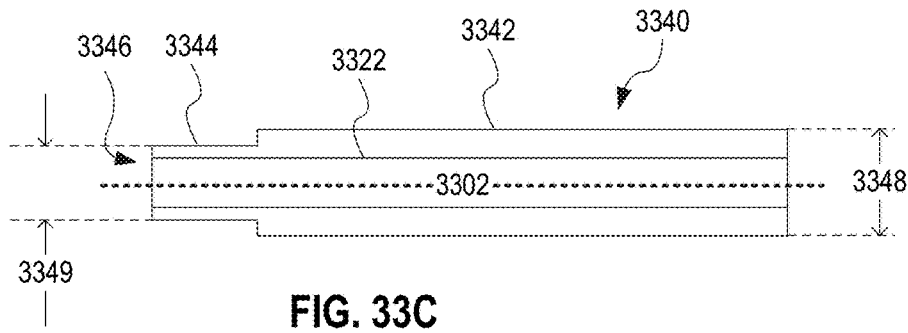

FIG. 33C is a cross-sectional side view of one exemplary connector arm 3340 that has non-uniform height along its longitudinal axis 3302. FIG. 33C shows connector arm 3340 in a view similar to the view of connector arm 3320 in FIG. 33B. Connector arm 3340 is an embodiment of connector arm 3320. Connector arm 3340 is similar to connector arm 3320 except for having non-uniform height along longitudinal axis 3302. A portion 3344 of connector arm 3340 closest to distal end 3346 of connector arm 3340 has height 3349, whereas a portion 3342 of connector arm 3340 further from distal end 3346 has height 3348. Height 3348 is greater than height 3349. Height 3348 may be similar to height 3318. In one implementation, height 3348 is sufficiently large to retract soft tissue 3292, and height 3349 is sufficiently small that distal end 3346 of connector arm 3340 may enter intervertebral disc space 140.

Figure 33D:
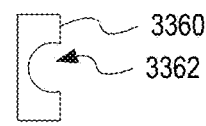

FIG. 33D is a posterior end view of one exemplary connector arm 3360 having a groove 3362. FIG. 33D shows connector arm 3360 in a view similar to the view of connector arm 3320 in FIG. 33A. Connector arm 3360 is an embodiment of connector arm 3220, and groove 3362 is an embodiment of receptacle 3322 that does not fully enclose extension 3232 but wraps around extension 3232 sufficiently to hold extension 3232. In an alternate embodiment, not shown in FIG. 33D, groove 3362 does not wrap sufficiently around extension 3232 to hold extension 3232. In this embodiment, groove 3362 holds extension 3232 with the aid of one or more additional fastening mechanisms, such as one or more brackets affixed to connector arm 3360 and securing extension 3232 in groove 3362.

Connector arm 3360 may have uniform or non-uniform height along longitudinal axis 3302, for example as discussed above in reference to FIGS. 33A-C.

Figure 34A:
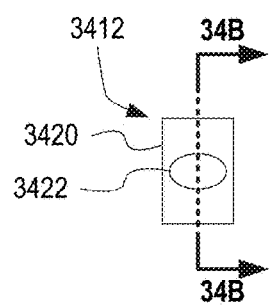
FIGS. 34A-D illustrate a connector arm and an extension cooperatively configured to restrict rotation of the extension, when held by the connector arm, according to an embodiment.
Figure 34B:
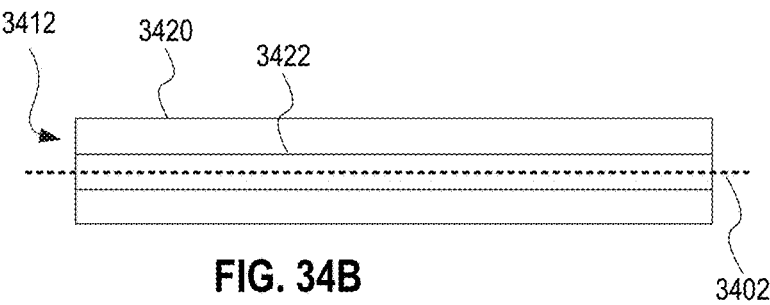
Figure 34C:
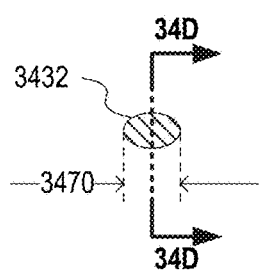
Figure 34D:
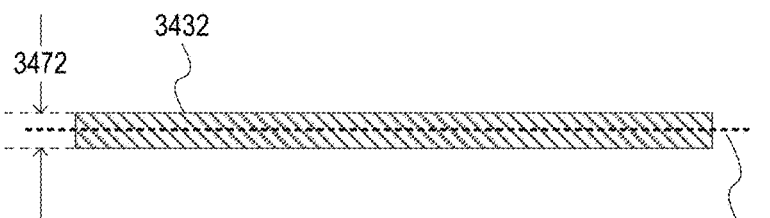

FIGS. 34A-D illustrate one exemplary connector arm 3420 and one exemplary extension 3432 cooperatively configured to restrict rotation of extension 3432, when held by connector arm 3420, about the longitudinal axis 3402 of extension 3432. FIG. 34A is a posterior end view of a distal end 3412 of connector arm 3420, equivalent to the view used in FIG. 33A. FIG. 34B is a cross-sectional side view of connector arm 3420, with the cross section taken along line 34B-34B indicated in FIG. 34A. The view of FIG. 34B is equivalent to the view used in FIG. 33B. FIG. 34C is a posterior end view of extension 3432, equivalent to the view used in FIG. 34A. FIG. 34D is a cross-sectional side view of extension 3432, with the cross section taken along line 34D-34D indicated in FIG. 34C. The view of FIG. 34D is equivalent to the view used in FIG. 34B. FIGS. 34A-D are best viewed together.

Connector arm 3420 is an embodiment of connector arm 3220, and extension 3432 is an embodiment of extension 3232. Connector arm 3420 is similar to connector arm 3320 except for forming a receptacle 3422 that is not symmetric under rotation about longitudinal axis 3402 of connector arm 3420. Without departing from the scope hereof, connector arm 3420 may be modified in a manner similar to that discussed above in reference to FIGS. 33C and 33D.

Extension 3432 is also not symmetric under rotation about its longitudinal axis 3482. Longitudinal axis 3482 of extension 3432 is substantially parallel to longitudinal axis 3402 of connector arm 3420 when extension 3432 is seated in receptacle 3422. The cross section of extension 3432 (FIG. 34C) has width 3470 in one dimension, and height 3472 in the orthogonal dimension. Height 3472 is greater than width 3470. The cross section of receptacle 3422 (FIG. 34A) may substantially match the cross section of extension 3432, optionally with receptacle 3422 being slightly larger than extension 3432 to allow for manufacturing tolerances and/or ease of insertion of extension 3432 into receptacle 3422. The lack of rotational symmetry of extension 3432 and receptacle 3422 prohibits, or at least restricts, rotation of extension 3432 about longitudinal axis 3402.

Without departing from the scope hereof, a portion of extension 3432 may have a smaller cross section than that shown in FIG. 34C. For example, one or more segments of extension 3432 along longitudinal axis 3482 may be characterized by a smaller cross section than that shown in FIG. 34C.

It is understood that connector arm 3420 and extension 3432 are only examples of a more general embodiments of connector arm 3220 and extension 3232, wherein connector arm 3220 and extension 3232 cooperate to restrict or prohibit rotation of extension 3232 about the longitudinal axis of connector arm 3220.

Figure 35A:
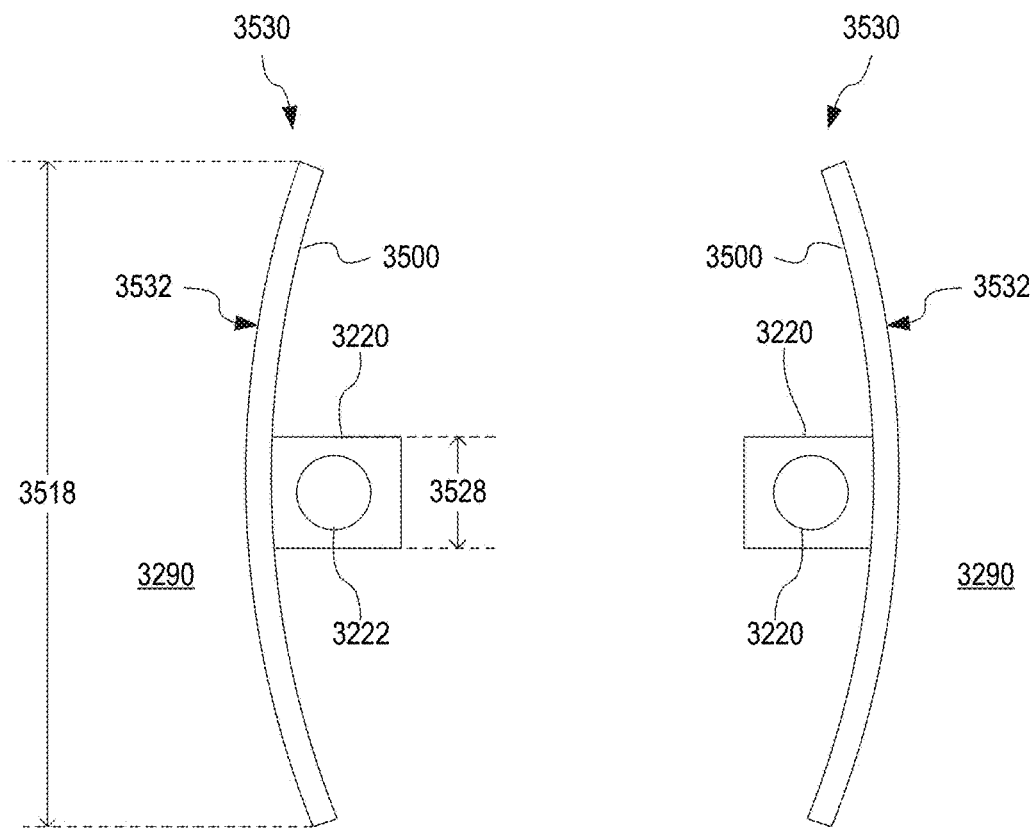
FIG. 35A illustrates a pair of retractor blades configured for mounting on connector arms, according to an embodiment.

FIG. 35A illustrates one exemplary pair of retractor blades 3500 configured for mounting on connector arms 3220 (or, alternatively, connector arms 2922). Each retractor blade 3500 has a surface 3532. When retractor blades 3500 are mounted on connector arms 3220, surfaces 3532 face laterally outward and serve to retract soft tissue 3290 anterior to cervical spine segment 180. Each retractor blade 3500 has height 3518. Height 3518 is sufficient to retract soft tissue 3290. In one embodiment, height 3518 is at least 5 millimeters, for example between one and five centimeters. The corresponding height 3528 of connector arm 3220 may be less than 3518.

Retractor blades 3500 may be made of metal or a polymer, such as plastic. In certain embodiments, for example when made of a polymer, retractor blades 3500 are disposable. Retractor blades 3500 may be removably coupled to connector arms 3220, such that one pair of retractor blades 3500 may, after use, be replaced by another pair of retractor blades 3500. System 3200 may be provided with retractor blades 3500 either pre-mounted on connector arms 3220 or detached from connector arms 3220.

Without departing from the scope hereof, the shape of retractor blades 3500 may be different from that shown in FIG. 35A. For example, retractor blades 3500 may be substantially planar instead of curved (as shown in FIG. 35A) and/or retractor blades 3500 may have teeth for grabbing soft tissue 3290.

Figure 35B:
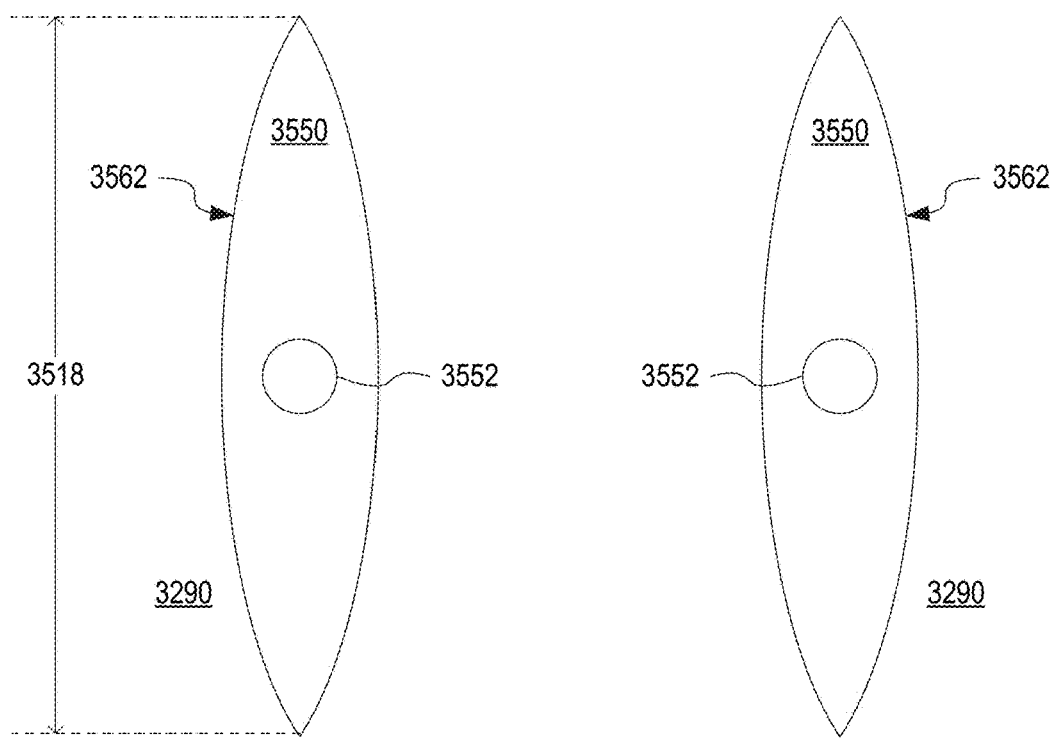
FIG. 35B illustrates a pair of connector arms forming retractor blades, according to an embodiment.

FIG. 35B illustrates a pair of exemplary connector arms 3550 forming retractor blades. Connector arms 3550 are an embodiment of connector arms 3220, which incorporates retractor blades. Each connector arm 3550 forms a receptacle 3552 configured to hold extension 3232. Receptacle 3552 is an embodiment of receptacle 3222. Each connector arm 3550 has a surface 3562. When connector arms 3550 are implemented in system 3200, surfaces 3562 face laterally outward and serve to retract soft tissue 3290 anterior to cervical spine segment 180. Each connector arm 3550 has height 3518.

Connector arms 3550 may be made of metal or a polymer, such as plastic. In certain embodiments, for example when made of a polymer, connector arms 3550 are disposable. Each connector arm 3550 may be an integrally formed piece or, alternatively, be assembled from a plurality of pieces.

Without departing from the scope hereof, the shape of connector arms 3550 may be different from that shown in FIG. 35B. For example, connector arms 3550 may be substantially planar instead of curved (as shown in FIG. 35B) and/or connector arms 3550 may have teeth for grabbing soft tissue 3290.

Although shown in FIG. 35B as having circular cross section, receptacle 3552 have a different shape, without departing from the scope hereof. For example, the shape of receptacle 3552 may be non-circular, as discussed above in reference to FIGS. 34A-D for receptacle 3422. Also without departing from the scope hereof, receptacle may be an open groove, for example similar to groove 3362 discussed above in reference to FIG. 33D.

FIGS. 36A-F show exemplary tips for insertion into uncinate joints 120 from intervertebral disc space 140. Each of the tips of FIGS. 36A-F forms an embodiment of tip 3230 and may be used as a distractor tip, a trial implant, and/or an uncinate joint stabilizer.

Figure 36A:
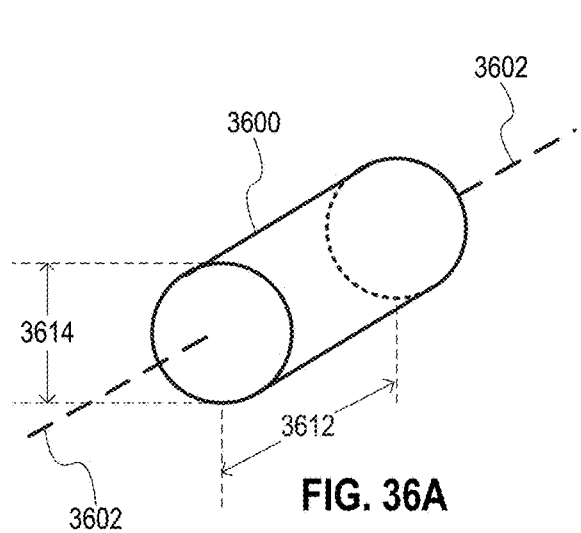
FIGS. 36A-F illustrate exemplary tips that may be distractor tips, trial implants, and/or uncinate joint stabilizers.
Figure 36B:
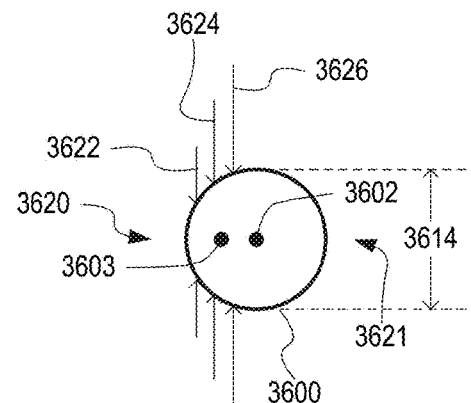

FIGS. 36A and 36B illustrate one exemplary cylindrical tip 3600. FIG. 36A is a perspective view of cylindrical tip 3600. FIG. 36B is an end view of cylindrical tip 3600, taken along cylinder axis 3602 of cylindrical tip 3600. FIGS. 36A and 36B are best viewed together.

Cylindrical tip 3600 has length 3612, along cylinder axis 3602, and diameter 3614. Diameter 3614 is, for example, in the range between two and seven millimeters, to enable cylindrical tip 3600 to distract and/or stabilize uncinate joint 120. Length 3612 is, for example, at least three millimeters. In embodiments of cylindrical tip 3600 configured to function as uncinate joint stabilizers (final implants), length 3612 may be at least six millimeters to ensure sufficient contact areas between (a) cylindrical tip 3600 and (b) superior surface 684 and inferior surface 686 of uncinate joint 120.

Upon insertion of cylindrical tip 3600 into uncinate joint 120, a lateral side 3620 of cylindrical tip 3600 is first to enter uncinate joint 120. (Since cylindrical tip 3600 is symmetric under rotation about cylinder axis 3602, lateral side 3620 may be any side of cylindrical tip 3600 in FIG. 36B.) The height of cylindrical tip 3600 gradually increases from lateral side 3620 in the direction toward an opposite facing medial side 3621 of cylindrical tip 3600. This gradual height increase is illustrated in FIG. 36B with the height of cylindrical tip 3600 increasing from zero at the extreme point of lateral side 3620, through heights 3622, 3624, and 3626 until reaching the maximum height characterized by diameter 3614. This gradual height increase eases insertion of cylindrical tip 3600 into uncinate joint 120. The gradual height increase may also contribute to increased distraction of uncinate joint 120 when cylindrical tip 3600 is pushed further into uncinate joint 120.

Although not shown in FIGS. 36A and 36B, the diameter 3614 of cylindrical tip 3600 may, without departing from the scope hereof, decrease along the length of cylinder axis 3902, for example to approximately match lordosis of cervical spine segment 180.

Referring now to FIGS. 25-28, each of tapered elements 2500, 2600, and 2700, also exhibit a gradual increase in height in the direction from a lateral side (the thinner end of the tapered element) of the tapered element in direction toward a medial side of the tapered element.

Referring again to FIGS. 36A and 36B, a pair of cylindrical tips 3600 may be inserted into uncinate joint 120 using (a) actuator 2900, (b) actuator 2900 with extensions 3020, (c) actuator 3100, or (d) actuator 3210 and extensions 3232.

In one exemplary scenario, rotation of the cylindrical tips 3600 cooperates with increase of distance 3250, by actuator 3210, to insert cylindrical tips 3600 into uncinate joints 120 with improved control. In this scenario a pair of cylindrical tips 3600 are attached to respective extensions 3232 and pushed into uncinate joints 120 using actuator 3210, as discussed above in reference to FIGS. 32A and 32B. This scenario employs embodiments of actuator 3210 and extensions 3232 that allow the surgeon to rotate of each extension 3232 about its longitudinal axis (parallel to direction 3204 in FIG. 32A). Each cylindrical tip 3600 is mounted on respective extension 3232 with the rotation axis of extension 3232 offset from cylinder axis 3602. FIG. 36B shows an exemplary offset between cylinder axis 3602 of cylindrical tip 3600 and a rotation axis 3603 of extension 3232. Due to this offset, rotation of extension 3232 will shift the position of cylindrical tip 3600 laterally, and in some instances also axially. Thus, the surgeon may first use actuator 3210 to position cylindrical tips 3600 to be engages with uncinate joints 120, and then rotate extensions 3232 to push cylindrical tips 3600 further into uncinate joints 120 and thereby further distract uncinate joints 120. In one embodiment, the rotation of extensions 3232 provides finer control of the degree of distraction of uncinate joint 120 than what may be achieved by increasing distance using actuator 3210.

It is understood that, in other scenarios, cylindrical tip 3600 may be coupled to extension 3232 such that cylinder axis 3602 coincides with rotation axis 3603 of extension 3232.

In one embodiment, at least a portion of the surfaces of cylindrical tip 3600 perpendicular to cylinder axis 3602 is rough, to help temporarily or permanently secure cylindrical tip 3600 in uncinate joint 120. This embodiment of cylindrical tip 3600 may be used as a distractor tip and/or an uncinate joint stabilizer.

Figure 36C:
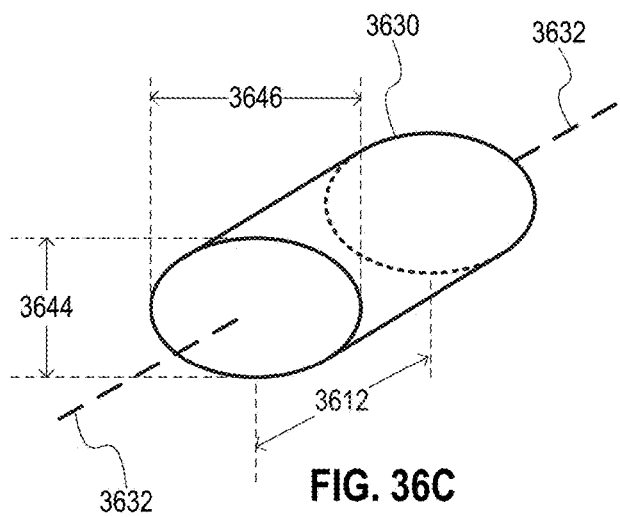
Figure 36D:
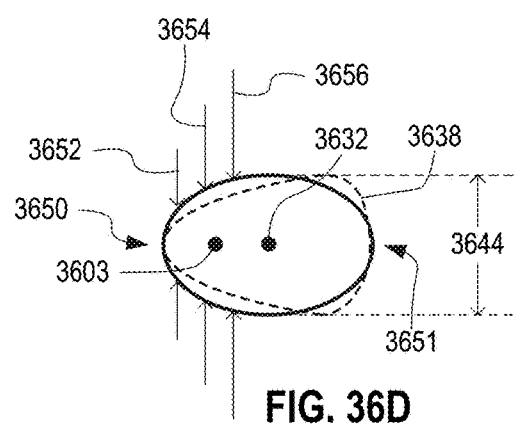

FIGS. 36C and 36D illustrate one exemplary elongated oval tip 3630. FIG. 36C is a perspective view of elongated oval tip 3630. FIG. 36D is an end view of elongated oval tip 3630, taken along a longitudinal axis 3632 of elongated oval tip 3630. FIGS. 36C and 36D are best viewed together. Elongated oval tip 3630 is similar to cylindrical tip 3600, except that the cross sectional shape of elongated oval tip 3630 (as shown in the end view provided in FIG. 36D) is oval rather than circular.

Elongated oval tip 3630 has length 3612, height 3644, and width 3646. Height 3644 is less than width 3646. Each of height 3644 and width 3646 are, for example, in the range between two and ten millimeters, with height 3644 being less than width 3646.

Upon insertion of elongated oval tip 3630 into uncinate joint 120, a lateral side 3650 of elongated oval tip 3630 is first to enter uncinate joint 120. Easiest insertion of elongated oval tip 3630 into uncinate joint 120 may be achieved when lateral side 3650 is at, or near the extreme of width 3646 of elongated oval tip 3630 (as shown in FIG. 36C). However, without departing from the scope hereof, lateral side 3650 may be another side of elongated oval tip 3630. The height of elongated oval tip 3630 gradually increases from lateral side 3650 in the direction toward an opposite facing medial side 3651 of elongated oval tip 3630. This gradual height increase is illustrated in FIG. 36C with the height of elongated oval tip 3630 increasing from zero at the extreme point of lateral side 3650, through heights 3652, 3654, and 3656 until reaching the maximum height characterized by height 3644. This gradual height increase eases insertion of elongated oval tip 3630 into uncinate joint 120. The gradual height increase may also contribute to increased distraction of uncinate joint 120 when elongated oval tip 3630 is pushed further into uncinate joint 120.

Although not shown in FIGS. 36C and 36D, one of both of height 3644 and width 3646 of elongated oval tip 3630 may, without departing from the scope hereof, decrease along the length of longitudinal axis 3632, for example to approximately match lordosis of cervical spine segment 180.

A pair of elongated oval tips 3630 may be inserted into uncinate joint 120 using (a) actuator 2900, (b) actuator 2900 with extensions 3020, (c) actuator 3100, or (d) actuator 3210 and extensions 3232.

In one exemplary scenario, rotation of the elongated oval tips 3630 cooperates with increase of distance 3250, by actuator 3210, to insert elongated oval tips 3630 into uncinate joints 120 with improved control. In this scenario a pair of elongated oval tips 3630 are attached to respective extensions 3232 and pushed into uncinate joints 120 using actuator 3210, as discussed above in reference to FIGS. 32A and 32B. This scenario employs embodiments of actuator 3210 and extensions 3232 that allow the surgeon to rotate of each extension 3232 about its longitudinal axis (parallel to direction 3204 in FIG. 32A). Each elongated oval tip 3630 is mounted on respective extension 3232 with the rotation axis 3603 of extension 3232 either coinciding with longitudinal axis 3632 or offset from longitudinal axis 3632 (as illustrated by example in FIG. 36D). Regardless of whether longitudinal axis 3632 of elongated oval tip 3630 coincides with or is offset from rotation axis 3603 of extension 3232, rotation of extension 3232 may be applied to move elongated oval tip 3630 further into uncinate joint 120 and/or further distract uncinate joint 120 in a manner similar to that discussed above in reference to FIGS. 36A and 36B.

In one embodiment, at least a portion of the surfaces of elongated oval tip 3630 perpendicular to longitudinal axis 3632 is rough, to help temporarily or permanently secure elongated oval tip 3630 in uncinate joint 120. This embodiment of cylindrical tip 3600 may be used as a distractor tip and/or an uncinate joint stabilizer.

In a modification, the cross section of elongated oval tip 3630 is asymmetric in the dimension associate with width 3646, for example as indicated by dashed outline 3638 in FIG. 36D. This modified embodiment of elongated oval tip 3630 may have cross section of a shape akin to that of an egg or a tear drop.

Figure 36E:
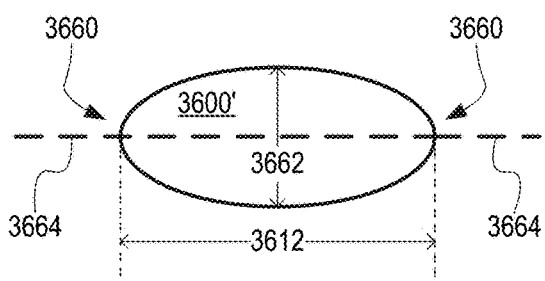

FIG. 36E illustrates one exemplary ellipsoidal tip 3600', in cross-sectional view with the cross section coinciding with a longitudinal axis 3664 of ellipsoidal tip 3600'. Ellipsoidal tip 3600' represents a modification of either one of cylindrical tip 3600 and elongated oval tip 3630, which is rounded also in the axial dimension (that is, in the dimension associated with longitudinal axis 3664). Ellipsoidal tip 3600' has length 3612. The size of ellipsoidal tip 3600' in dimensions orthogonal to longitudinal axis 3664 may, at the thickest part of ellipsoidal tip 3600' (indicated by arrow 3662), be similar to the corresponding dimensions of cylindrical tip 3600 (diameter 3614) or the corresponding dimensions of elongated oval tip 3630 (height 3644 and width 3646).

Without departing from the scope hereof, the shape of ellipsoidal tip 3600' may deviate from being exactly ellipsoidal, as long as the axial ends 3660 of ellipsoidal tip 3600' are rounded.

Figure 36F:
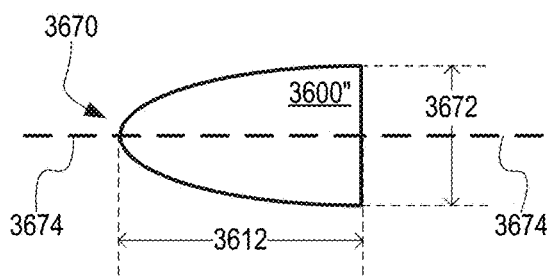

FIG. 36F illustrates one exemplary truncated ellipsoidal tip 3600'', in cross-sectional view with the cross section coinciding with a longitudinal axis 3674 of truncated ellipsoidal tip 3600''. Truncated ellipsoidal tip 3600'' represents a modification of either one of cylindrical tip 3600 and elongated oval tip 3630, which is rounded at a leading end 3670 in the axial dimension (that is, in the dimension associated with longitudinal axis 3674). Truncated ellipsoidal tip 3600'' is configured for insertion into intervertebral disc space 140 with leading end 3670 first. Truncated ellipsoidal tip 3600'' has length 3612. The size of truncated ellipsoidal tip 3600'' in dimensions orthogonal to longitudinal axis 3674 may, at the thickest part of truncated ellipsoidal tip 3600'' (as indicated by arrow 3672), be similar to the corresponding dimensions of cylindrical tip 3600 (diameter 3614) or the corresponding dimensions of elongated oval tip 3630 (height 3644 and width 3646).

Without departing from the scope hereof, the shape of ellipsoidal tip 3600' may deviate from being exactly that of a truncated ellipsoid, as long as the leading end 3670 of truncated ellipsoidal tip 3600'' is rounded.

Figure 37A:
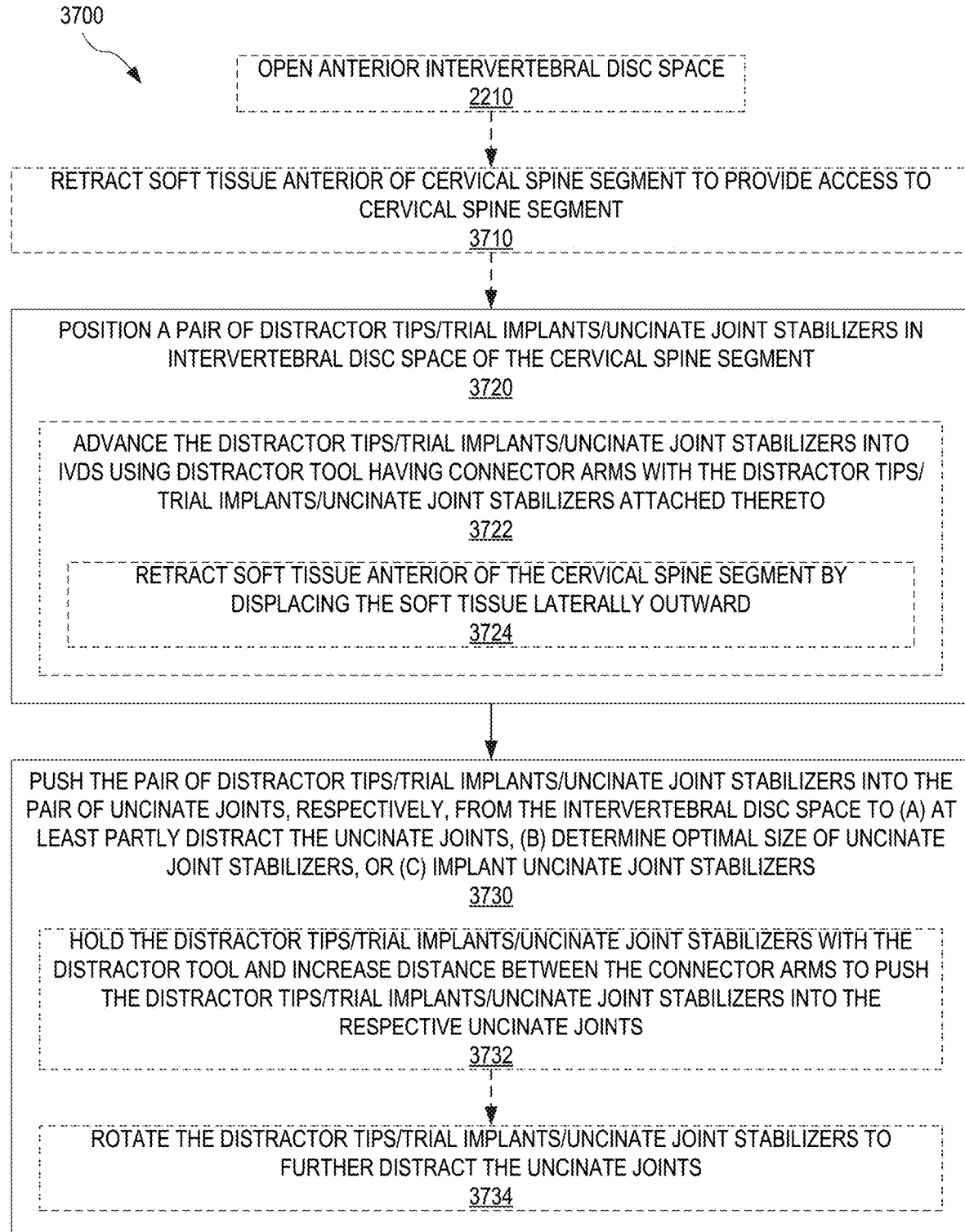
FIG. 37A illustrates a method for distracting uncinate joints, according to an embodiment.

FIG. 37A illustrates one exemplary method 3700 for distracting uncinate joints 120. Method 3700 may utilize system 3200, actuator 3100, actuator 2900, or actuator 2900 with extensions 3020. Method 3700 may be adapted to insert trial implants or uncinate joint stabilizers into uncinate joints 120, instead of or in combination with distracting uncinate joints 120.

Method 3700 includes steps 3720 and 3730. Step 3720 positions a pair of distractor tips, trial implants, or uncinate joint stabilizers in intervertebral disc space 140. In one example of step 3720, tapered elements 2800 or tips 3230 are positioned in intervertebral disc space 140. Step 3730 pushes the pair of distractor tips, trial implants, or uncinate joint stabilizers into uncinate joints 120, respectively, from intervertebral disc space 140. In one example of step 3730, tapered elements 2800 or tips 3230 are pushed from intervertebral disc space 140 into uncinate joints 120 along medial-to-lateral directions.

When performed with distractor tips, step 3730 at least partly distract uncinate joints 120. When performed with trial implants, step 3730 may serve to determine the optimal size of a pair of uncinate joint stabilizers to be implanted in uncinate joints 120 in a subsequent step. In step 3730, the trial implants may function as both distractor tips and trial implants, in which case the trial implants also at least partly distract uncinate joints 120. When performed with uncinate joint stabilizers, step 3730 implants the uncinate joint stabilizers in uncinate joints 120. In step 3730, these uncinate joint stabilizers may also function as distractor tips and distract uncinate joints 120 when being inserted into uncinate joints 120 from intervertebral disc space 140.

In an embodiment, method 3700 utilizes a distractor tool, such as actuator 2900 (optionally with extensions 3020), actuator 3100, or system 3200. In this embodiment, step 3720 includes a step 3722, and step 3730 includes a step 3732. Step 3722 advances the distractor tips/trial implants/uncinate joint stabilizers into intervertebral disc space 140 using a distractor tool having connector arms with the distractor tips/trial implants/uncinate joint stabilizers attached thereto. Step 3732 holds the distractor tips/trial implants/uncinate joint stabilizers with the distractor tool and increases the distance between the connector arms to push the distractor tips/trial implants/uncinate joint stabilizers into respective uncinate joints 120. In one example of step 3722, tips 3230 or tapered elements 2800 are connected to connector arms 3220 (via extensions 3232) or 2922 (optionally via extensions 3020) and advanced into intervertebral disc space 140 using actuator 3210 or actuator 2900/3100. In a related example of step 3732, a surgeon manipulates actuator 3210 or 2900/3100 to push tips 3230 or tapered elements 2800 into uncinate joints 120 along substantially medial-to-lateral directions.

In one implementation, the distractor tool allows the surgeon to rotate the distractor tips/trial implants/uncinate joint stabilizers. In this implementation, step 3730 may further include a step 3734 of rotating the distractor tips/trial implants/uncinate joint stabilizers to further distract uncinate joints 120. One example of step 3734 utilizes system 3200 configured to allow rotation of extensions 3232. In this example, the surgeon rotates each of the two extensions 3232 coupled with a respective pair of tips (e.g., embodiments of tips 3600 or tips 3630), to further distract uncinate joints 120 as discussed above in reference to FIGS. 36A-D. The surgeon may rotate both tips at the same time, or first rotate one tip and then rotate the other tip.

Figure 37B:
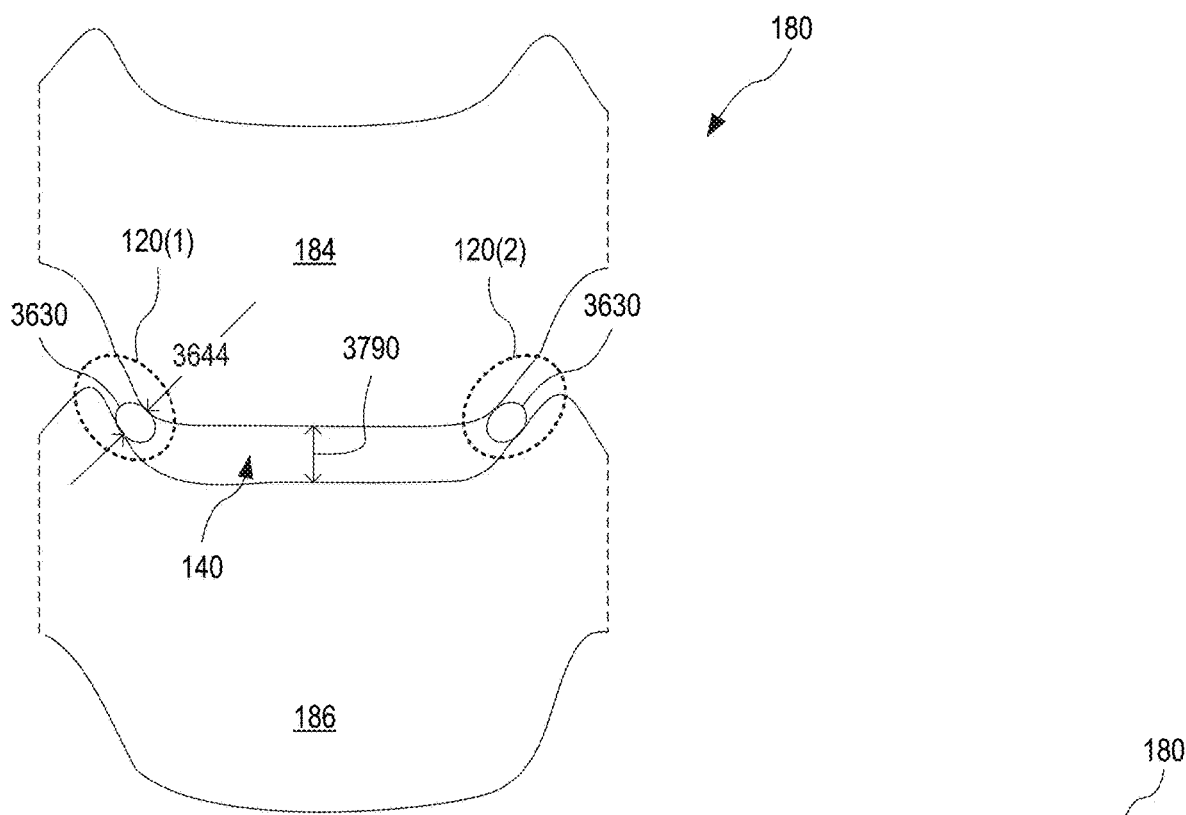
FIGS. 37B and 37C illustrate additional distraction of the uncinate joints achieved by rotation of distractor tips, according to an embodiment.
Figure 37C:
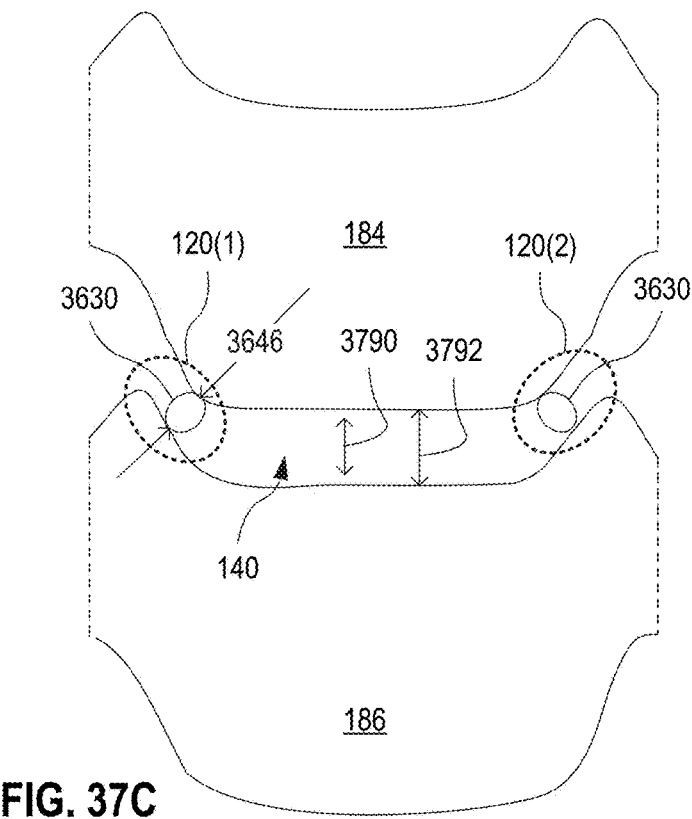

FIGS. 37B and 37C illustrate one example of step 3734 based upon rotation of a pair of elongated oval tips 3630 in respective uncinate joints 120. In this example, an elongated oval tip 3630 is inserted into each uncinate joint 120 with height 3644 defining or matching the spacing between the superior and inferior surfaces of each uncinate joints 120 (see FIG. 37B). Next, each elongated oval tip 3630 is rotated to have width 3646 span between the superior and inferior surfaces of each uncinate joints 120 (see FIG. 37C). Since width 3646 is greater than height 3644, this rotation results in further distraction of uncinate joints 120. In FIGS. 37B and 37C, this is easily recognized the increase of the height of intervertebral disc space 140 from height 3790 in FIG. 37B to height 3792 in FIG. 37C. For ease of comparison, height 3790 is inserted in FIG. 37C next to height 3792.

In an embodiment, method 3700 integrates retraction of soft tissue 3290 with at least one of distraction of uncinate joints 120 and insertion of trial implants or uncinate joint stabilizers into uncinate joints 120. In this embodiment, step 3722 further includes a step 3724 of retracting soft tissue 3290 anterior of cervical spine segment 180 by displacing the soft tissue laterally outward with connector arms of the distraction tool or with retractor blades attached to connector arms of the distraction tool. In one example of step 3724, connector arms 2922 or 3230, or extensions 3020, have width sufficient to retract soft tissue 3290, as discussed above in reference to FIGS. 29-35B. In another example of step 3724, the connector arms of the distractor tool have retractor blades 3500 mounted thereon. In this embodiment of method 3700, step 3732 may include maintaining the retraction of soft tissue 3290, and optionally further retracting soft tissue 3290. This embodiment of method 3700 may further include a step 3710 performed prior to step 3720. Step 3710 retracts soft tissue 3290 anterior of cervical spine segment 180 by laterally displacing soft tissue 3290 with the connector arms (e.g., connector arms 2922 or 3220, or extensions 3020) of the distractor tool or retractor blades (e.g., retractor blades 3500) attached thereto, to provide access to cervical spine segment 180.

In certain embodiments, method 3700 further includes step 2210 of opening at least an anterior portion of intervertebral disc space 140 prior to performing step 3710 or prior to performing step 3720. In one example of step 2210, as implemented in method 3700, the surgeon performs a partial discectomy to remove an anterior portion of intervertebral disc 150 from intervertebral disc space 140.

Figure 38:
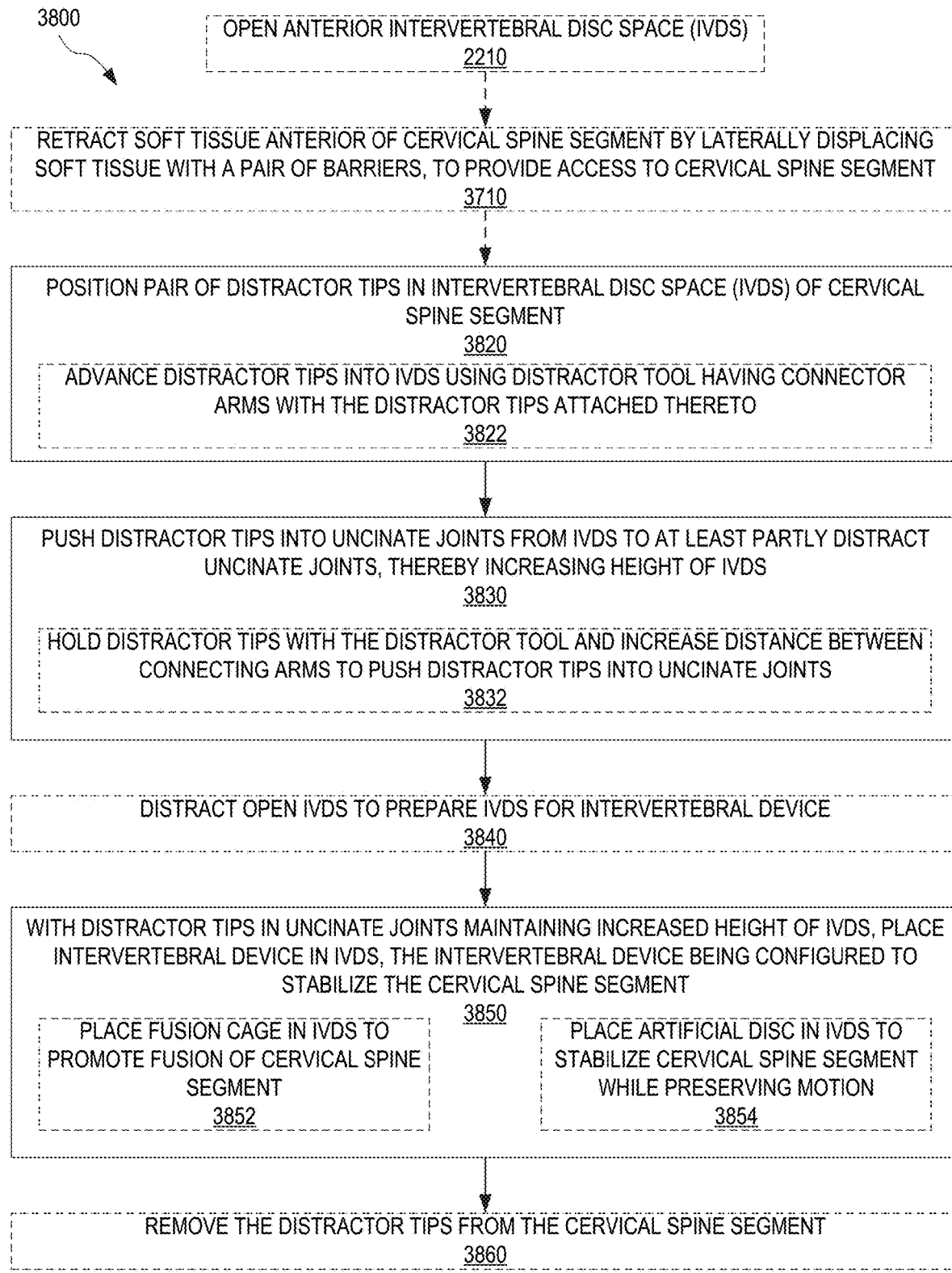
FIG. 38 illustrates a method for stabilizing a cervical spine segment utilizing uncinate joint distraction, according to an embodiment.

FIG. 38 illustrates one exemplary method 3800 for stabilizing cervical spine segment 180 utilizing uncinate joint distraction. Method 3800 is an alternative to conventional methods for stabilization of a cervical spine segment, wherein, e.g., a fusion cage or an artificial disc is implanted in the intervertebral disc space. In the conventional methods, prior to implanting the fusion cage or artificial disc, the height of the intervertebral disc space is increased by threading a distractor pin into each of the superior and inferior vertebrae and using these distractor pins to force apart superior and inferior vertebrae. Method 3800 eliminates the need for threading distractor pins into the superior and inferior vertebrae and instead uses distraction of the uncinate joints to increase the height of the intervertebral disc space. Method 3800 is an embodiment of method 3700.

Method 3800 includes steps 3820, 3830, and 3850. Step 3820 positions a pair of distractor tips in intervertebral disc space 140. In one example, step 3820 positions a pair of tapered elements 2800 or a pair of distractor tips 3230 in intervertebral disc space 140. Step 3830 pushes the distractor tips into uncinate joints 120 from intervertebral disc space 140 to at least partly distract uncinate joints 120, thereby increasing height of intervertebral disc space 140. In one example, step 3820 positions a pair of tapered elements 2800 or a pair of tips 3230 in intervertebral disc space 140, and step 3830 pushes the pair of tapered elements 2800 or tips 3230 from intervertebral disc space 140 into uncinate joints 120 along respective medial-to-lateral directions to increases the distance between the inferior and superior surfaces of each uncinate joint 120. This pushes apart superior vertebra 184 and inferior vertebra 186 and results in an increase of the height of intervertebral disc space 140. Step 3850 is performed with the distractor tips in place in uncinate joints 120 to maintain the increased height of intervertebral disc space 140. Step 3850 places an intervertebral device in intervertebral disc space 140. The intervertebral device is configured to stabilize cervical spine segment 180.

In one embodiment, step 3850 includes a step 3852 of placing a fusion cage in intervertebral disc space 140 to promote fusion of cervical spine segment 180. In another embodiment, step 3850 includes a step 3854 of placing an artificial disc in intervertebral disc space 140 to stabilize cervical spine segment 180 while preserving motion of cervical spine segment 180. Step 3850 may utilize a fusion cage or artificial disc known in the art.

In certain embodiments, method 3800 integrates retraction of soft tissue 3290 with distraction of uncinate joints 120, and achieves soft-tissue retraction and uncinate-joint distraction with a single integrated retractor-distractor tool. As discussed above in reference to FIGS. 29-35B, each of actuator 2900 (optionally with extensions 3020), actuator 3100, and actuator 3210 may be configured to function as an integrated retractor-distractor tool. In this embodiment, method 3800 may further include step 3710, step 3820 may further include a step 3822, and step 3830 may further include a step 3832. In method 3800, step 3710 (when included) is performed prior to step 3820. Step 3710 is performed as discussed above in reference to FIG. 37. Steps 3822 and 3832 are examples of steps 3722 and 3732, respectively, performed using distractor tips. Although not shown in FIG. 38, step 3830 may also include step 3734 using distractor tips. Embodiments of method 3800 performed using an integrated retractor-distractor tool achieve soft-tissue retraction and height increase of intervertebral disc space 140 with a single tool, wherein both the soft-tissue retraction and the height increase are achieved by moving retractors and distractors laterally outward. In contrast, conventional methods use one tool to laterally retract soft tissue and another, separate tool to axially distract the superior and inferior vertebra. These two separate tools operate in perpendicular directions and crowd the space above cervical spine segment 180. In comparison, method 3800 reduces the amount of equipment required and improves both (a) the surgeon's access to cervical spine segment 180 and (b) pathways for imaging of cervical spine segment 180 during the procedure.

Method 3800 may further include one, two, or all of steps 2210, 3840, and 3860. Step 2210 is performed prior to step 3710 or prior to step 3820. Step 3840 is performed between steps 3830 and 3850. Step 3840 distracts open intervertebral disc space 140 to prepare intervertebral disc space 140 for the intervertebral device of step 3850. In one example of step 3840, the surgeon performs a discectomy of cervical spine segment 180, optionally while an integrated soft-tissue retractor and uncinate-joint-distractor tool, such as an embodiment of actuator 2900 (for example with extensions 3020) or an embodiment of actuator 3100 or 3210, maintains the surgeon's access to intervertebral disc space 140. Step 3860 is performed after step 3850. Step 3860 removes the distractor tips from cervical spine segment 180. In one example of step 3860, tapered elements 2800 or tips 3230 are pulled out of cervical spine segment 180 as actuator 2900, 3100, or 3210 is removed from patient 170.

In one embodiment, method 3800 utilizes self-securing distractor tips, such as any one of the distractor tips of FIGS. 36A-F having rough surfaces. In this embodiment, actuator 3210 may position the distractor tips in uncinate joints 120 through performing steps 3822 and 3832, and actuator 3210 may then be removed from patient 170 while the distractor tips remain in uncinate joints 120 during the execution of steps 3840 (optionally) and 3850. Also in this embodiment, actuator 3210 may be reconnected to the distractor tips, in step 3860, to remove the distractor tips from cervical spine segment 180 using actuator 3210.

Figure 39A:
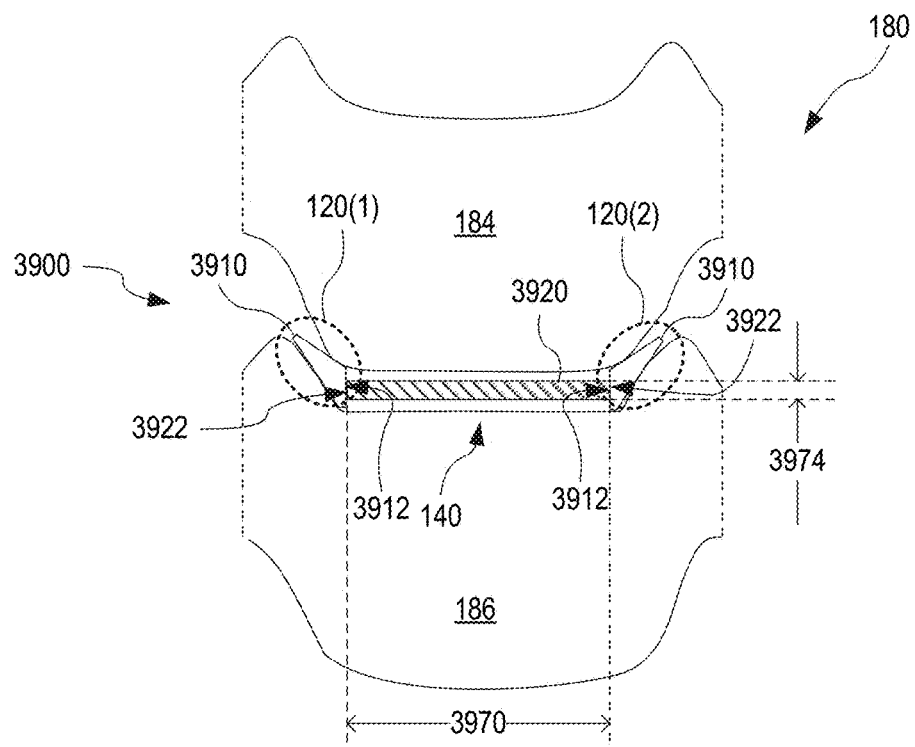
FIGS. 39A and 39B illustrate a system for stabilizing a cervical spine segment utilizing uncinate joint stabilization and further stabilization across the intervertebral disc space, according to an embodiment.
Figure 39B:
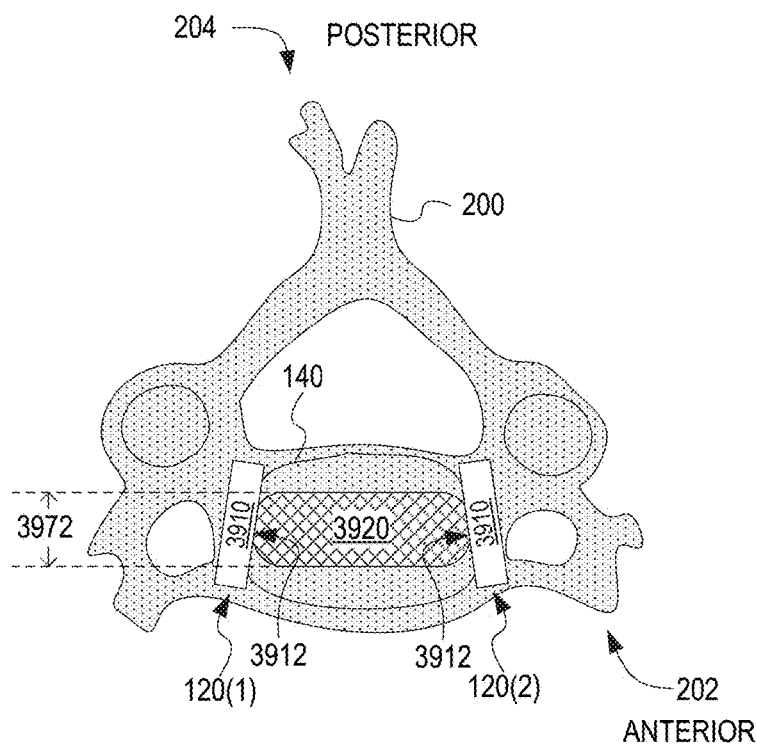

FIGS. 39A and 39B illustrate one exemplary system 3900 for stabilizing cervical spine segment 180 utilizing uncinate joint stabilization and further stabilization across intervertebral disc space 140. FIG. 39A shows system 3900 in anterior view, and FIG. 39B shows system 3900 in axial view. FIGS. 39A and 39B are best viewed together. System 3900 includes a stabilizing bridge 3920 that bridges across intervertebral disc space 140 to mechanically couple between a pair of uncinate joint stabilizers 3910, such as tapered elements 2800, positioned in respective uncinate joints 120 adjacent intervertebral disc space 140. System 3900 may further include uncinate joint stabilizers 3910. Stabilizing bridge 3920 applies laterally outward pressure on medial facing surfaces 3912 of uncinate joint stabilizers 3910. Without departing from the scope hereof, uncinate joint stabilizers 3910 may extend partly into intervertebral disc space 140.

In one embodiment, the width of stabilizing bridge 3920 is fixed. In another embodiment, stabilizing bridge 3920 is laterally extendable to achieve width required to mechanically couple between uncinate joint stabilizers 3910.

Stabilizing bridge 3920 has width 3970 or is laterally extendable to at least width 3970. Stabilizing bridge has depth 3972 and height 3974. Width 3970 is for example in the range between 15 and 25 millimeters. Depth 3972 may span the full depth of intervertebral disc space 140, or just a part of the depth of intervertebral disc space 140. Height 3974 is in the range between 3 and 11 millimeters, for example.

In one embodiment, height 3974 substantially spans the full height of intervertebral disc space 140. In this embodiment, stabilizing bridge 3920 may include or carry bone graft material to promote fusion in intervertebral disc space 140. Uncinate joint stabilizers 3910 may also include or carry bone graft material to promote fusion in uncinate joints 120. Thus, in this embodiment, system 3900 may be configured to promote fusion in both uncinate joints 120 and intervertebral disc space 140. In one implementation, stabilizing bridge 3920 has one or more voids capable of accommodating bone graft material to promote fusion in intervertebral disc space 140. Bone graft material may be loaded into the void(s) of stabilizing bridge 3920 before or after inserting stabilizing bridge 3920 into intervertebral disc space 140. This embodiment of stabilizing bridge 3920 is compatible with step 2252 of method 2200 and with step 2422 of method 2400. In another embodiment, at least a portion of stabilizing bridge 3920 is a porous portion substantially composed of bone graft material that promotes fusion in intervertebral disc space 140. This embodiment of stabilizing bridge 3920 is compatible with step 2252 of method 2200 and with step 2422 of method 2400.

In another embodiment, height 3974 of stabilizing bridge 3920 is less than the height of intervertebral disc space 140. In this embodiment, stabilizing bridge 3920 may serve to help secure uncinate joint stabilizers 3910 in uncinate joints 120 by virtue of the laterally outward pressure applied to medial facing surfaces 3912.

Generally, the mechanical coupling between stabilizing bridge 3920 and uncinate joint stabilizers 3910 may help secure one or both of stabilizing bridge 3920 and uncinate joint stabilizers 3910 in cervical spine segment 180. Without departing from the scope hereof, uncinate joint stabilizers 3910 may be partly or fully self-securing. For example, the uncinate joints stabilizers may include protruding features 2580, as discussed above in reference to FIGS. 25B, 26, and 27. One or both of (a) laterally outward facing surfaces 3912 of stabilizing bridge 3920 and (b) medial facing surfaces 3912 of uncinate joint stabilizers 3910 may be textured to reduce or eliminate any possibility of laterally outward facing surfaces 3912 sliding along medial facing surfaces 3912, for example to further secure stabilizing bridge 3920 to uncinate joint stabilizers 3910.

Although not shown in FIGS. 39A and 39B, stabilizing bridge 3920 may be lordotic, that is, tapered along an anterior-to-posterior direction, to at least approximately match lordosis of cervical spine segment 180, without departing from the scope hereof. Likewise, uncinate joint stabilizers 3910 may be lordotic.

Stabilizing bridge 3920 may be non-load bearing or partial-load bearing, as discussed in reference to FIG. 22.

Stabilizing bridge 3920 may be used in steps 2250 and 2260 of method 2200 (FIG. 22), and in steps 2420 and 2436 of method 2400 (FIG. 24). Referring now to FIGS. 22, 39A, and 39B in combination, method 2200 inserts uncinate joint stabilizers 3910 into uncinate joints 120 in step 2220. In step 2250 (optionally in cooperation with step 2260), method 2200 inserts stabilizing bridge 3920 into intervertebral disc space 140 to mechanically couple between uncinate joint stabilizers 3910.

Referring now to FIGS. 24, 39A, and 39B in combination, method 2400 inserts uncinate joint stabilizers 3910 into uncinate joints 120 in step 2410. In step 2420 (optionally in cooperation with step 2436), method 2400 inserts stabilizing bridge 3920 into intervertebral disc space 140 to mechanically couple between uncinate joint stabilizers 3910.

Figure 40A:
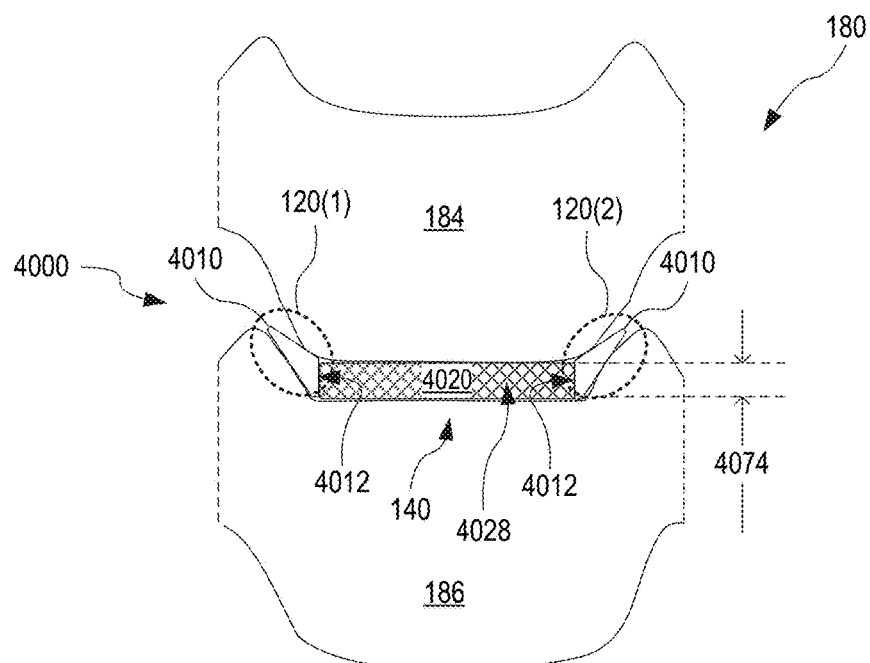
FIGS. 40A-D illustrate a system for stabilizing a cervical spine segment utilizing uncinate joint stabilization and a rigid stabilizing bridge spanning across the intervertebral disc space between uncinate joint stabilizers in the uncinate joints, according to an embodiment.

FIGS. 40A-D illustrate one exemplary system 4000 for stabilizing cervical spine segment 180 utilizing uncinate joint stabilization and a rigid stabilizing bridge 4020 spanning across intervertebral disc space 140 between uncinate joint stabilizers 4010 in uncinate joints 120. System 4000 is an embodiment of system 3900. Rigid stabilizing bridge 4020 is an embodiment of stabilizing bridge 3920. Uncinate joint stabilizers 4010 are embodiments of uncinate joint stabilizers 3910. System 4000 may be provided with both rigid stabilizing bridge 4020 and uncinate joint stabilizers 4010. Alternatively, rigid stabilizing bridge 4020 is provided alone, for use in cooperation with uncinate joint stabilizers provided by a third party, for example. FIG. 40A is an anterior view of system 4000 in cervical spine segment 180.

Figure 40B:
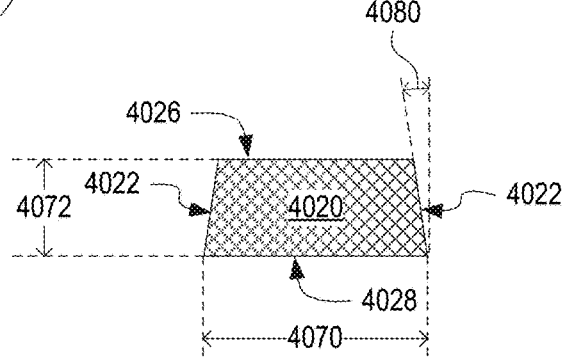
Figure 40C:
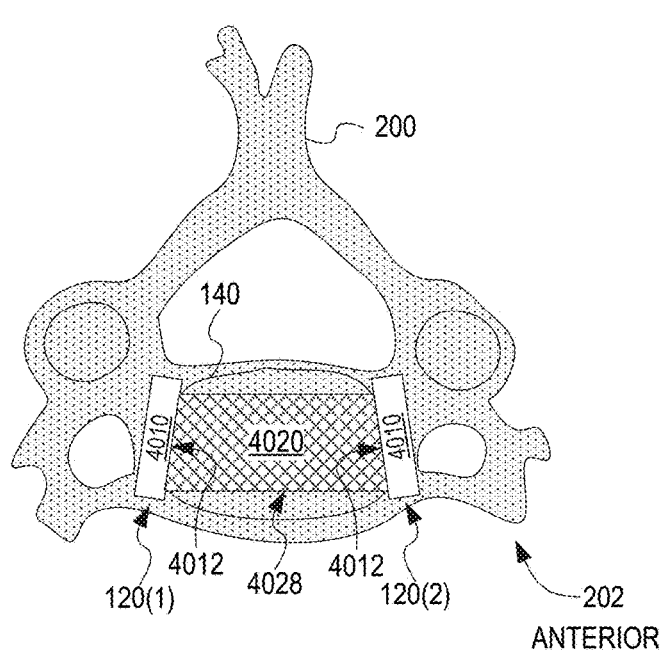
Figure 40D:
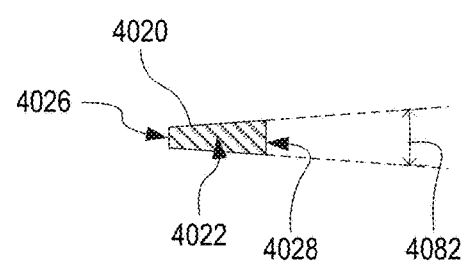

FIG. 40B is an axial view of rigid stabilizing bridge 4020. FIG. 40C is an axial view of system 4000 in cervical spine segment 180. FIG. 40D is a lateral view of rigid stabilizing bridge 4020. FIGS. 40A-D are best viewed together.

Rigid stabilizing bridge 4020 is wedge-shaped, as shown in FIGS. 40B and 40C. Rigid stabilizing bridge 4020 has lateral surfaces 4022. Each of lateral surfaces 4022 are angled inward by an angle 4080, such that posterior surface 4026 of rigid stabilizing bridge 4020 is narrower, in the lateral dimension, than anterior surface 4028 of rigid stabilizing bridge 4020. Angle 4080 is configured to at least approximately match the convergence angle of uncinate joint stabilizers 4010 when positioned in the mutually converging uncinate joints 120, so as to optimize mechanical coupling between lateral surfaces 4022 of rigid stabilizing bridge 4020 and medially-facing surfaces 4012 of uncinate joint stabilizers 4010.

Rigid stabilizing bridge 4020 has width 4070, depth 4072, and height 4074, which may be similar to width 3970, depth 3972, and height 3974 of stabilizing bridge 3920.

In one embodiment, height 4074 substantially spans the full height of intervertebral disc space 140. In this embodiment, rigid stabilizing bridge 4020 may include or carry bone graft material to promote fusion in intervertebral disc space 140, as discussed in further detail above for stabilizing bridge 3920. Uncinate joint stabilizers 4010 may also include or carry bone graft material to promote fusion in uncinate joints 120. Thus, in certain embodiments, system 4000 is configured to promote fusion in both uncinate joints 120 and intervertebral disc space 140. In another embodiment, height 4074 of rigid stabilizing bridge 4020 is less than the height of intervertebral disc space 140. In this embodiment, rigid stabilizing bridge 4020 may serve to help secure uncinate joint stabilizers 4010 in uncinate joints 120 by virtue of the laterally outward pressure applied to medial facing surfaces 4012.

Optionally, rigid stabilizing bridge 4020 is lordotic (as shown in FIG. 40D) with a posterior-to-anterior taper angle 4082. Angle 4082 may be configured to at least approximately match lordosis of cervical spine segment 180.

Rigid stabilizing bridge 4020 may be used in steps 2250 and 2260 of method 2200 (FIG. 22), and in steps 2420 and 2436 of method 2400 (FIG. 24). Referring now to FIGS. 22 and 40A-D in combination, method 2200 inserts uncinate joint stabilizers 4010 into uncinate joints 120 in step 2220. In step 2250, method 2200 inserts rigid stabilizing bridge 4020 into intervertebral disc space 140 and wedges rigid stabilizing bridge 4020 into place between uncinate joint stabilizers 4010.

Referring now to FIGS. 24 and 40A-D in combination, method 2400 inserts uncinate joint stabilizers 4010 into uncinate joints 120 in step 2410. In step 2420 (optionally in cooperation with step 2436), method 2400 inserts rigid stabilizing bridge 4020 into intervertebral disc space 140 and wedges rigid stabilizing bridge 4020 into place between uncinate joint stabilizers 4010.

Figure 41:
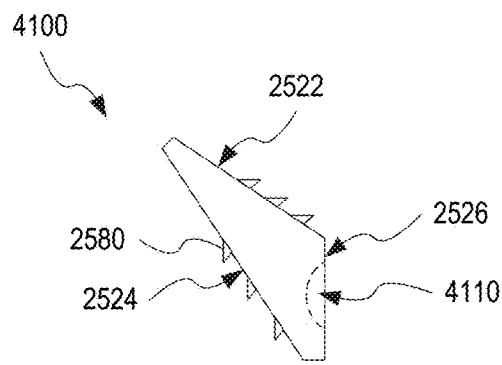
FIG. 41 illustrates a tapered implant for stabilizing an uncinate joint, according to an embodiment.

FIG. 41 illustrates one exemplary tapered implant 4100 for stabilizing uncinate joint 120 (FIG. 1). Tapered implant 4100 has an optional recess 4110 that facilitates mechanical coupling with an IVDS implant. Tapered implant 4100 is similar to tapered implant 2700 (FIG. 27), except for optionally including recess 4110. Without departing from the scope hereof, tapered implant 4100 may have the shape of tapered implant 2500 (FIG. 25) or tapered implant 2600 (FIG. 26), optionally modified to include recess 4110.

Figure 42:
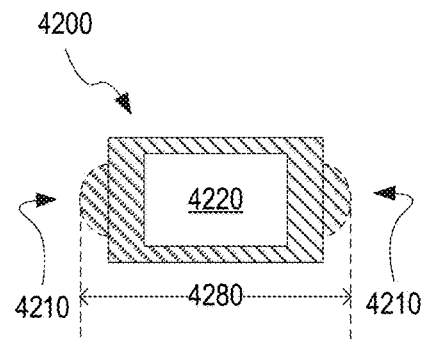
FIG. 42 illustrates an intervertebral-disc-space implant configured for placement in the intervertebral disc space of a cervical spine segment to at least participate in securing a pair of tapered implants in the uncinate joints of the cervical spine segment, according to an embodiment.

FIG. 42 illustrates one exemplary IVDS implant 4200 configured for placement in intervertebral disc space 140 (FIG. 1) to at least participate in securing tapered implants 4100 in uncinate joints 120. IVDS implant 4200 may include protruding features 4210 at opposing sides thereof. IVDS implant 4200 may be used in steps 2250 and 2260 of method 2200 (FIG. 22), and in steps 2420 and 2436 of method 2400 (FIG. 24). IVDS implant 4200 may be non-load bearing or partial-load bearing, as discussed in reference to FIG. 22. IVDS implant 4200 is an embodiment of stabilizing bridge 3920.

IVDS implant 4200 includes a mechanism 4220 for extending distance 4280 between features 4210. Thus, IVDS implant 4200 may couple with two tapered implants 4100. Optionally, each feature 4210 is shaped to preferably couple with tapered implant 4100 in recess 4110 of tapered implant 4100 (FIG. 41).

In one embodiment, IVDS implant 4200 has at least one void capable of accommodating bone graft material to promote fusion in intervertebral disc space 140. Bone graft material may be loaded into the void(s) of IVDS implant 4200 before or after inserting IVDS implant 4200 into intervertebral disc space 140. This embodiment of IVDS implant 4200 is compatible with step 2252 of method 2200 and with step 2422 of method 2400. In another embodiment, at least a portion of IVDS implant 4200 is a porous portion substantially composed of bone graft material that promotes fusion in intervertebral disc space 140. This embodiment of IVDS implant 4200 is compatible with step 2252 of method 2200 and with step 2422 of method 2400.

Figure 43:
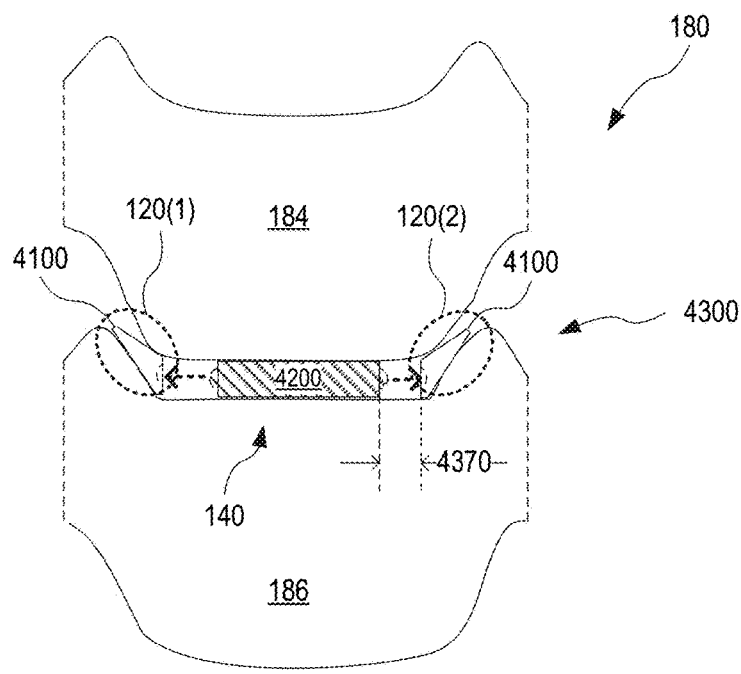
FIG. 43 illustrates use of the intervertebral-disc-space implant of FIG. 42 in the method of FIG. 22 or in the method of FIG. 24, according to an embodiment.

FIG. 43 illustrates exemplary use of IVDS implant 4200 (FIG. 42) in step 2260 of method 2200 (FIG. 22) or in step 2436 of method 2400 (FIG. 24). FIG. 43 shows, in an anterior view, IVDS implant 4200 located in intervertebral disc space 140 of cervical spine segment 180 (FIG. 1). A pair of tapered implants 4100 (FIG. 41) are located in uncinate joints 120 of cervical spine segment 180.

Referring now to FIGS. 22 and 41-43 in combination, method 2200 inserts tapered implants 4100 into uncinate joints 120 in step 2220. In step 2250, method 2200 inserts IVDS implant 4200 into intervertebral disc space 140 (FIG. 1). In step 2260, a surgeon actuates mechanism 4220 to extend distance 4280 along medial-to-lateral directions 220 (FIG. 2) such that features 4210 apply pressure on tapered implants 4100. By virtue of this pressure, IVDS implant 4200 at least participates in securing tapered implants 4100 in uncinate joints 120.

Referring now to FIGS. 24 and 41-43 in combination, method 2400 inserts tapered implants 4100 into uncinate joints 120 in step 2410. In step 2420, method 2400 inserts IVDS implant 4200 into intervertebral disc space 140 (FIG. 1) In step 2436, a surgeon actuates mechanism 4220 to extend distance 4280 along medial-to-lateral directions 220 such that features 4210 apply pressure on tapered implants 4100. By virtue of this pressure, IVDS implant 4200 at least participates in securing tapered implants 4100 in uncinate joints 120.

Without departing from the scope hereof, features 4210 and recesses 4110 may be switched, such that tapered implants 4100 have features 4210 and IVDS implant 4200 optionally has recesses 4110.

Figure 44:
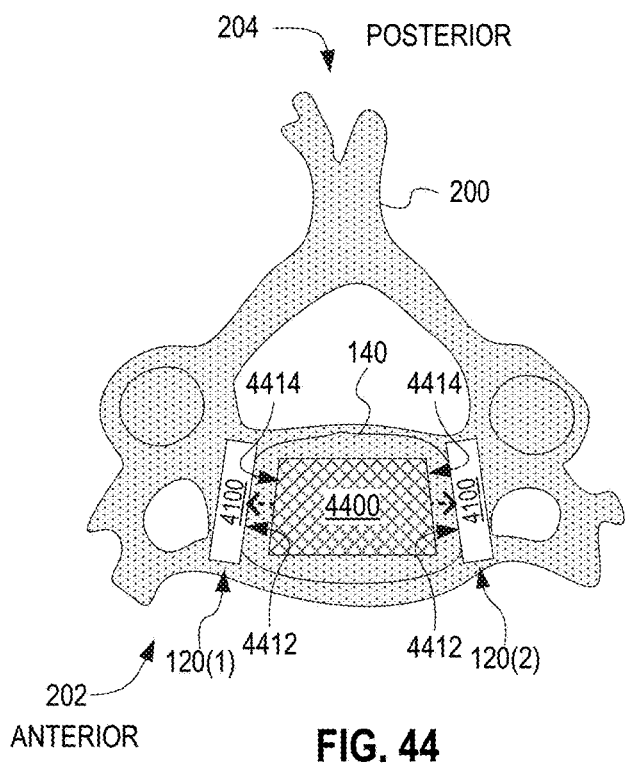
FIG. 44 illustrates a wedge-shaped intervertebral-disc-space implant that is laterally extendable to mechanically couple, across the intervertebral disc space, between tapered implants placed in the uncinate joints, according to an embodiment.

FIG. 44 illustrates one exemplary wedge-shaped IVDS implant 4400 that is laterally extendable to mechanically couple, across intervertebral disc space 140, between tapered implants 4100 placed in uncinate joints 120. IVDS implant 4400 is an embodiment of IVDS implant 4200. Tapered implants 4100 are mutually converging when placed in the mutually converging uncinate joints 120. Laterally outward facing surfaces 4414 of IVDS implant 4400 are non-parallel and approximately match the convergence angle of tapered implants 4100, such that IVDS implant 4400 may be in contact with a medial facing surface 4412 of each tapered implant 4100 over a finite extent in the anterior-to-posterior direction. The wedge angle of IVDS implant 4400 (i.e., the degree to which laterally outward facing surfaces 4414 deviate from being parallel to each other) may be fixed or adjustable.

Figure 45A:
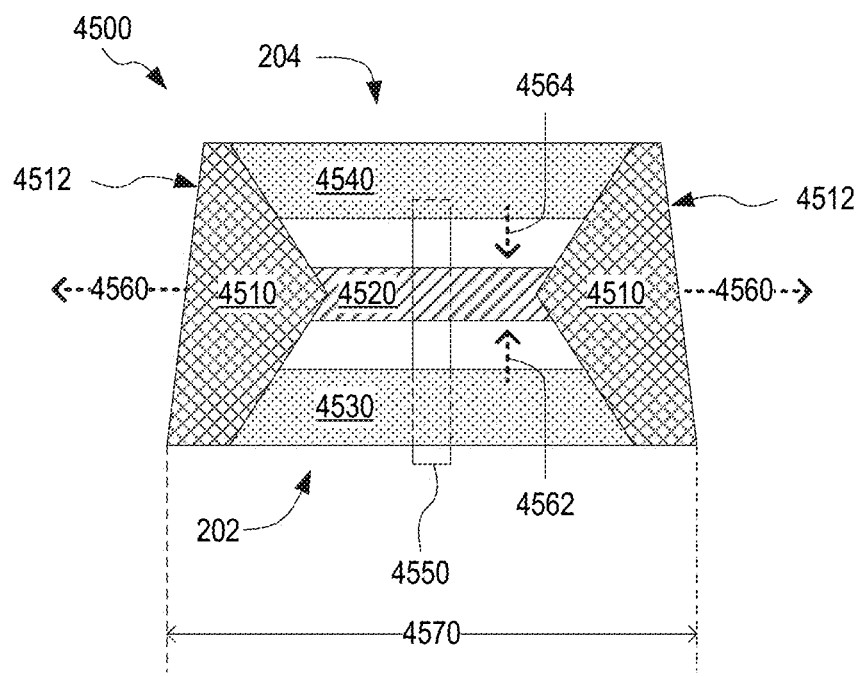
FIGS. 45A and 45B illustrate a laterally-extendable intervertebral-disc-space implant configured to mechanically couple, across the intervertebral disc space, between uncinate joint stabilizers positioned in the uncinate joints, according to an embodiment.
Figure 45B:
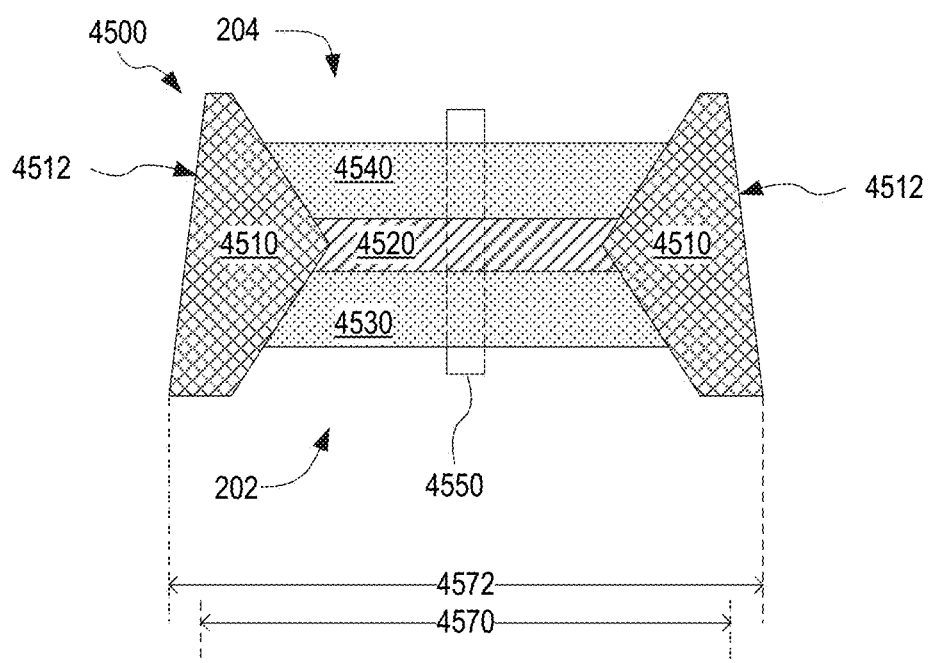

FIGS. 45A and 45B illustrate, in axial view, one exemplary laterally-extendable IVDS implant 4500 configured to mechanically couple, across intervertebral disc space 140, between uncinate joint stabilizers 3910 (FIGS. 39A and 39B) positioned in uncinate joints 120. IVDS implant 4500 is an embodiment of stabilizing bridge 3920. FIG. 45A shows IVDS implant 4500 prior to being laterally extended, and FIG. 45B shows IVDS implant 4500 when laterally extended. FIGS. 45A and 45B are best viewed together.

IVDS implant 4500 includes two lateral wedges 4510, a coupling 4520 that interconnects lateral wedges 4510, an anterior wedge 4530, a posterior wedge 4540, and an actuator 4550. Coupling 4520 may be integrally formed with one or both of lateral wedges 4510. In one example, coupling 4520 includes two parts cooperating with each other to form a linear joint, such that coupling 4520 is laterally extendable. In this example, each of these two parts may be integrally formed with or connected to a respective one of lateral wedges 4510.

Prior to lateral extension (see FIG. 45A), IVDS implant 4500 has width 4570. In operation, a surgeon uses actuator 4550 to move anterior wedge 4530 and posterior wedge 4540 toward each other, as indicated by respective arrows 4562 and 4564. This forces lateral wedges 4510 laterally outwards, as indicated by arrows 4560, thereby laterally extending IVDS implant 4500 (see FIG. 45B) until laterally outward facing surfaces 4512 of lateral wedges 4510 mechanically couple with respective uncinate joint stabilizers 3910. Actuator 4550 is, for example, a screw that is threaded into (a) posterior wedge 4540 with a left-handed thread and (b) one of anterior wedge 4530 and coupling 4520 with a right-handed thread, or with the opposite configuration of thread handedness.

In one example, IVDS implant 4500 is laterally extendable up to a width 4572 that is between one and ten millimeters greater than width 4572, for example approximately 2-5 millimeters greater than width 4570.

Without departing from the scope hereof, lateral wedges 4510, coupling 4520, anterior wedge 4530, and/or posterior wedge 4540 may have shape different from those shown in FIGS. 45A and 45B, as long as movement of anterior wedge 4530 and posterior wedge 4550 toward each other causes forces lateral wedges 4510 laterally outwards. For example, in the embodiment shown in FIGS. 45A and 45B, laterally outward facing surfaces 4512 are planar and wedge inward relative to each other, so as to be approximately parallel to respective medial facing surfaces 3912 (FIGS. 39A and 39B) of uncinate joint stabilizers 3910 when uncinate joint stabilizers 3910 are mutually converging. However, without departing from the scope hereof, each of laterally outward facing surfaces 4512 may be convex, or form a smaller lateral protrusion, to relax requirements to laterally outward facing surfaces 4512 being parallel to respective medial facing surfaces 3912.

Figure 46A:
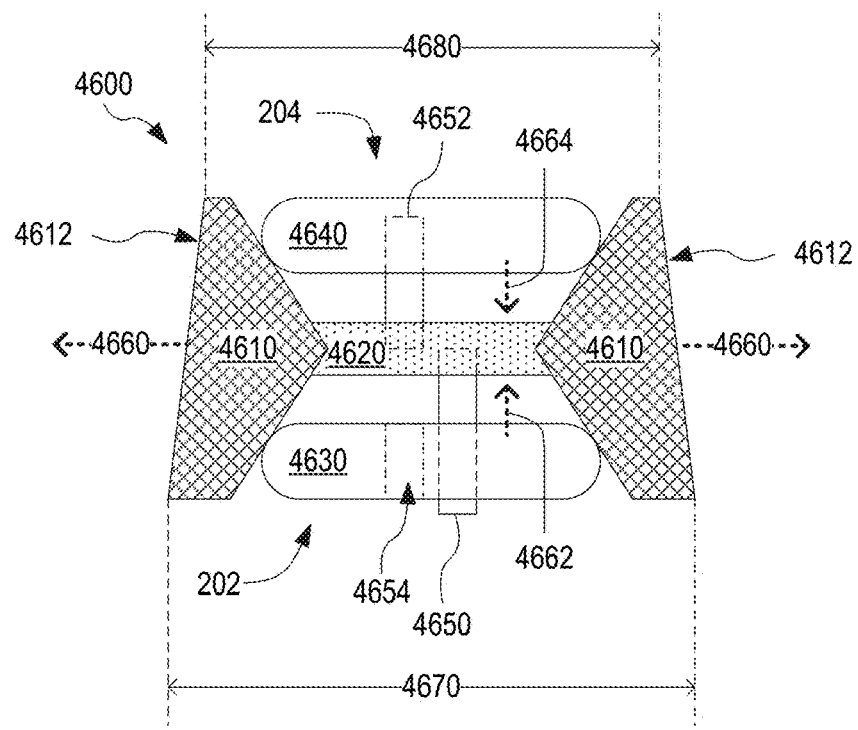
FIGS. 46A and 46B illustrate an angle-adjustable, laterally-extendable intervertebral-disc-space implant configured to mechanically couple, across the intervertebral disc space, between uncinate joint stabilizers positioned in the uncinate joints, according to an embodiment.
Figure 46B:
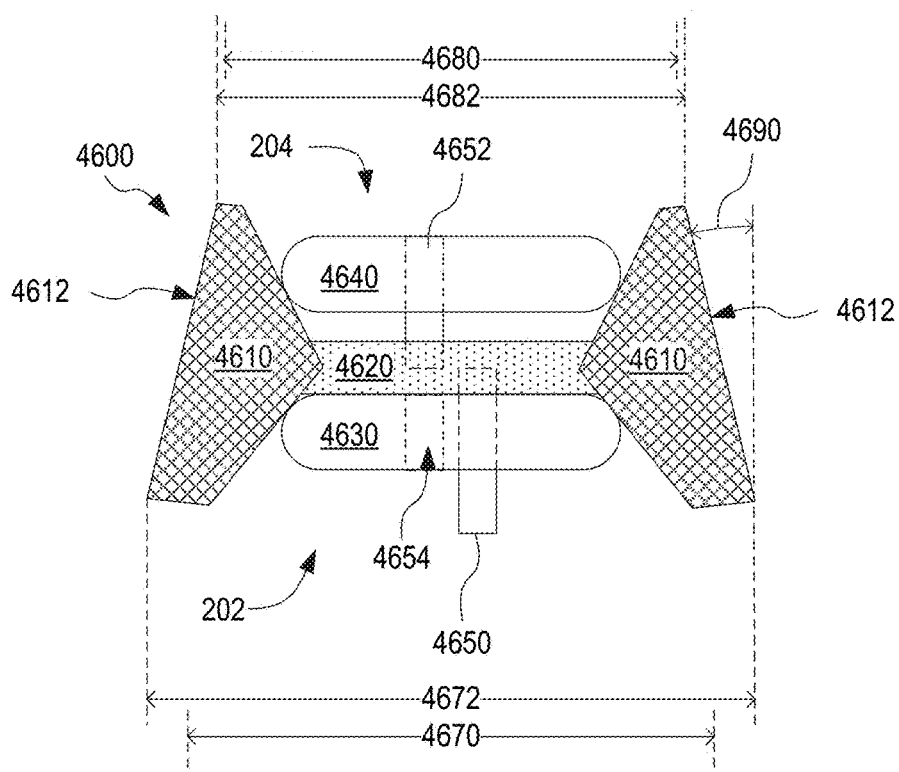

FIGS. 46A and 46B illustrate, in axial view, one exemplary laterally-extendable, laterally-extendable IVDS implant 4600 configured to mechanically couple, across intervertebral disc space 140, between uncinate joint stabilizers 3910 positioned in uncinate joints 120. IVDS implant 4600 is an embodiment of stabilizing bridge 3920. FIG. 46A shows IVDS implant 4600 prior to being laterally extended, and FIG. 46B shows IVDS implant 4600 when laterally extended. FIGS. 46A and 46B are best viewed together.

IVDS implant 4600 is similar to IVDS implant 4500 except that, upon lateral extension of IVDS implant 4600, it is possible to adjust the wedge angle 4690 of laterally outward facing surfaces 4612 of IVDS implant 4600. This angle adjustability may serve to match the convergence angle of uncinate joint stabilizers 3910 when positioned in uncinate joints 120, so as to improve the mechanical coupling between IVDS implant 4600 and uncinate joint stabilizers 3910.

IVDS implant 4600 includes two lateral wedges 4610, a coupling 4620 that interconnects lateral wedges 4610, an anterior bar 4630, a posterior bar 4640, and two actuators 4650. Lateral wedges 4610 and coupling 4620 may similar to lateral wedges 4510 and coupling 4520, respectively, except that lateral wedges 4610 and coupling 4620 are cooperatively configured to allow for variation in wedge angle 4690. Without departing from the scope hereof, the shapes of lateral wedges 4610, coupling 4620, anterior bar 4630, and/or posterior bar 4640 may deviate from those shown in FIGS. 46A and 46B.

Prior to lateral extension (see FIG. 46A), IVDS implant 4600 has anterior width 4670 and posterior width 4680. In operation, a surgeon uses actuator 4650 to move anterior bar 4630 in a posterior direction 4662, and/or the surgeon uses actuator 4652 to move posterior bar 4640 in an anterior direction 4664. The surgeon may access actuator 4652 through an optional opening 4654 in anterior bar 4630. This movement of anterior bar 4630 and/or posterior bar 4640 forces lateral wedges 4610 laterally outwards, as indicated schematically by arrows 4660, thereby laterally extending IVDS implant 4600 (see FIG. 46B) until laterally outward facing surfaces 4612 of lateral wedges 4610 mechanically couple with respective uncinate joint stabilizers 3910. By independently adjusting the position of anterior bar 4630 and the position of posterior bar 4640, it is possible to adjust each of the anterior width and the posterior width of IVDS implant 4600, and thereby match both the distance between uncinate joint stabilizers 3910 and the convergence angle of uncinate joint stabilizers 3910. IVDS implant 4600 may be laterally extended to achieve an anterior width 4672 and a posterior width 4682 that are greater than anterior width 4670 and posterior width 4680, respectively.

Figure 47A:
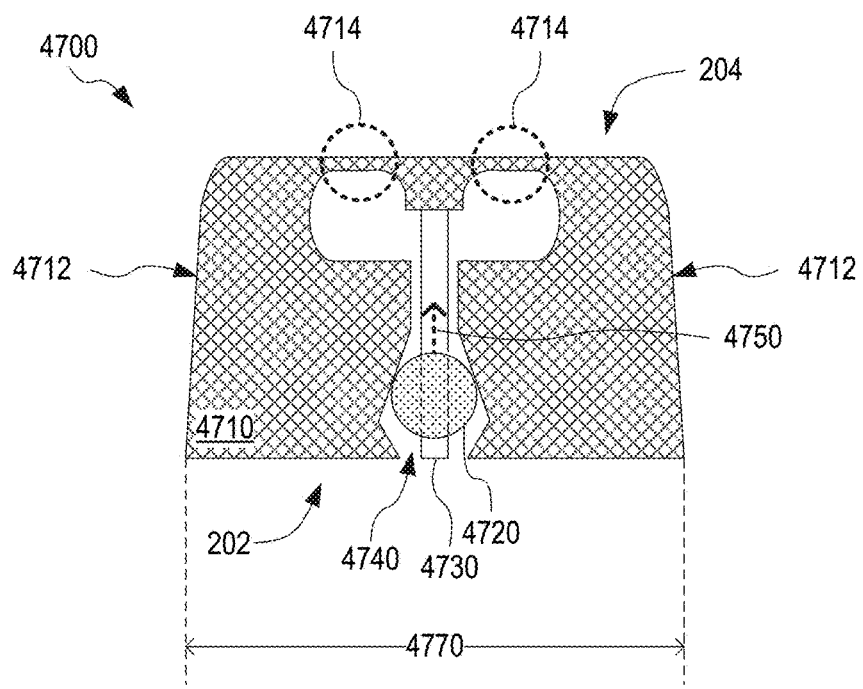
FIGS. 47A and 47B illustrate a flexion-based laterally-extendable intervertebral-disc-space implant configured to mechanically couple, across the intervertebral disc space, between uncinate joint stabilizers positioned in the uncinate joints, according to an embodiment.
Figure 47B:
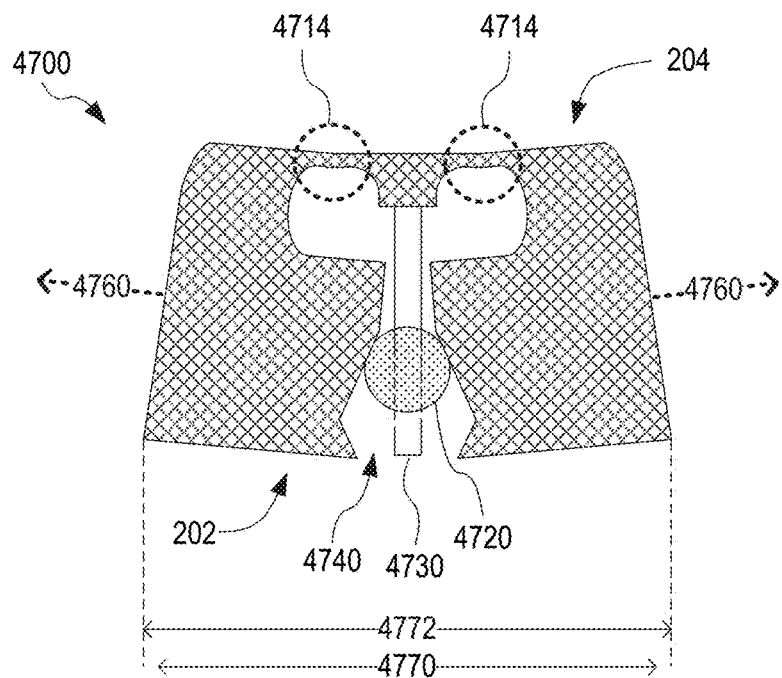

FIGS. 47A and 47B illustrate, in axial view, one exemplary flexion-based laterally-extendable IVDS implant 4700 configured to mechanically couple, across intervertebral disc space 140, between uncinate joint stabilizers 3910 (FIGS. 39A and 39B) positioned in uncinate joints 120. IVDS implant 4700 is an embodiment of stabilizing bridge 3920. FIG. 47A shows IVDS implant 4700 prior to being laterally extended, and FIG. 47B shows IVDS implant 4700 when laterally extended. FIGS. 47A and 47B are best viewed together.

IVDS implant 4700 includes a wedge body 4710, a separator 4720, and an actuator 4730. Wedge body 4710 has laterally outward facing surfaces 4712, at least two flexible sections 4714, and a tapered opening 4740. Actuator 4730 couples separator 4720 to wedge body 4710.

Prior to lateral extension (see FIG. 47A), IVDS implant 4700 has width 4770. In operation, a surgeon uses actuator 4730 to drive separator 4720 in a posterior direction 4750 within tapered opening 4740. Separator 4720 in turn expands tapered opening 4740 and causes flexion in flexible sections 4714 to move laterally outward facing surfaces 4712 laterally outward (as indicated by arrows 4760). This results in extension of the width of IVDS implant 4700 to a width 4772 that is greater than width 4770.

In one example, IVDS implant 4700 is laterally extendable up to a width 4772 that is between one and ten millimeters greater than width 4772, for example approximately 2-5 millimeters greater than width 4770.

In the embodiment shown in FIGS. 47A and 47B, laterally outward facing surfaces 4712 are planar and wedge inward relative to each other, so as to be approximately parallel to respective medial facing surfaces 3912 (FIGS. 39A and 39B) of uncinate joint stabilizers 3910 when uncinate joint stabilizers 3910 are mutually converging. Without departing from the scope hereof, each of laterally outward facing surfaces 4712 may be convex, or form a smaller lateral protrusion, to relax requirements to laterally outward facing surfaces 4712 being parallel to respective medial facing surfaces 3912. In general, it is understood that the shapes of individual features of IVDS implant 4700 may be different from those depicted in FIGS. 47A and 47B, and that IVDS implant 4700 is only one example of a more general IVDS implant that may laterally extend through flexion.

Figure 48:
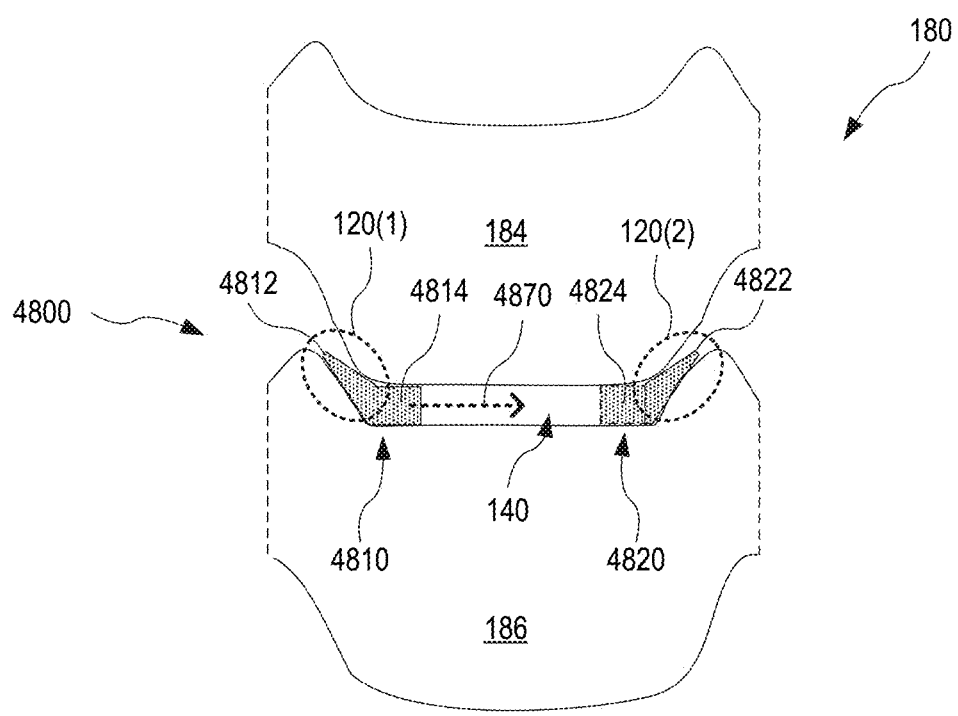
FIG. 48 illustrates a system for stabilizing a cervical spine segment utilizing uncinate joint stabilization and further stabilization across the intervertebral disc space, according to an embodiment.

FIG. 48 illustrates, in anterior view, one exemplary system 4800 for stabilizing cervical spine segment 180 utilizing uncinate joint stabilization and further stabilization across intervertebral disc space 140. System 4800 includes a laterally-extendable uncinate joint stabilizer 4810 and an uncinate joint stabilizer 4820. Uncinate joint stabilizer 4810 includes (a) a tapered element 4812 configured to be positioned in one uncinate joint 120 of cervical spine segment 180 and (b) an IVDS implant 4814 connected or integrally formed with tapered element 4812. IVDS implant 4814 is configured to be laterally extended across intervertebral disc space 140 to mechanically couple with uncinate joint stabilizer 4820. Uncinate joint stabilizer 4820 includes a tapered element 4822 configured to be positioned in the uncinate joint 120 of cervical spine segment 180 not occupied by uncinate joint stabilizer 4810. Uncinate joint stabilizer 4820 may further include an IVDS implant 4824 connected or integrally formed with tapered element 4822. Each of tapered elements 4822 may be similar to tapered element 2800.

IVDS implant 4814, optionally in cooperation with IVDS implant 4824, forms an embodiment of stabilizing bridge 3920. Tapered elements 4812 and 4822 are embodiments of uncinate joint stabilizers 3910.

Without departing from the scope hereof, uncinate joint stabilizer 4820 may be replaced with a laterally-extendable uncinate joint stabilizer 4810, such that both of the uncinate joint stabilizers of system 4800 are extendable to mechanically couple with each other in intervertebral disc space 140.

Figure 49:
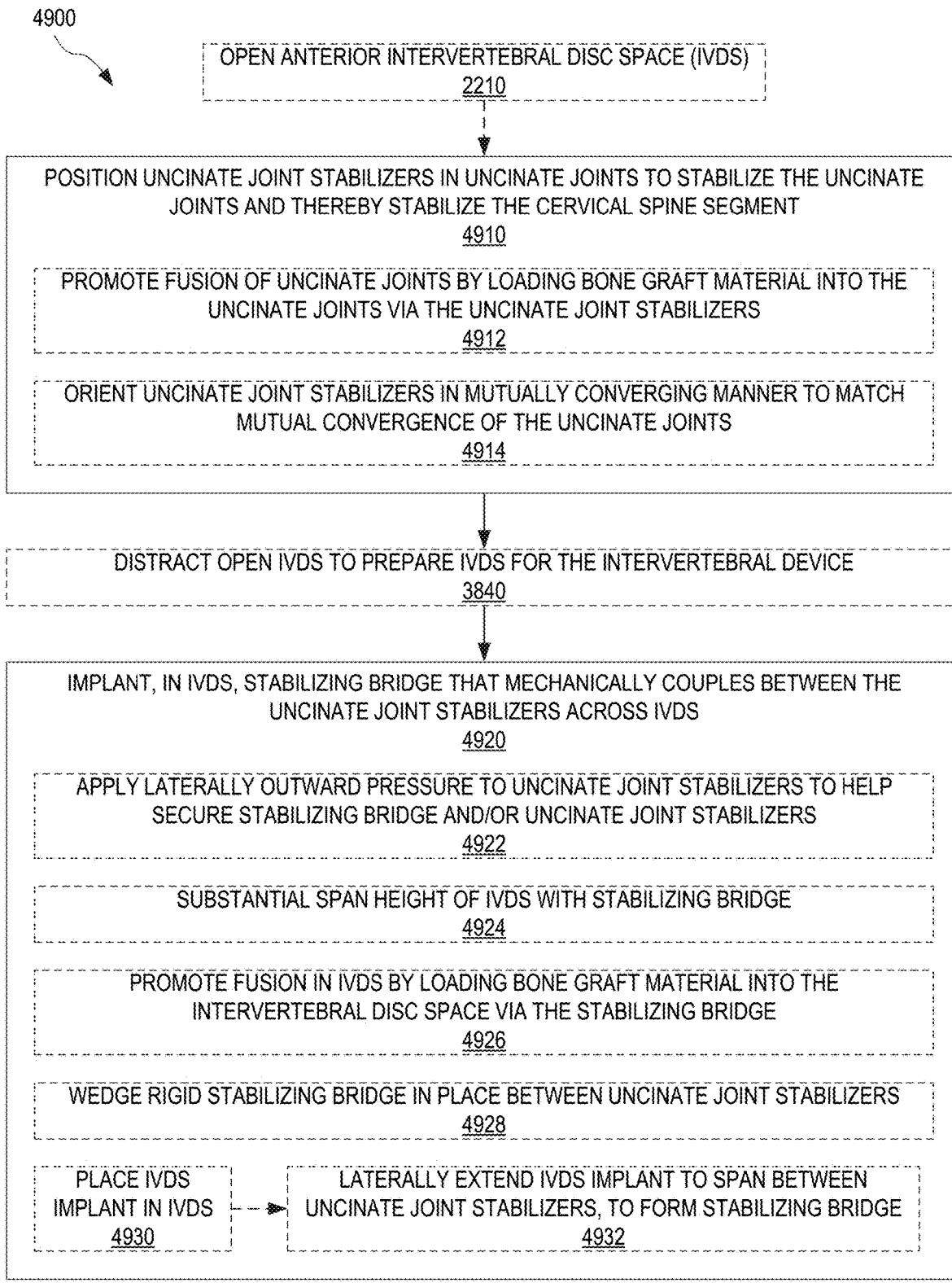
FIG. 49 illustrates a method for stabilizing a cervical spine segment utilizing uncinate joint distraction and stabilization, with additional stabilization across the intervertebral disc space, according to an embodiment.

FIG. 49 illustrates one exemplary method 4900 for stabilizing cervical spine segment 180 utilizing uncinate joint distraction and stabilization, with additional stabilization across intervertebral disc space 140. Method 4900 includes steps 4910 and 4920.

Step 4910 positions uncinate joint stabilizers in uncinate joints 120 of cervical spine segment 180 to stabilize uncinate joints 120 and thereby stabilize cervical spine segment 180. The uncinate joint stabilizers are inserted into uncinate joints 120 from intervertebral disc space 140. In one embodiment, the positioning of uncinate joint stabilizers in uncinate joints 120 in step 4910 also distracts uncinate joints 120. In another embodiment, uncinate joints 120 are at least partly distracted prior to step 4910. In one example of step 4910, a surgeon inserts uncinate joint stabilizers 3910 in uncinate joints 120 from intervertebral disc space 140.

Step 4910 may include a step 4912 of promoting fusion of uncinate joints 120 by loading bone graft material into uncinate joints 120 via the uncinate joint stabilizers. In one example of step 4912, each uncinate joint stabilizer 3910 includes a porous portion, and the pores are loaded with bone graft material. In another example of step 4912, each uncinate joint stabilizer 3910 includes a porous portion substantially composed of bone graft material. In yet another example, each uncinate joint stabilizer 3910 is substantially composed of allograft bone.

Step 4910 may also include a step 4914 of orienting the uncinate joint stabilizers in a mutually converging manner to match the mutual convergence of uncinate joints 120. In one example of step 4914, the surgeon positions uncinate joint stabilizers 3910 in mutually converging uncinate joints 120 with uncinate joint stabilizers 3910 lining up with the converging uncinate joints 120, respectively.

Step 4920 implants, in intervertebral disc space 140, a stabilizing bridge that mechanically couples between the uncinate joint stabilizers across intervertebral disc space 140. In one example of step 4920, the surgeon implants stabilizing bridge 3920 in intervertebral disc space 140 as discussed above in reference to FIGS. 39A and 39B. Step 4920 may include one, two, or all of steps 4922, 4924, and 4926.

Step 4922 applies laterally outward pressure to the uncinate joint stabilizers to help secure the stabilizing bridge and/or the uncinate joint stabilizers in cervical spine segment 180. In one example, stabilizing bridge 3920 applies laterally outward pressure on uncinate joint stabilizers 3910 to help secure stabilizing bridge 3920 and/or uncinate joint stabilizers 3910, as discussed above in reference to FIGS. 39A and 39B.

Step 4924 implants a stabilizing bridge that substantial spans the height of intervertebral disc space 140. In one example of step 4924, stabilizing bridge 3920 has height 3974 that substantially spans the height of intervertebral disc space 140.

Step 4926 promotes fusion in intervertebral disc space 140 by loading bone graft material into intervertebral disc space 140 via the stabilizing bridge. In one example of step 4926, stabilizing bridge 3920 has one or more voids capable of accommodating bone graft material to promote fusion in intervertebral disc space 140. Step 4926 may load bone graft material may be loaded into the void(s) of stabilizing bridge 3920 before or after inserting stabilizing bridge 3920 into intervertebral disc space 140. In another example of step 4926, at least a portion of stabilizing bridge 3920 is a porous portion substantially composed of bone graft material that promotes fusion in intervertebral disc space 140. One embodiment of method 4900 includes steps 4924 and 4926. In this embodiment, fusion between superior vertebra 184 and inferior vertebra 186 across intervertebral disc space 140 is aided by the stabilizing bridge substantially spanning the full height of intervertebral disc space 140.

Method 4900 may include both step 4912 and step 4926 to promote fusion in both uncinate joints 120 and intervertebral disc space 140.

In one embodiment, method 4900 includes a step 4928 of wedging a rigid stabilizing bridge in place between the uncinate joint stabilizers. In one example of step 4928, rigid stabilizing bridge 4020 is wedged into place between uncinate joint stabilizers 3910. In another embodiment, method 4900 includes steps 4930 and 4932. Step 4930 places an IVDS implant in intervertebral disc space 140, and step 4932 laterally extends the IVDS implant to span between the uncinate joint stabilizers, to form the stabilizing bridge. In one example of steps 4930 and 4932, the surgeon places (in step 4930) a laterally extendable embodiment of stabilizing bridge 3920 in intervertebral disc space 140 and laterally extends this stabilizing bridge 3920 (in step 4932) to mechanically couple between uncinate joint stabilizers 3910. Steps 4930 and 4932 utilizes, for example, IVDS implant 4200, IVDS implant 4400, IVDS implant 4500, IVDS implant 4600, or IVDS implant 4700.

Optionally, method 4900 performs step 2210 of method 2200 to open an anterior portion of intervertebral disc space 140 prior to step 4910. Method 4900 may also perform step 3840 of method 3800 (distracting open intervertebral disc space 140) after positioning the uncinate joint stabilizers in uncinate joints 120 in step 4910 and before implanting the stabilizing bridge in intervertebral disc space 140 in step 4920.

FIG. 50 illustrates one exemplary method 5000 for stabilizing cervical spine segment 180 utilizing integrated uncinate joint distraction and stabilization, with additional stabilization across intervertebral disc space 140. Method 5000 is an embodiment of method 4900. Method 5000 includes steps 5010, 5020, and 5040.

Step 5010 performs method 3700, using uncinate joint stabilizers, to at least partly distract uncinate joints 120 with the uncinate joint stabilizers. In one example of step 5010, a surgeon uses uncinate joint stabilizers 3910 to at least partly distract uncinate joints 120, as discussed above in reference to FIG. 37A.

Step 5020 implants uncinate joint stabilizers in uncinate joints 120 to stabilize uncinate joints 120, thereby stabilizing cervical spine segment 180. Step 5020 includes a step 5022 of leaving the uncinate joint stabilizers, used to distract uncinate joints 120 in step 5010, in uncinate joints 120. In one example of step 5020 (with step 5022), the surgeon leaves uncinate joint stabilizers 3910, used to at least partly distract uncinate joints 120 in step 5010, in uncinate joints 120. Step 5020 may include step 4912.

Step 5040 implants, in intervertebral disc space 140, a stabilizing bridge that mechanically couples between the uncinate joint stabilizers across intervertebral disc space 140. In one example, step 5040 implants stabilizing bridge 3920 in intervertebral disc space 140 to mechanically couple between uncinate joint stabilizers 3910. Step 5040 may include a step 5042 of performing step 4920 of method 4900.

Optionally, method 5000 further includes a step 5030 of distracting open intervertebral disc space 140 after positioning the uncinate joint stabilizers in uncinate joints 120 in step 5020 and before implanting the stabilizing bridge in intervertebral disc space 140 in step 5040.

In certain embodiments, method 5000 utilizes a distractor tool, such as actuator 2900 (optionally with extensions 3020), actuator 3100, or actuator 3210. In these embodiments, step 5010 performs method 3700 with steps 3722 and 3732, and optionally also step 3710 and/or step 3734. In one such embodiment, the distractor tool also serves to retract soft tissue 3290. In this embodiment, (a) step 5010 performs method 3700 with step 3724, (b) step 5040 and, optionally, step 5030 are performed with the distractor tool retracting soft tissue 3290 to provide access to intervertebral disc space 140, and (c) the distractor tool is removed in a step 5050 performed after step 5040.

FIG. 51 illustrates one exemplary method 5100 for stabilizing cervical spine segment 180 utilizing uncinate joint distraction and stabilization, with additional stabilization across intervertebral disc space 140, which further utilizes trial implants to determine an optimal size for the uncinate joint stabilizers. Method 5100 is an embodiment of method 4900. Method 5100 includes steps 5110, 5120, 5130, and 5040 (of method 5000).

Step 5110 performs method 3700, using trial implants, to at least partly distract uncinate joints 120 with the trial implants. Step 5110 further uses the trial implants to obtain a measure of the optimal size of uncinate joint stabilizers for uncinate joints 120. In one example of step 5110, a surgeon uses actuator 2900 (optionally with extensions 3020), actuator 3100, or system 3200, together with an embodiment of tapered elements 2800 or tips 3230 configured to be trial implants, to at least partly distract uncinate joints 120, as discussed above in reference to FIG. 37A. While the trial implants are in uncinate joints 120, the surgeon obtains a measure of the optimal uncinate joint stabilizer size from dial 2960. In another example of step 5110, the surgeon inserts an embodiment of tapered elements 2800 or tips 3230, configured to be trial implants, from intervertebral disc space 140 into uncinate joints 120 to at least partly distract uncinate joints 120 and obtain a measure of the optimal uncinate joint stabilizer size.

Step 5120 removes the trial implants. In one example of step 5120, the surgeon removes the trial implants used in step 5110 from cervical spine segment 180.

Step 5130 performs steps 3720 and 3730 of method 3700, using uncinate joint stabilizers, to implant the uncinate joint stabilizers in uncinate joints 120, so as to stabilize uncinate joints 120 and thereby stabilize cervical spine segment 180. Step 5130 uses uncinate joint stabilizers having size chosen based on the measurement obtained in step 5110. In one example of step 5130, the surgeon implants uncinate joint stabilizers 3910 in uncinate joints 120, as discussed above in reference to FIGS. 39A and 39B. Step 5130 may include step 5024.

After performing step 5130, method 5100 performs step 5040 of method 5000 as discussed above in reference to FIG. 50. Optionally, method 5100 includes step 5030 (distracting open intervertebral disc space 140) after step 5130 and before step 5040.

In certain embodiments, method 5100 utilizes a distractor tool, such as actuator 2900 (optionally with extensions 3020), actuator 3100, or system 3200. In these embodiments, (a) step 5110 performs method 3700 with steps 3722 and 3732, and optionally also step 3710 and/or step 3734, (b) step 5120 removes the trial implants using the distractor tool, and (c) step 5130 performs steps 3720 and 3730 with steps 3722 and 3732, respectively, and optionally also step 3710 and/or step 3734. In one such embodiment, the distractor tool also serves to retract soft tissue 3290. In this embodiment, (a) step 5110 performs method 3700 with step 3724, (b) step 5140 and, optionally, step 5130 are performed with the distractor tool retracting soft tissue 3290 to provide access to intervertebral disc space 140, and (c) the distractor tool is removed in step 5050 performed after step 5140.

Figure 52:
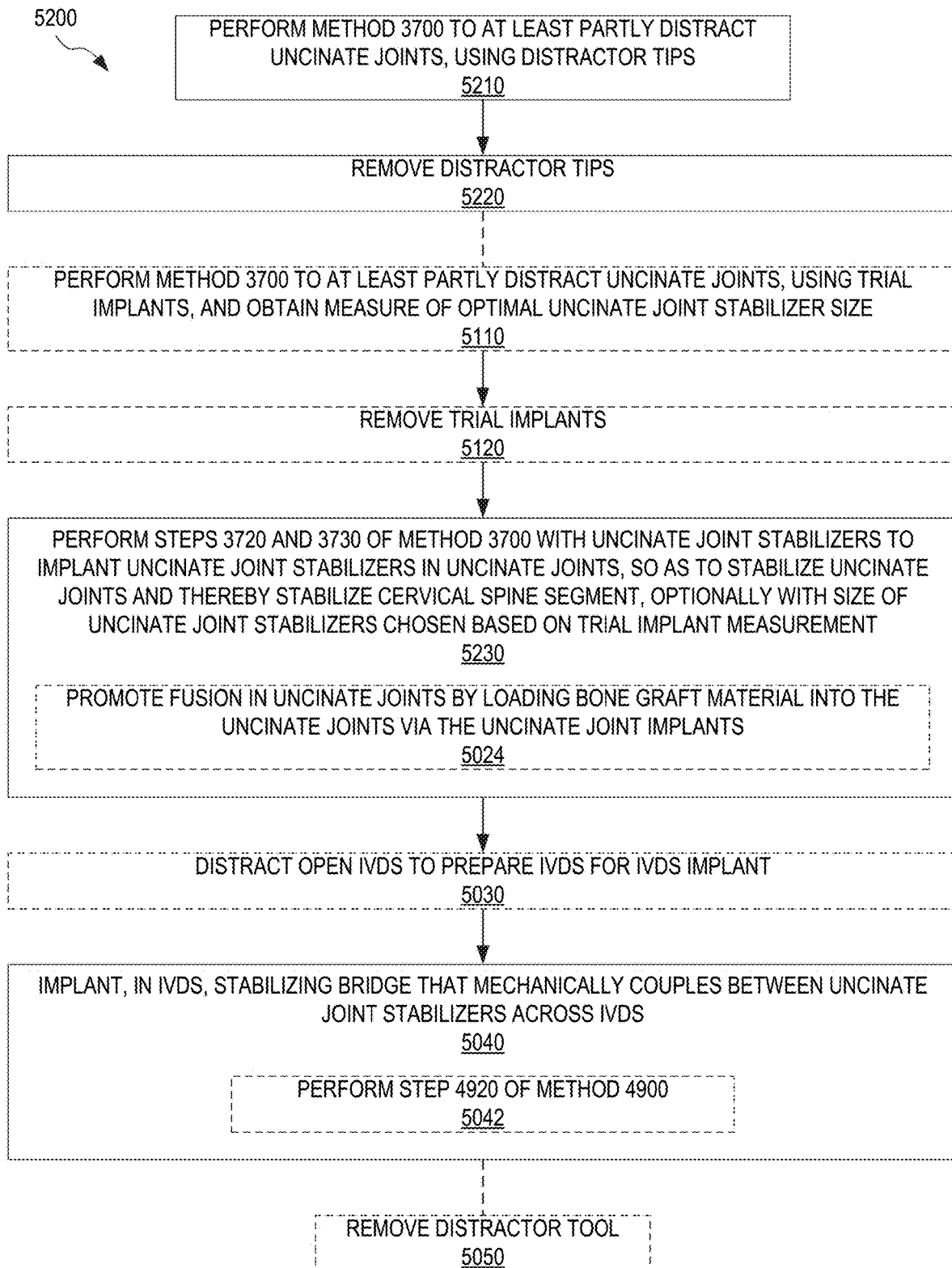
FIG. 52 illustrates a method for stabilizing a cervical spine segment utilizing separate uncinate joint distraction and stabilization, with additional stabilization across the intervertebral disc space, according to an embodiment.

FIG. 52 illustrates one exemplary method 5200 for stabilizing cervical spine segment 180 utilizing separate uncinate joint distraction and stabilization, with additional stabilization across intervertebral disc space 140. Method 5200 is an embodiment of method 4900. Method 5200 includes steps 5210, 5220, 5230, and 5040 (of method 5000).

Step 5210 performs method 3700, using distractor tips, to at least partly distract uncinate joints 120 with the distractor tips. In one example of step 5110, a surgeon uses actuator 2900 (optionally with extensions 3020), actuator 3100, or system 3200, together with an embodiment of tapered elements 2800 or tips 3230, to at least partly distract uncinate joints 120 as discussed above in reference to FIG. 37A.

Step 5220 removes the distractor tips from cervical spine segment 180. In one example of step 5220, the surgeon removes the distractor tips used in step 5210 from cervical spine segment 180.

Step 5230 performs steps 3720 and 3730 of method 3700, using uncinate joint stabilizers, to implant the uncinate joint stabilizers in uncinate joints 120, so as to stabilize uncinate joints 120 and thereby stabilize cervical spine segment 180. In one example of step 5230, the surgeon implants uncinate joint stabilizers 3910 in uncinate joints 120, as discussed above in reference to FIGS. 39A and 39B. Step 5130 may include step 5024.

After performing step 5230, method 5200 performs step 5040 of method 5000 as discussed above in reference to FIG. 50. Optionally, method 5200 includes step 5030 (distracting open intervertebral disc space 140) after step 5230 and before step 5040.

In one embodiment, method 5200 further includes steps 5110 and 5120 of method 5000, performed between steps 5220 and 5230, to determine an optimal size for the uncinate joint stabilizers to be implanted in step 5230. In this embodiment, step 5230 implants uncinate joint stabilizers having size based upon the measurement obtained in step 5110.

In certain embodiments, method 5100 utilizes a distractor tool, such as actuator 2900 (optionally with extensions 3020), actuator 3100, or system 3200. In these embodiments, (a) step 5210 performs method 3700 with steps 3722 and 3732, and optionally also step 3710 and/or step 3734, (b) step 5220 removes the distractor tips using the distractor tool, (c) steps 5110 and 5120 are performed with the distractor tool, and (d) step 5230 performs steps 3720 and 3730 with steps 3722 and 3732, respectively, and optionally also step 3710 and/or step 3734. In one such embodiment, the distractor tool also serves to retract soft tissue 3290. In this embodiment, (a) step 5040 and, optionally, step 5030 are performed with the distractor tool retracting soft tissue 3290 to provide access to intervertebral disc space 140, and the distractor tool is removed in step 5050 performed after step 5040.

Figure 53:
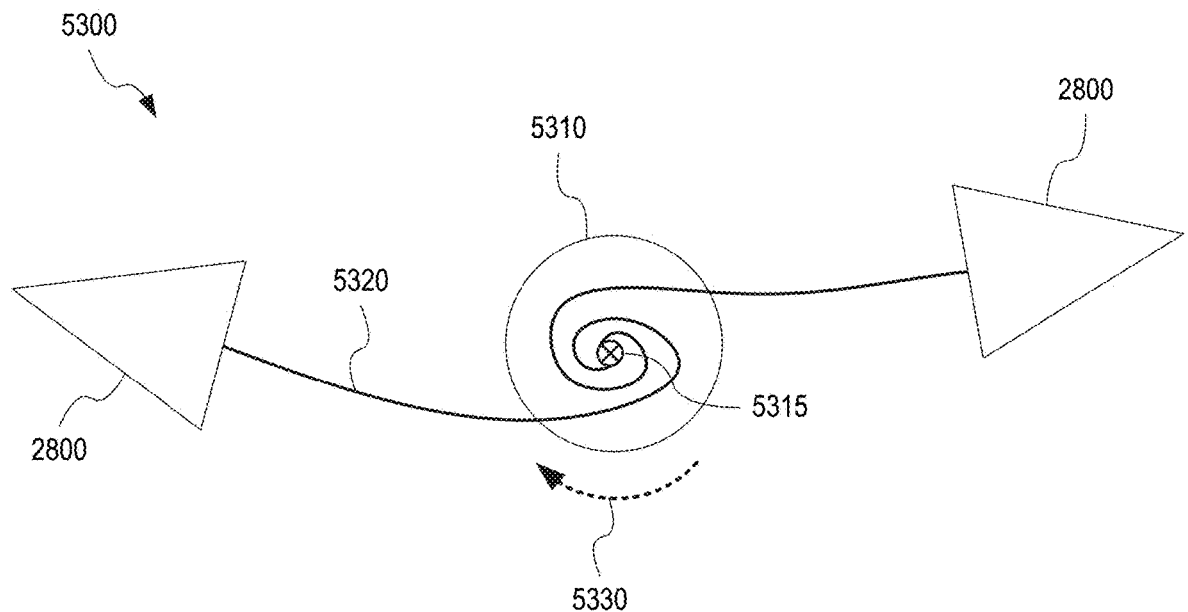
FIG. 53 illustrates an implant-loading system for stabilizing the uncinate joints of a cervical spine segment from the intervertebral disc space, according to an embodiment.

FIG. 53 illustrates one exemplary implant-loading system 5300 for stabilizing uncinate joints 120 of cervical spine segment 180 (FIG. 1) from intervertebral disc space 140. Implant-loading system 5300 may be utilized in step 2414 of method 2400 (FIG. 24).

Implant-loading system 5300 includes a cage 5310 with a rotation mechanism 5315. Implant-loading system 5300 further includes a pair of tapered elements 2800 (FIG. 28) and a pair of connectors 5320. Each connector 5320 connects a respective tapered element 2800 to rotation mechanism 5315. Connectors 5320 are wound around rotation mechanism in a spiral pattern. Connectors 5320 may be sheets, for example made of metal, plastic, or a combination thereof. Upon clockwise rotation of rotation mechanism 5315 (as indicated by arrow 5330), tapered elements 2800 move away from cage 5310. Without departing from the scope hereof, rotation mechanism 5315 may be configured to move tapered elements 2800 away from cage 5310 upon counter-clockwise rotation of rotation mechanism 5315.

In one embodiment, cage 5310 has at least one void capable of accommodating bone graft material to promote fusion in intervertebral disc space 140. Bone graft material may be loaded into the void(s) of cage 5310 before or after inserting cage 5310 into intervertebral disc space 140. This embodiment of cage 5310 is compatible with step 2252 of method 2200 and with step 2422 of method 2400. In another embodiment, at least a portion of cage 5310 is a porous portion substantially composed of bone graft material that promotes fusion in intervertebral disc space 140. This embodiment of cage 5310 is compatible with step 2252 of method 2200 and with step 2422 of method 2400. Cage 5310 may be non-load bearing or partial-load bearing, as discussed in reference to FIG. 22.

Without departing from the scope hereof, spiral-wound connectors 5320 may be replaced by linear connectors having teeth that couple with a gear of rotation mechanism 5315.

Figure 54:
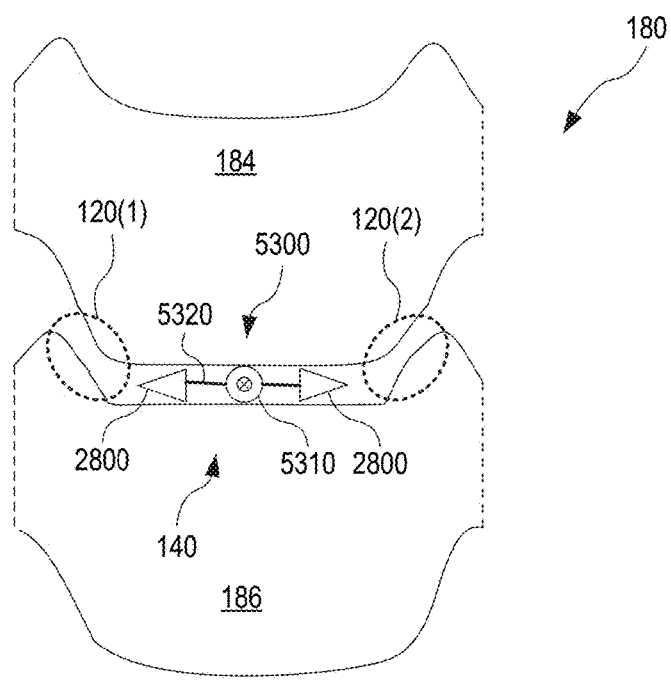
FIG. 54 shows the implant-loading system of FIG. 53 as implemented in the method of FIG. 24, according to an embodiment.

FIG. 54 shows implant-loading system 5300 (FIG. 53) as implemented in step 2414 of method 2400 (FIG. 24). Implant-loading system 5300 is inserted into intervertebral disc space 140. A surgeon rotates rotation mechanism 5315 to move tapered elements 2800 into uncinate joints 120 of cervical spine segment 180. The surgeon may utilize a tool, such as a phillips-head screwdriver/drill, a star-head screwdriver/drill, or a hexagonal wrench, to actuate rotation mechanism 5315.

In an alternate embodiment not shown in FIGS. 53 and 54, cage 5310 is replaced with an IVDS device that is configured to promote fusion in intervertebral disc space 140 and/or share the load of cervical spine segment 180 with tapered elements 2800. This IVDS device may be configured to carry bone graft material, or include allograft bone. Furthermore, this IVDS device may utilize other mechanisms than rotation mechanism to load tapered elements 2800 into uncinate joints 120.

Combinations of Features

Features described above as well as those claimed below may be combined in various ways without departing from the scope hereof. For example, it will be appreciated that aspects of one uncinate joint stabilizer, or associated system or method, described herein may incorporate or swap features of another uncinate joint stabilizer, or associated system or method, described herein. The following examples illustrate possible, non-limiting combinations of embodiments described above. It should be clear that many other changes and modifications may be made to the methods and device herein without departing from the spirit and scope of this invention:

(A1) A method for stabilizing a cervical spine segment may include implanting a respective uncinate joint stabilizer into each uncinate joint of the cervical spine segment to stabilize the uncinate joints and thereby stabilize the cervical spine segment.

(A2) In the method denoted as (A1), in the step of implanting, each uncinate joint stabilizer may be configured to preserve motion of the respective uncinate joint.

(A3) In the method denoted as (A1), in the step of implanting, each uncinate joint stabilizer may be configured to promote fusion of the respective uncinate joint. For example, each uncinate joint stabilizer may include bone graft material, or be configured to accept bone graft material, to promote fusion of the respective uncinate joint. Alternatively, in the step of implanting, each uncinate joint stabilizer may be composed of a non-fusing material.

(A4) In the method denoted as (A1), in the step of implanting, each uncinate joint stabilizer may be a temporary uncinate joint stabilizer composed of a biodegradable material, for temporary stabilization of the respective uncinate joint.

(A5) In any of the methods denoted as (A1) through (A4), in the step of implanting, the uncinate joint stabilizers may be configured to cooperate to bear at least a portion of load of the cervical spine segment to maintain spacing between cervical vertebrae of the cervical spine segment.

(A6) In any of the methods denoted as (A1) through (A5), the step of implanting may include inserting each uncinate joint stabilizer along an anterior-to-posterior direction.

(A7) In the method denoted as (A6), the step of inserting may include inserting each uncinate joint stabilizer into the respective uncinate joint while leaving intervertebral disc of the cervical spine segment undisturbed.

(A8) In either or both of the methods denoted as (A6) and (A7), the step of inserting may include inserting each uncinate joint stabilizer percutaneously.

(A9) In any of the methods denoted as (A6) through (A8), each uncinate joint stabilizer may be cannulated, and the step of inserting may include inserting each uncinate joint stabilizer over a guide wire.

(A10) The method denoted as (A9) may further include inserting the guide wire through longus colli muscle.

(A11) Either of both of the methods denoted as (A9) and (A10) may further include inserting the guide wire under imaging guidance.

(A12) In the method denoted as (A8), the step of inserting may include inserting each uncinate joint stabilizer through a respective cannula.

(A13) Any of the methods denoted as (A6) through (A12) may further include, during the step of inserting each uncinate joint stabilizer, monitoring, using imaging guidance, locations of (a) each uncinate joint stabilizer and (b) instrumentation used to insert each uncinate joint stabilizer.

(A14) In the method denoted as (A13), the step of monitoring may include monitoring the locations relative to vertebral artery on side of spine associated with the uncinate joint stabilizer, to prevent damaging the vertebral artery.

(A15) Any of the methods denoted as (A6) through (A14) may further include distracting each uncinate joint.

(A16) In the method denoted as (A15), the step of distracting may include distracting each uncinate joint using a distraction tool, and removing the distraction tool from the uncinate joint prior to the step of implanting.

(A17) In the method denoted as (A15), the step of distracting may include distracting each uncinate joint using the respective uncinate joint stabilizer during the step of inserting.

(A18) In any of the methods denoted as (A6) through (A17), each uncinate joint stabilizer may have threads, and the step of inserting may include threading each uncinate joint stabilizer into the respective uncinate joint using the threads.

(A19) The method denoted as (A18) may further include (a) in the step of threading, threading each uncinate joint stabilizer into the respective uncinate joint such that the threads contact uncinate joint surfaces only of a selected one of superior and inferior vertebral bodies of the cervical spine segment, and (b) securing each uncinate joint stabilizer to only the selected one of superior and inferior vertebral bodies to preserve motion of the cervical spine segment.

(A20) In the method denoted as (A19), the step of securing may include utilizing tension band formed by at least one ligament of the cervical spine segment.

(A21) In either or both of the methods denoted as (A19) and (A20), the step of securing may include, for each uncinate joint stabilizer, affixing mounting hardware to the uncinate joint stabilizer and the vertebral body.

(A22) In the method denoted as (A18), in the step of inserting, and for each uncinate joint, the threads may contact both superior and inferior surfaces of the uncinate joint.

(A23) The method denoted as (A1) may further include (a) in the step of implanting, inserting each uncinate joint stabilizer into the respective uncinate joint along a medial-to-lateral direction starting from intervertebral disc space of the cervical spine segment, and (b) securing each uncinate joint stabilizer to the respective uncinate joint.

(A24) In the method denoted as (A23), in the step of inserting each uncinate joint stabilizer, each uncinate joint stabilizer may include a tapered implant element for interfacing with superior and inferior uncinate joint surfaces, and the step of inserting each uncinate joint stabilizer may include, for each uncinate joint, distracting the uncinate joint by inserting the uncinate joint stabilizer into the uncinate joint along the medial-to-lateral direction with thinner portion of the tapered implant element facing the uncinate joint.

(A25) In the method denoted as (A24), the step of securing may include securing each uncinate joint stabilizer to the respective uncinate joint using features protruding from the tapered implant element.

(A26) In either or both of the methods denoted as (A24) and (A25), the step of securing may include securing each uncinate joint stabilizer to the respective uncinate joint by, in part, utilizing tension band formed by at least one ligament associated with the respective uncinate joint.

(A27) Any of the methods denoted as (A24) through (A26) may further include, before the step of distracting, opening anterior portion of the intervertebral disc space to open access path for the uncinate joint stabilizers.

(A28) Any of the methods denoted as (A24) through (A27) may further include (a) in the step of distracting, temporarily securing each uncinate joint stabilizer to the respective uncinate joint using features protruding from the tapered implant element, (b) after the step of distracting, performing cervical discectomy to remove at least a portion of intervertebral disc, (c) after the step of performing cervical discectomy, further distracting each uncinate joint by moving, along the medial-to-lateral direction, each uncinate joint stabilizer further into the respective uncinate joint, and (d) after the step of further distracting, securing each uncinate joint stabilizer to the respective uncinate joint using the features protruding from the tapered implant element.

(A29) In the method denoted as (A28), each of the steps of distracting, performing cervical discectomy, and further distracting may include moving each uncinate joint stabilizer using an actuator mechanically coupled with the uncinate joint stabilizers.

(A30) The method denoted as (A23) may further include, before the step of inserting each uncinate joint stabilizer, (a) opening anterior portion of the intervertebral disc space to open access path for tapered trial implants and (b) distracting the uncinate joints by inserting each tapered trial implant into a respective uncinate joint along the medial-to-lateral direction.

(A31) In the method denoted as (A30), the step of distracting may include using an actuator to insert each tapered trial implant into the respective uncinate joint to distract the respective uncinate joint, wherein the actuator accesses the tapered trial implants from anterior side of the cervical spine segment.

(A32) In the method denoted as (A31), the step of distracting may include using the actuator to distract both uncinate joints simultaneously.

(A33) Any of the methods denoted as (A30) through (A32) may further include temporarily securing each tapered trial implant to the respective uncinate joint using features protruding from the tapered trial implant.

(A34) Any of the methods denoted as (A30) through (A33) may further include, after the step of distracting and before the step of inserting each uncinate joint stabilizer, performing cervical discectomy to remove at least a portion of intervertebral disc of the cervical spine segment.

(A35) In the method denoted as (A34), the step of performing cervical discectomy may include mechanically coupling discectomy instrumentation to the tapered trial implants, and using the discectomy instrumentation to remove the at least a portion of intervertebral disc.

(A36) In the method denoted as (A35), the discectomy instrumentation may include a soft tissue retractor.

(A37) Any of the methods denoted as (A34) through (A36) may further include removing each tapered trial implant after the step of performing cervical discectomy, and the step of inserting each uncinate joint stabilizer further comprising distracting each uncinate joint by moving, along a medial-to-lateral direction, each uncinate joint stabilizer into the respective uncinate joint.

(A38) In any of the methods denoted as (A30) through (A37), the step of inserting each uncinate joint stabilizer may include moving the uncinate joint stabilizer using an actuator mechanically coupled with the uncinate joint stabilizers.

(A39) Any of the methods denoted as (A23) through (A38) may further include, after the step of inserting each uncinate joint stabilizer, depositing bone graft material in the intervertebral disc space to promote fusion of the cervical spine segment.

(A40) Any of the methods denoted as (A23) through (A39) may further include, after the step of inserting each uncinate joint stabilizer, placing an intervertebral-disc-space (IVDS) implant in the intervertebral disc space.

(A41) In the method denoted as (A40), the step of placing an IVDS implant may include mechanically coupling the IVDS implant with the uncinate joint stabilizers.

(A42) In the method denoted as (A41), the step of mechanically coupling may include adjusting lateral dimension of the IVDS implant to match distance between the uncinate joint stabilizers.

(A43) In any of the methods denoted as (A40) through (A42), the step of securing each uncinate joint stabilizer comprising utilizing mechanical coupling with the IVDS implant.

(B1) A system for stabilizing a cervical spine segment may include a pair of uncinate joint stabilizers for stabilizing a respective pair of uncinate joints of the cervical spine segment, wherein each uncinate joint stabilizer is elongated along a lengthwise dimension and configured for placement in the respective uncinate joint with the lengthwise dimension substantially oriented along an anterior-to-posterior direction of the cervical spine segment, and wherein each uncinate joint stabilizer has height in a heightwise dimension orthogonal to the lengthwise dimension and the height is configured to define spacing of the respective uncinate joint.

(B2) In the system denoted as (B1), the height may be in the range from two millimeters to seven millimeters, and/or the length may be in the range from six to eighteen millimeters.

(B3) In either or both of the systems denoted as (B1) and (B2), each uncinate joint stabilizer may have length in the lengthwise dimension and width in a widthwise dimension orthogonal to the lengthwise and heightwise dimensions, wherein the width is less than the length and greater than the height.

(B4) In the system denoted as (B3), the width and height may be compatible with percutaneous insertion of each uncinate joint stabilizer into the respective uncinate joint along an anterior-to-posterior direction.

(B5) In either or both of the systems denoted as (B3) and (B4), each of the width and the height may be no greater than 10 millimeters.

(B6) In any of the systems denoted as (B1) through (B5), each uncinate joint stabilizer may include a textured surface for securing the uncinate joint stabilizer to the respective uncinate joint.

(B7) In any of the systems denoted as (B1) through (B6), each uncinate joint stabilizer may be configured for insertion into the respective uncinate joint along an anterior to posterior direction; and the system may further include, for each uncinate joint stabilizer, a locking lever coupled to trailing or leading end of the uncinate joint stabilizer, wherein the interface between the uncinate joint stabilizer and the locking lever is configured to allow rotation of the locking lever about an axis in the lengthwise dimension, wherein extent of the locking lever in a first dimension transverse to the lengthwise dimension is less than the height to allow insertion of the uncinate joint stabilizer without the locking lever contacting surfaces of the respective uncinate joint, and wherein extent of the locking lever in a second dimension orthogonal to the first dimension and the lengthwise dimension is greater than the height to lock the locking lever to at least one surface of the uncinate joint by rotating the locking lever about the axis so as to secure the uncinate joint stabilizer in the respective uncinate joint.

(B8) In the system denoted as (B7), the locking lever may include a jagged surface for locking the locking lever to the at least one surface.

(B9) In either of both of the systems denoted as (B7) and (B8), when the locking lever is oriented to align the second dimension with the heightwise dimension, the locking lever may extend beyond the uncinate joint stabilizer in both directions away from the axis along the heightwise dimension to enable locking of the locking lever to both superior and inferior surfaces of the respective uncinate joint.

(B10) In either of both of the systems denoted as (B7) and (B8), when the locking lever is oriented to align the second dimension with the heightwise dimension, the locking lever may extend beyond the uncinate joint stabilizer only in one direction away from the axis along the heightwise dimension, to enable locking of the locking lever to only one of superior and inferior surfaces of the respective uncinate joint.

(B11) Any of the systems denoted as (B1) through (B6) may further include, for each uncinate joint stabilizer, a screw coupled to the uncinate joint stabilizer for threading the uncinate joint stabilizer into the respective uncinate joint along the anterior-to-posterior direction by contacting threads of the screw to at least one surface of the respective uncinate joint.

(B12) In the system denoted as (B11), each uncinate joint stabilizer may have two openings that allow the threads to contact the superior and inferior surfaces, respectively, for inserting the uncinate joint stabilizer into the respective uncinate joint by threading the screw into the respective uncinate joint, wherein the interface between the uncinate joint stabilizer and the screw allows for rotation of the uncinate joint stabilizer about axis of screw to rotate the uncinate joint stabilizer around the screw to secure the uncinate joint stabilizer to superior and inferior surfaces of the uncinate joint and define the spacing after inserting the uncinate joint stabilizer into the respective uncinate joint.

(B13) In the system denoted as (B14), each uncinate joint stabilizer having jagged exterior surfaces for securing the uncinate joint stabilizer to the superior and inferior surfaces.

(B14) In any of the systems denoted as (B1) through (B6), each uncinate joint stabilizer may include a generally cylindrical portion with cylinder axis in the lengthwise dimension, wherein the generally cylindrical portion has threads for threading the uncinate joint stabilizer into the respective uncinate joint along the anterior-to-posterior direction.

(B15) In the system denoted as (B14), the generally cylindrical portion may include a porous portion for accommodating bone graft material and bone growth.

(B16) In either or both of the systems denoted as (B14) and (B15), the threads may be interrupted by one or more fenestrations, oriented along the lengthwise direction, wherein the fenestrations are configured to accommodate one or more materials selected from the group consisting of bone graft material, bone growth, and tissue displaced from the respective uncinate joint by the uncinate joint stabilizer.

(B17) In any of the systems denoted as (B14) through (B16), each uncinate joint stabilizer may be cannulated along the cylinder axis for insertion into the respective uncinate joint over a respective guide wire.

(B18) The system denoted as (B17) may further include an interface for coupling the uncinate joint stabilizer to a drill for drilling the uncinate joint stabilizer into the respective uncinate joint over the respective guide wire.

(B19) In the system denoted as (B18), the interface may be located on an end face of the uncinate joint stabilizer, the end face generally facing along the lengthwise direction.

(B20) In any of the systems denoted as (B14) through (B19), each uncinate joint stabilizer may include a tapered portion that (a) is adjacent to the generally cylindrical portion, (b) is offset from the generally cylindrical portion in a direction along the lengthwise dimension, and (c) has decreasing extent transverse to the cylinder axis with increasing distance along the cylinder axis away from the generally cylindrical portion, such that the tapered portion eases insertion of the uncinate joint stabilizer into the respective uncinate joint along the anterior-to-posterior direction.

(B21) In any of the systems denoted as (B14) through (B20), the generally cylindrical portion may have diameter to implement the height.

(B22) In any of the systems denoted as (B14) through (B21), each uncinate joint stabilizer may be configured to expose the threads at least in two opposite-facing directions in the heightwise dimension, to secure the uncinate joint stabilizer to both superior and inferior surfaces of the respective uncinate joint using the threads.

(B23) In any of the systems denoted as (B14) through (B20), each uncinate joint stabilizer may further include comprising a housing for partly containing the generally cylindrical portion, wherein the housing includes (a) an opening from which the threads protrude in a first direction along the heightwise dimension, to allow the threads to contact a selected one of superior and inferior surfaces of the respective uncinate joint, and (b) a material portion shielding the threads from contacting a non-selected one of the superior and inferior surfaces.

(B24) In the system denoted as (B23), the material portion may include a smooth surface for contacting the non-selected one of the superior and inferior surfaces while allowing relative movement between the uncinate joint stabilizer and the non-selected one of the superior and inferior surfaces, to form a motion-preserving uncinate joint stabilizer.

(B25) The system denoted as (B24) may further include mounting hardware for affixing each uncinate joint stabilizer to vertebra associated with the selected one of the superior and inferior surfaces.

(B26) In the system denoted as (B25), the mounting hardware may include a bracket for interconnecting the uncinate joint stabilizers externally to intervertebral disc space of the cervical spine segment.

(B27) In the system denoted as (B26), the bracket may include a portion configured to contact anterior facing surface of vertebral body associated with the selected one of the superior and inferior surfaces.

(B28) In the system denoted as (B27), the portion may include an aperture for accepting a screw at location where the portion contacts the anterior facing surface, to secure the uncinate joint stabilizers to the vertebral body using the bracket and the screw.

(B29) In the system denoted as (B28), the aperture may include a laterally oriented slot to accommodate a range of distances between the uncinate joints.

(B30) Either or both of the systems denoted as (B28) and (B29) may further include the screw.

(B31) In any of the systems denoted as (B1) through (B6), each uncinate joint stabilizer may include a tapered portion for interfacing with superior and inferior surfaces of the respective uncinate joint, wherein the tapered portion has a gradient in height along the widthwise dimension, to enable insertion of the uncinate joint stabilizer into the respective uncinate joint from intervertebral disc space of the cervical spine segment.

(B32) In the system denoted as (B31), the tapered portion may have (a) a first surface for contacting the superior surface of the respective uncinate joint and (b) a second surface for contacting the inferior surface of the respective uncinate joint, wherein each of the first and second surfaces has at least one protruding feature for securing the uncinate joint stabilizer to the respective uncinate joint.

(B33) In either or both of the systems denoted as (B31) and (B32), the tapered portion may have taper angle in range between 10° and 45°.

(B34) Any of the systems denoted as (B31) through (B33) may further include a cage configured for placement in the intervertebral disc space and for inserting, from the intervertebral disc space, the uncinate joint stabilizers into the respective uncinate joints.

(B35) The system denoted as (B34) may further include a pair of connecting elements for connecting the pair of uncinate joint stabilizers, respectively, to the cage, and an actuator, connected to each of the connecting elements, for extending the connecting elements to insert the uncinate joint stabilizers into the uncinate joints, respectively.

(B36) In any of the systems denoted as (B1) through (B35), each uncinate joint stabilizer may be composed of metal.

(B37) In the system denoted as (B36), the metal may be selected from the group consisting of titanium, titanium alloy, stainless steel, cobalt, chromium, and a combination thereof.

(B38) In any of the systems denoted as (B1) through (B35), each uncinate joint stabilizer may include a polymer.

(B39) In the system denoted as (B38), the polymer being selected from the group consisting of (a) polyetheretherketone (PEEK) and (b) other polyaryletherketone (PAEK) material.

(B40) Any of the systems denoted as (B1) through (B35) may be composed of biodegradable material or a non-fusing material.

(B41) In the system denoted as (B40), the biodegradable material may be selected from the group consisting of lactulose, proline, polyglycolic acid, a derivative of polyglycolic acid, poly-L-lactic acid, a derivative of poly-L-lactic acid, and a combination thereof.

(C1) A system for distracting uncinate joints of a cervical spine segment may include two tapered elements and an actuator configured to couple with the tapered elements and change distance between the tapered elements, to insert the tapered elements into the uncinate joints, respectively, from intervertebral disc space of the cervical spine segment.

(C2) In the system denoted as (C1), each of the tapered elements may be elongated in a lengthwise dimension and having height in a heightwise dimension orthogonal to the lengthwise dimension, wherein the height has a gradient in a widthwise dimension orthogonal to the lengthwise and heightwise dimensions to define tapering of the tapered element.

(C3) Either or both of the systems denoted as (C1) and (C2) may further include two extensions for extending the tapered elements, respectively, along the lengthwise dimension, wherein each extension has length sufficient to protrude in anterior direction from the respective uncinate joint, the actuator being coupled to the tapered elements via the extensions.

(C4) In the system denoted as (C3), each extension may include an interface for holding instrumentation for protecting soft tissue.

(C5) In either or both of the systems denoted as (C3) and (C4), each extension may be integrally formed with the respective tapered element.

(C6) In either or both of the systems denoted as (C3) and (C4), each extension may be removably coupled with the respective tapered element.

(C7) In any of the systems denoted as (C1) through (C6), each tapered element may include polymer.

(C8) In any of the systems denoted as (C1) through (C6), each tapered element may include at least one portion for contacting surfaces of the respective uncinate joint, wherein the portion is composed of polymer.

(C9) In any of the systems denoted as (C1) through (C8), the tapered elements may taper away from each other when coupled with the actuator, such that the height of each implant decreases in direction away from the other implant.

(C10) In any of the systems denoted as (C1) through (C9), each tapered element may taper from height less than one millimeter to height no greater than six millimeters.

(C11) In any of the systems denoted as (C1) through (C9), each tapered element may taper from height less than two millimeters to height greater than two millimeters.

(C12) In any of the systems denoted as (C1) through (C11), each tapered element may include features protruding from the tapered element for temporarily securing the tapered elements to the uncinate joints.

(C13) In any of the systems denoted as (C1) through (C12) further including a coupling mechanism for coupling and uncoupling the actuator with the tapered elements.

(C14) In any of the systems denoted as (C1) through (C13), the actuator may include (a) two connecting members for mechanically coupling with the tapered elements, respectively, (b) two handles for actuating the actuator, and (c) a hinge, coupled with the connecting members and the handles, for translating action of the handles to the connecting members.

(C15) In the system denoted as (C14), the hinge may be configured for reverse scissor action.

(C16) In the system denoted as (C14), the hinge may be configured for scissor action.

(C17) Any of the systems denoted as (C1) through (C16) may further include an indicator for indicating separation between the tapered elements when coupled with the actuator.

(D1) A system for stabilizing a cervical spine segment utilizing uncinate joint stabilization may include a stabilizing bridge for bridging across intervertebral disc space of the cervical spine segment to mechanically couple between a pair of uncinate joint stabilizers positioned in a respective pair of uncinate joints of the cervical spine segment.

(D2) In the system denoted as (D1), the stabilizing bridge may be configured to, when positioned in the intervertebral disc space, apply laterally outward pressure on the uncinate joint stabilizers to help secure at least one of (a) the uncinate joint stabilizers and (b) the stabilizing bridge.

(D3) In either of the systems denoted as (D1) and (D2), the stabilizing bridge may have at least one void for accommodating bone graft material to promote fusion of the intervertebral disc space.

(D4) Any of the systems denoted as (D1) through (D3) may further include the uncinate joint stabilizers, wherein each of the uncinate joint stabilizers has a porous portion with pores capable of accommodating bone graft material or a porous portion substantially composed of bone graft material, to promote fusion of the uncinate joints.

(D5) In any of the systems denoted as (D1) through (D4), the stabilizing bridge may have height sufficient to facilitate fusion between superior and inferior vertebrae of the cervical spine segment.

(D6) In any of the systems denoted as (D1) through (D5), the stabilizing bridge may be rigid and configured for wedging between the uncinate joint stabilizers.

(D7) In the system denoted as (D6), at least a portion of the stabilizing bridge may have wedge-shaped cross section in axial plane to enable wedging the stabilizing bridge between the uncinate joint stabilizers while accommodating mutually converging orientation of the uncinate joint stabilizers in the uncinate joints.

(D8) Either of the systems denoted as (D6) and (D7) may further include the uncinate joint stabilizers, wherein (a) each of the uncinate joint stabilizers has a first surface facing the intervertebral disc space and is configured to mechanically couple with a respective second surface of the stabilizing bridge and (b) for each of the uncinate joint stabilizers, at least one of the corresponding first and second surfaces has features increasing friction between the first surface and the second surface, to help secure the stabilizing bridge to the uncinate joint stabilizer.

(D9) In any of the systems denoted as (D6) through (D8), height of the stabilizing bridge may be in range between 3 and 11 millimeters.

(D10) In any of the systems denoted as (D6) through (D9), the stabilizing bridge may be lordotic.

(D11) In any of the systems denoted as (D6) through (D10), lateral extent of the stabilizing bridge may be in range between 15 and 25 millimeters.

(D12) In any of the systems denoted as (D1) through (D5), the stabilizing bridge may include a laterally-extendable intervertebral-disc-space (IVDS) implant for positioning in the intervertebral disc space and subsequent lateral extension to mechanically couple with the uncinate joint stabilizers.

(D13) In the system denoted as (D12), the IVDS implant may have a pair of laterally-outward-facing contact surfaces that, when the IVDS implant is positioned in the intervertebral disc space and after lateral extension of the IVDS implant, apply laterally outward pressure on the respective pair of uncinate joint stabilizers.

(D14) In the system denoted as (D13), when the IVDS implant is mechanically coupled with the uncinate joint stabilizers, the contact surfaces may be mutually converging to accommodate mutually converging orientation of the uncinate joint stabilizers in the uncinate joints.

(D15) In any of the systems denoted as (D12) through (D14), the IVDS implant may be configured to contract in anterior-to-posterior dimension when undergoing lateral extension.

(D16) In any of the systems denoted as (D12) through (D15), the IVDS implant may be configured for lateral extension by at least two millimeters.

(D17) In any of the systems denoted as (D12) through (D16) 2, height of the IVDS implant may be in range between 3 and 11 millimeters.

(D18) Any of the systems denoted as (D1) through (D17) may further include the uncinate joint stabilizers, wherein each of the uncinate joint stabilizers includes a tapered element that (a) is elongated in a lengthwise dimension, (b) is configured for placement in the respective uncinate joint with the lengthwise dimension oriented along a predominantly anterior-to-posterior direction, (c) has height in a heightwise dimension, the height having a gradient along a widthwise dimension to define tapering of the tapered element to facilitate insertion of the uncinate joint stabilizer into the respective uncinate joint from intervertebral disc space of the cervical spine segment, and (d) has a medial surface configured to face the intervertebral disc space and mechanically couple with the stabilizing bridge.

(E1) A method for stabilizing a cervical spine segment utilizing uncinate joint stabilization may include (a) positioning a pair of uncinate joint stabilizers in respective uncinate joints of the cervical spine segment to stabilize the uncinate joints and thereby stabilize the cervical spine segment, and (b) implanting, in intervertebral disc space of the cervical spine segment, a stabilizing bridge that mechanically couples between the uncinate joint stabilizers across intervertebral disc space of the cervical spine segment.

(E2) In the method denoted as (E1), the step of implanting may include using the stabilizing bridge to apply laterally outward pressure to the uncinate joint stabilizers to help secure one or both of the stabilizing bridge and the uncinate joint stabilizers in the cervical spine segment.

(E3) In either of the methods denoted as (E1) and (E2), the step of implanting may include substantially spanning height of the intervertebral disc space with the stabilizing bridge.

(E4) Any of the methods denoted as (E1) through (E3) may further include promoting fusion in the intervertebral disc space by loading bone graft material into the intervertebral disc space via the stabilizing bridge.

(E5) Any of the methods denoted as (E1) through (E4) may further include promoting fusion of the uncinate joints by loading bone graft material into the uncinate joints via the uncinate joint stabilizers.

(E6) In any of the methods denoted as (E1) through (E5), the stabilizing bridge may be rigid and the method may further include (i) in the step of positioning, orienting the uncinate joint stabilizers in a mutually converging manner to match mutual convergence of the uncinate joints, and (ii) in the step of implanting, wedging the stabilizing bridge in place between the uncinate joint stabilizers.

(E7) The method denoted as (E6) may further include preloading the stabilizing bridge with the bone graft material prior to the step of implanting to promote fusion in the intervertebral disc space.

(E8) In any of the methods denoted as (E1) through (E5), the step of implanting may include (i) placing an intervertebral-disc-space (IVDS) implant in the intervertebral disc space, and (ii) after the step of placing, laterally extending the IVDS implant to span between the uncinate joint stabilizers, to form the stabilizing bridge.

(E9) The method denoted as (E8) may further include using the IVDS implant to hold bone graft material in the intervertebral disc space to promote fusion in the intervertebral disc space.

(F1) A tool for distracting uncinate joints of a cervical spine segment may include (a) two connector arms configured to access the cervical spine segment through soft tissue anterior to the cervical spine segment, wherein the connector arms form respective receptacles for holding extensions coupled to respective distractor tips so as to position the distractor tips at distal ends of the connector arms and in the cervical spine segment, and (b) a control coupled to proximate ends of the connector arms and configured to adjust distance between the connector arms, at least at the distal ends, to distract the uncinate joints with the distractor tips.

(F2) In the tool denoted as (F1), each of the receptacles may be a channel in a respective one of the connector arms.

(F3) In either of the tools denoted as (F1) and (F2), each of the receptacles may cooperate with shape of the extensions to restrict rotation of the distractor tips about axis between the distal and proximate ends of the respective one of the connector arms.

(F4) In either of the tools denoted as (F1) and (F2), each of the receptacles may cooperate with shape of the extensions to allow rotation of the distractor tips about axis between the distal and proximate ends of the respective one of the connector arms.

(F5) In any of the tools denoted as (F1) through (F4), each of the connector arms may have width sufficient to retract the soft tissue, when the distal ends of the connector arms are positioned at the cervical spine segment.

(F6) In the tool denoted as (F5), the width may be at least one centimeter.

(F7) In either of the tools denoted as (F5) and (F6), the connector arms may include retractor blades having the width sufficient to retract the soft tissue.

(F8) Any of the tools denoted as (F1) through (F4) may further include retractor blades coupled to the connector arms for retraction of the soft tissue.

(F9) Any of the tools denoted as (F1) through (F8) may further include, for each of the connector arms, a fastener for locking position of a respective one of the distractor tips relative to the connector arm.

(F10) Any of the tools denoted as (F1) through (F9) may further include a dial indicating a measure of distance between the distractor tips.

(F11) Any of the tools denoted as (F1) through (F10) may further include the distractor tips.

(G1) A system for distracting uncinate joints of a cervical spine segment may include a pair of distractor tips for insertion into the uncinate joints, respectively, along a medial-to-lateral direction from intervertebral disc space of the cervical spine segment, to distract the uncinate joints, wherein each of the distractor tips has a lateral side and a medial side respectively facing and facing away from a respective one of the uncinate joints during the insertion, and wherein height of each distractor tip gradually increases from the lateral side at least partway toward the medial side to ease the insertion.

(G2) The system denoted as (G1) may further include a pair of extensions coupled with the distractor tips, wherein each of the extensions is configured for mounting in a respective receptacle of an actuator for adjusting distance between the distractor tips.

(G3) In the system denoted as (G2), each extension may be integrally formed with a respective one of the distractor tips.

(G4) In the system denoted as (G2), each distractor tip and respective extension may be removably coupled to each other such that the distractor tips may be disconnected from the extensions and left in the uncinate joints.

(G5) In the system denoted as (G2), each extension may include an elongated rod.

(G6) In any of the systems denoted as (G1) through (G5), each of the distractor tips may be characterized by rotational symmetry about lengthwise axis of the distractor tip, wherein the lengthwise axis is oriented along a predominantly anterior-to-posterior direction when the distractor tip is positioned in a respective one of the uncinate joints.

(G7) In any of the systems denoted as (G1) through (G5), each of the distractor tips may be larger in a first dimension orthogonal to a lengthwise axis of the distractor tip than in a second dimension orthogonal to both the first dimension and the lengthwise axis, wherein the lengthwise axis is oriented along a predominantly anterior-to-posterior direction when the distractor tip is positioned in a respective one of the uncinate joints.

(G8) In any of the systems denoted as (G1) through (G5), each of the distractor tips may include a tapered portion that is (a) elongated along a lengthwise dimension and (b) configured for insertion into the uncinate joint from intervertebral disc space of the cervical spine segment with the lengthwise dimension oriented along a predominantly anterior-to-posterior direction, wherein the tapered portion has height in a heightwise dimension orthogonal to the lengthwise dimension, and the height has a gradient along a widthwise dimension orthogonal to the lengthwise dimension and the heightwise dimension to define tapering of the tapered portion to facilitate said insertion.

(G9) In the system denoted as (G8), the tapered portion may have taper angle in range between 5° and 60°.

(G10) In the system denoted as (G8), the tapered portion may have taper angle in range between 10° and 45°.

(G11) In any of the systems denoted as (G8) through (G10), minimum height of the tapered portion may be less than 2 millimeters.

(G12) In any of the systems denoted as (G8) through (G11), maximum height of the tapered portion may be between 4 and 10 millimeters.

(G13) In any of the systems denoted as (G8) through (G12), the tapered portion may have generally triangular cross section in plane orthogonal to the lengthwise dimension.

(G14) In the system denoted as (G13), the corner of the triangular cross section associated with leading edge of the tapered element, during the insertion, may be blunt.

(G15) In any of the systems denoted as (G1) through (G14), the distractor tips may be disposable.

(G16) In any of the systems denoted as (G1) through (G14), the distractor tips may be composed of metal.

(G17) In any of the systems denoted as (G1) through (G14), the distractor tips may be composed of polymer.

(G18) In any of the systems denoted as (G1) through (G17), the distractor tips may be configured to be coupled to respective connector arms of an actuator for adjusting distance between the distractor tips by adjusting distance between the connector arms, and the system may further include a pair of retractor blades to be mounted on the connector arms, respectively, for retraction of soft tissue anterior to the cervical spine segment.

(G19) In the system denoted as (G18), the retractor blades may be disposable.

(G20) In the system denoted as (G18), the retractor blades may be composed of metal.

(G21) In the system denoted as (G18), the retractor blades may be composed of polymer.

(H1) A method for distracting a pair of uncinate joints of a cervical spine segment may include positioning a pair of distractor tips in intervertebral disc space of the cervical spine segment, and pushing the pair of distractor tips into the pair of uncinate joints, respectively, from the intervertebral disc space to at least partly distract the uncinate joints.

(H2) The method denoted as (H1) may further include, after the step of pushing, rotating each of the distractor tips to further distract the uncinate joints.

(H3) Either of the methods denoted as (H1) and (H2) may further include (a) in the step of positioning, advancing the distractor tips into the intervertebral disc space using a distractor tool, wherein the distractor tips are attached to respective connector arms of the distractor tool, and (b) in the step of pushing, increasing distance between the connector arms to push the distractor tips into the respective uncinate joints.

(H4) The method denoted as (H3) may further include retracting soft tissue anterior of the cervical spine segment by displacing the soft tissue laterally outward with the connector arms or retractor blades attached to the connector arms, to provide access to the cervical spine segment.

(H5) A method for stabilizing a cervical spine segment utilizing uncinate joint distraction may include (a) performing any of the methods denoted as (H1) through (H4) to at least partly distract the uncinate joints, thereby increasing height of the intervertebral disc space, (b) after the step of increasing height and with the distractor tips in the uncinate joints to maintain the increased height, placing an intervertebral device in the intervertebral disc space, wherein the intervertebral device is configured to stabilize the cervical spine segment, and (c) after the step of placing, removing the distractor tips from the cervical spine segment.

(H6) The method denoted as (H5) may further include, after the step of increasing height, with the distractor tips in the uncinate joints to maintain the increased height, and before the step of placing: distracting open the intervertebral disc space to prepare the intervertebral disc space for the intervertebral device.

(H7) Either of the methods denoted as (H5) and (H6) may further include, prior to the step of performing any of the methods denoted as (H1) through (H4), performing a partial anterior discectomy of the cervical spine segment to allow the distractor tips to access the intervertebral disc space.

(H8) In any of the methods denoted as (H5) through (H7), the step of placing may include placing a fusion cage in the intervertebral disc space to promote fusion of the cervical spine segment.

(H9) In any of the methods denoted as (H5) through (H7), the step of placing may include placing an artificial disc in the intervertebral disc space to stabilize the cervical spine segment while preserving motion thereof.

(H10) A method for stabilizing a cervical spine segment utilizing uncinate joint distraction and stabilization may include (a) performing any of the methods denoted as (H1) through (H4) to at least partly distract the uncinate joints, and (b) implanting uncinate joint stabilizers in the uncinate joints to stabilize the uncinate joints, thereby stabilizing the cervical spine segment.

(H11) The method denoted as (H10) may further include loading bone graft material into the uncinate joints via the uncinate joint stabilizers to promote fusion of the uncinate joints.

(H12) In either of the methods denoted as (H10) and (H11), the step of implanting may include leaving the distractor tips in the uncinate joints to function as the uncinate joint stabilizers.

(H13) Either of the methods denoted as (H10) and (H11) may further include, after the step of performing and before the step of implanting, removing the distractor tips from the cervical spine segment.

(H14) The method denoted as (H13) may further include (i) in the step of positioning, advancing the distractor tips into the intervertebral disc space using an actuator, wherein the distractor tips re attached to respective connector arms of the actuator, (ii) in the step of pushing, increasing distance between the connector arms to push the distractor tips into the respective uncinate joints, (iii) in the step of removing, extracting the distractor tips from the cervical spine segment using the actuator, and (iv) in the step of implanting, (1) advancing the uncinate joint stabilizers into the cervical spine segment using a second tool, wherein the uncinate joint stabilizers are attached to respective connector arms of the second tool, and (2) increasing distance between the connector arms of the second tool to place the uncinate joint stabilizers in the uncinate joints.

(H15) In the method denoted as (H14), the second tool may be the actuator, and the method may further include disconnecting the distractor tips from the connecting arms of the actuator, and connecting the uncinate joint stabilizers to the connecting arms of the actuator.

(H16) Either of the methods denoted as (H14) and (H15) may further include, in the steps of positioning, pushing, and implanting: retracting soft tissue anterior of the cervical spine segment by displacing the soft tissue laterally outward with the connector arms or retractor blades attached to the connector arms, to provide access to the cervical spine segment.

(H17) Any of the methods denoted as (H14) through (H16) may further include (i) after the step of performing and before the step of removing, obtaining a measure of distance between the distractor tips, and (ii) in the step of implanting, implanting the uncinate joint stabilizers with size of the uncinate joint stabilizers being selected according to the measure of the distance.

(H18) In the method denoted as (H17), the step of obtaining may include reading the measure from a dial on an actuator coupled with the distractor tips.

(H19) Any of the methods denoted as (H14) through (H16) may further include (i) after the step of removing, temporarily placing a pair of trial implants into the uncinate joints from the intervertebral disc space to determine optimal size of the uncinate joint stabilizers, and (ii) in the step of implanting, implanting uncinate joint stabilizers of the optimal size.

(H20) The method denoted as (H19) may further include (1) in the step of positioning, advancing the distractor tips into the intervertebral disc space using an actuator, the distractor tips being attached to respective connector arms of the actuator, (2) in the step of pushing, increasing distance between the connector arms to push the distractor tips into the respective uncinate joints, (3) in the step of removing, extracting the distractor tips from the cervical spine segment using the actuator, (4) replacing the distractor tips on the connector arms with the trial implants, (5) in the step of temporarily placing, advancing the trial implants into the cervical spine segment using the actuator, increasing distance between the connector arms to push the trial implants into the respective uncinate joints, and extracting the trial implants from the cervical spine segment using the actuator, and (6) in the step of implanting, advancing the uncinate joint stabilizers into the cervical spine segment, using the actuator, and increasing distance between the connector arms to push the uncinate joint stabilizers into the respective uncinate joints.

(H21) The method denoted as (H20) may further include, in the steps of positioning, pushing, temporarily placing, and implanting: retracting soft tissue anterior of the cervical spine segment by displacing the soft tissue laterally outward with the connector arms or retractor blades attached to the connector arms, to provide access to the cervical spine segment.

(H22) Any of the methods denoted as (H19) through (H21) may further include, during the step of temporarily placing, obtaining a measure of distance between the trial implants to determine the optimal size.

(H23) In the method denoted as (H22), the step of obtaining may include reading the measure from a dial on an actuator coupled with the trial implants.

(H24) Any of the methods denoted as (H1) through (H2#) may further include, after the step of implanting uncinate joint stabilizers, implanting, in intervertebral disc space of the cervical spine segment, a stabilizing bridge that mechanically couples between the uncinate joint stabilizers across the intervertebral disc space.

(H25) The method denoted as (H24) may further include loading bone graft material into the intervertebral disc space via the stabilizing bridge to promote fusion of the intervertebral disc space.

(H26) Either of the methods denoted as (H24) and (H25) may further include loading bone graft material into the uncinate joints via the uncinate joint stabilizers to promote fusion of the uncinate joints.

Changes may be made in the above devices, systems, and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present devices, systems, and methods, which, as a matter of language, might be said to fall therebetween.

What is claimed is:

1. A device for stabilizing a cervical spine segment, comprising:
   first and second uncinate-joint portions configured for positioning in respective uncinate joints of the cervical spine segment; and
   an intervertebral-disc-space portion configured to extend from the first uncinate-joint portion to the second uncinate-joint portion, to span across intervertebral disc space of the cervical spine segment, wherein the intervertebral-disc-space portion includes a top surface configured to directly contact the superior vertebra between the respective uncinate joints, and a bottom surface configured to directly contact the inferior vertebra between the respective uncinate joints;

the intervertebral-disc-space portion and the first and second uncinate-joint portions being cooperatively configured such that, when the device is implanted in the cervical spine segment, each of the first and second uncinate-joint portions extends from the intervertebral-disc-space portion to a location, in the respective uncinate joint, that is superior to the intervertebral-disc-space portion.

2. The device of claim 1, wherein a thickness of each of the first and second uncinate-joint portions decreases in direction away from the intervertebral-disc-space portion.

3. The device of claim 2, wherein each of the first and second uncinate-joint portions comprises:

a first surface for contacting a superior surface of the respective uncinate joint, and a second surface for contacting an inferior surface of the respective uncinate joint;

wherein, for each of first and second uncinate-joint portions, the first and second surfaces are at an oblique angle to each other.

4. The device of claim 3, wherein the oblique angle is in the range between 10 and 45 degrees.

5. The device of claim 3, wherein for each of the first and second uncinate-joint portions, the first surface is configured to, when the device is implanted in the cervical spine segment, extend into the respective uncinate joint in a direction that is at least superior relative to the intervertebral-disc-space portion.

6. The device of claim 1, wherein each of the first and second uncinate-joint portions forms at least one void for accommodating bone graft material.

7. The device of claim 1, wherein the intervertebral-disc-space portion is an intervertebral-disc-space implant.

8. A device for stabilizing a cervical spine segment, comprising:

a body having two opposing free ends, wherein each free end is configured to taper in a direction away from the sagittal plane in a medial to lateral direction of the intervertebral disc space;

each free end including a top surface configured to contact the superior surface of the respective uncinate joint and a bottom surface configured to contact the inferior surface of the respective uncinate joint;

wherein the top surface of each free end includes a lower edge and an upper edge, wherein the lower edge is at a lower elevation and is more proximal to the sagittal plane than the upper edge;

wherein the bottom surface of each free end includes a lower edge and an upper edge, wherein the lower edge of the bottom surface is at a lower elevation and is configured more proximal to the sagittal plane than the upper edge of the bottom surface, and wherein the lower edge of the bottom surface is at a lower elevation than the lower edge of the top surface; and a remaining portion of the body extending between the free ends having a top surface configured to directly contact the superior vertebra between the superior surfaces of the respective uncinate joint.

9. The device of claim 8, further including a truncated corner between the top surface and the bottom surface.

10. The device of claim 8, wherein at least one of the top surfaces of each free end is at an obtuse angle relative to an uppermost extent of a remaining portion of the body extending between the free ends.

11. The device of claim 8, wherein the top surface and the bottom surface of at least one free end are at a first oblique angle relative to each other.

12. The device of claim 11, wherein the first oblique angle is in the range between 10 and 45 degrees.

13. The device of claim 8, wherein the upper edge of the top surface is at an elevation above an uppermost extent of a remaining portion of the body extending between the free ends.

14. The device of claim 8, wherein at least one of the free ends of the body includes at least one void for accommodating bone graft material.

15. A device for stabilizing a cervical spine segment, comprising:

a body having two opposing free ends, wherein each free end is configured to taper in a direction away from the sagittal plane in a medial to lateral direction of the intervertebral disc space;

each free end including a top surface configured to contact the superior surface of the respective uncinate joint and a bottom surface configured to contact the inferior surface of the respective uncinate joint;

a remaining portion of the body between the opposing free ends including a top surface configured to directly contact the superior vertebra between the superior surfaces of the respective uncinate joint and a bottom surface configured to directly contact the inferior vertebra between the inferior surfaces of the respective uncinate joint; and wherein the top surface of each free end projects upwardly and away from the top surface of the remaining portion and wherein the bottom surface of each free end projects upwardly and away from the bottom surface of the remaining portion.

16. The device of claim 15, wherein at least one of the free end and the remaining portion of the body includes at least one void for accommodating bone graft material.

17. The device of claim 15, wherein the top surface and the bottom surface of at least one free end are at a first oblique angle relative to each other, and wherein the first oblique angle being in the range between 10 and 45 degrees.

\* \* \* \* \*